United States Patent [19]
Morishita et al.

[11] Patent Number: 5,589,360
[45] Date of Patent: Dec. 31, 1996

[54] POLYPEPTIDE, DNA FRAGMENT ENCODING THE SAME, DRUG COMPOSITION CONTAINING THE SAME AND PROCESS FOR PRODUCING THE SAME

[75] Inventors: Hideaki Morishita; Toshinori Kanamori; Masahiro Nobuhara, all of Tokyo, Japan

[73] Assignee: Mochida Pharmaceutical Co., Ltd., Tokyo, Japan

[21] Appl. No.: 431,412

[22] Filed: Apr. 28, 1995

Related U.S. Application Data

[62] Division of Ser. No. 972,387, Nov. 5, 1992, Pat. No. 5,451,659.

[30] Foreign Application Priority Data

Nov. 8, 1991 [JP] Japan .................................. 3-293472
May 12, 1992 [JP] Japan .................................. 4-119289

[51] Int. Cl.$^6$ ............................. C12P 21/06; C12N 1/20; C07H 19/00; C07H 21/00
[52] U.S. Cl. .................... 435/69.1; 435/69.2; 435/172.3; 435/252.3; 435/240.2; 435/212; 435/213; 435/218; 435/320.1; 530/300; 530/324; 536/22.1; 536/23.1; 536/23.5
[58] Field of Search .................. 435/69.1, 69.2, 435/172.3, 252.3, 240.2, 320.1, 212, 213, 218; 530/300, 324; 536/22.1, 23.1, 23.5

[56] References Cited

FOREIGN PATENT DOCUMENTS

| 0073251 | 1/1982 | European Pat. Off. . |
| 0401508 | 12/1990 | European Pat. Off. . |
| 0486001 | 5/1992 | European Pat. Off. . |

OTHER PUBLICATIONS

Jean–Philippe Salier, TIBS 15:435–439 (1990).
Ohnishi et al., Folia pharmacol. japon, vol. 85, pp. 1–6 (1985).
Laskowski, Jr., Biochemical Pharmacology, vol. 29, pp. 2089–2094 (1980).

(List continued on next page.)

Primary Examiner—Robert A. Wax
Assistant Examiner—Hyosuk Kim
Attorney, Agent, or Firm—Birch, Stewart, Kolasch & Birch, LLP

[57] ABSTRACT

This invention particularly provides a novel polypeptide having high protease-inhibiting activity, preferably FXa-inhibiting activity, which comprises, an lease as a part of the polypeptide, an amino acid sequence resulting from substitution of an amino acid for at least one amino acid in the following amino acid sequence (1), wherein the amino acid substitution is at least one substitution selected from the following substitution means (i) to (iii). It also provides a process for the production of the polypeptide, a novel DNA fragment encoding the polypeptide and a drug composition containing the same.

| Amino acid sequence (1) |
| --- |
| Cys Asn Leu Pro Ile Val Arg Gly Pro Cys |
| Arg Ala Phe Ile Gln Leu Trp Ala Phe Asp |
| Ala Val Lys Gly Lys Cys Val Leu Phe Pro |
| Tyr Gly Gly Cys Gln Gly Asn Gly Asn Lys |
| Phe Tyr Ser Glu Lys Glu Cys Arg Glu Tyr |
| Cys |

(i) Substitution of 15 position Gln counting from the N-terminus by an amino acid other than Gln.
(ii) Substitution of 42 position Tyr counting from the N-terminus by an amino acid other than Tyr.
(iii) Substitution of 7 position Arg counting from the N-terminus by an amino acid other than Arg.

13 Claims, 54 Drawing Sheets

```
        S 3 3
    5'  AGCTTAAAAA AGGGTATAAA ATAAAATGAA  AC
            ATTTTT TCCCATATTT TATTTTACTT  TGTTTCATGA   5'
                                              S 3 4

S 3 5
    5'  AAAGTACTAT TGCACTGGCA CTCTTACCGT TACTGTTT
                 TA ACGTGACCGT GAGAATGGCA ATGACAAA  TGGGGA  5'
                                                      S 1 8

S 1 9
    5'  ACCCCTGTGA CAAAAGCCGA CTCCCTAGGT CG
              CACT GTTTTCGGCT GAGGGATCCA GC    5'
                                             S 2 0
```

OTHER PUBLICATIONS

Brinkmann et al. Eur. J. Biochem., vol. 202, pp. 95–99 (1981).

Wachter et al., Hoppe–Seyler's Z. Physiol. Chem. Bd. 360:1297–1303 (1979).

Traboni et al. "Sequence of a full length cDNA...", NAR 14(15):6340 (1986).

Kaumeyer et al. "The mRNA for a proteins...", NAR 14(20):7839–7850 (1986?).

Sakuragawa et al., Chem. Abstr. 107:228724c (1987).

Fig. 1

```
S33
5' AGCTTAAAAA AGGGTATAAA ATAAAATGAA AC
   ATTTTT TCCCATATTT TATTTTACTT TGTTTCATGA 5'
                                        S34

S35
5' AAAGTACTAT TGCACTGGCA CTCTTACCGT TACTGTTT
   TA ACGTGACCGT GAGAATGGCA ATGACAAA TGGGA 5'
                                         S18

S19
5' ACCCCTGTGA CAAAAGCCGA CTCCCTAGGT CG
   CACT GTTTTCGGCT GAGGGATCCA GC 5'
                                 S20
```

Fig. 5

Y46E primer   5'   GG AAC AAG TTC GAA TCA GAG AAG GA   3'

Fig. 6

ScaI sense primer   5'   ACT ATT GCA CTG GCA CTC TTA   3'

Fig. 7

BamHI primer   5'   TGGATCCAG TTG TCA GTT GGA GAA GC   3'

Fig. 9

```
                                          -20                                  -15                                        -10
                                                                          Sca I primer
                                                              5'-ACT ATT GCA CTG GCA CTC TTA-3'
5'-AAGCTTAAAAAAGGGTATAAATAAA ATG AAA CAA AGT ACT ATT GCA CTG GCA CTG GCA CTC TTA CCG
   HindIII                  Met Lys Gln Ser Thr Ile Ala Leu Ala Leu Ala Leu Leu Pro
                                                    phoA signal peptide
                  -5                       -1  1                               5                               10
TTA CTG TTT ACC CCT GTG ACA AAG GCC ACC GTC GCC GCC TGC AAT CTC CCC ATA GTC
Leu Leu Phe Thr Pro Val Thr Lys Ala Thr Val Ala Ala Cys Asn Leu Pro Ile Val
                                          polypeptide Y46E
           15                              20                              25
CGG GGC CCC TGC CGA GCC TTC ATC CAG CTC TGG GCA TTT GAT GCT GTC AAG GGG AAG
Arg Gly Pro Cys Arg Ala Phe Ile Gln Leu Trp Ala Phe Asp Ala Val Lys Gly Lys
   30                              35                              40                 45
                                                                          Y46E primer
                                                              5'-GG AAC AAG AAG TTC GAA TCA GAG
TGC GTC CTC TTC CCC TAC GGG GGC TGC CAG GGC AAC AAG AAG TTC GAA TCA GAG
Cys Val Leu Phe Pro Tyr Gly Gly Cys Gln Gly Asn Lys Lys Phe Glu Ser Glu
        50                              55                              60                              65
AAG GA-3'
AAG GAG TGC AGA GAG TAC TGC GGT GTC CCT GGT GAT GGT GAT GAG GAG CTG CTG CGC
Lys Glu Cys Arg Glu Tyr Cys Gly Val Pro Gly Asp Gly Asp Glu Glu Leu Leu Arg
                        BamH I                                                                  3'-CG
TTC TCC AAC TGA CAACTGGATCC
Phe Ser Asn ...
AAG AGG TTG ACT GTTGACCTAGGT-5'
   BamHI primer pM575B(Y46E)
```

Fig. 10

Oligomer TV12DD  5' TG ACA AAG GCC GAC GAC GCC GCC TGC AA 3'

Fig. 11

HindIII primer  5' ACGCAAGTTCACGTAAAAAGC 3'

Fig. 12

Q19K primer  5' C AAA TGC CCA GAG CTT GAT GAA GGC TCG GCA 3'

Fig. 13 pBR BamHI primer  5' ACGATGCGTTCCGGCGTAGAG 3'

Fig. 16A

```
HindIII primer                                          -20
5'-ACGCAAGTTCACGTAAAAAGC-3'                                       5'-ACT ATT
5'-ACGCAAGTTCACGTAAAAAGCTTAAAAAAGGGTATAAATAAA ATG AAA CAA AGT ACT ATT
                       HindIII                        Met Lys Gln Ser Thr Ile
                                                       phoA signal peptide oligomer TV12DD
      -15                          -10                 -5                            -1    1
                                                       5'-TG ACA AAG GCC                  GAC GAC
      GCA CTG GCA CTC TTA-3'                                                              GAC GAC
      GCA CTG GCA CTC TTA CCG TTT ACC CCT GTG ACA AAG GCC                                 GAC GAC
      Ala Leu Ala Leu Leu Pro Phe Thr Pro Val Thr Lys Ala                                 Asp Asp Sca I primer
                           5                            10                      15
      GCC GCC TGC AA-3'
      GCC GCC TGC AAT CTC CCC ATA GTC CGG GGC CCC TGC CGA GCC TTC ATC AAG
      Ala Ala Cys Asn Leu Pro Ile Val Arg Gly Pro Cys Arg Ala Phe Ile Lys
      Polypeptide Q19K                                 3'-ACG GCT CGG AAG TAG TTC
                                                                          Q19K primer
      20                      25                      30                      35
      CTC TGG GCA TTT GAT GCT GTC AAG GGG AAG TGC GTC CTC TTC CCC TAC GGG
      Leu Trp Ala Phe Asp Ala Val Lys Gly Lys Cys Val Leu Phe Pro Tyr Gly
      GAG ACC CGT AAA C-5'

40                      45                      50
      GGC TGC CAG GGC AAC GGG AAC AAG TTC TAC TCA GAG AAG GAG TGC AGA GAG
      Gly Cys Gln Gly Asn Gly Asn Lys Phe Tyr Ser Glu Lys Glu Cys Arg Glu
```

Fig. 16B

```
                55                  60                  65                 70
TAC TGC GGT GTC CCT GGT GAT GGT GAT GAG CTG CGC TTC TCC AAC
Tyr Cys Gly Val Pro Gly Asp Gly Asp Glu Leu Arg Phe Ser Asn
            BamH I
    CAACTGGATCCTCTACGCGCCGGAACGCATCGT-3'
TGA
... 3'-GAGATGCGCGGCCTTGCGTAGCA-5'
             pBR BamHI primer
``` pM576 (Q19K)

Fig. 17

AN68 primer    5'-CTATTGG TAG ATT ACA GGC CGC GGC CTT TGT CAC AGG GGT-3'

Fig. 18

SacII primer   5'-AAG GCC GCG GCC TGT AAT CTA CCA ATA GTC-3'

Fig. 19

Q19R primer    5'-ATC AAA TGC CCA GAG ACG GAT GAA GGC TCG GC-3'

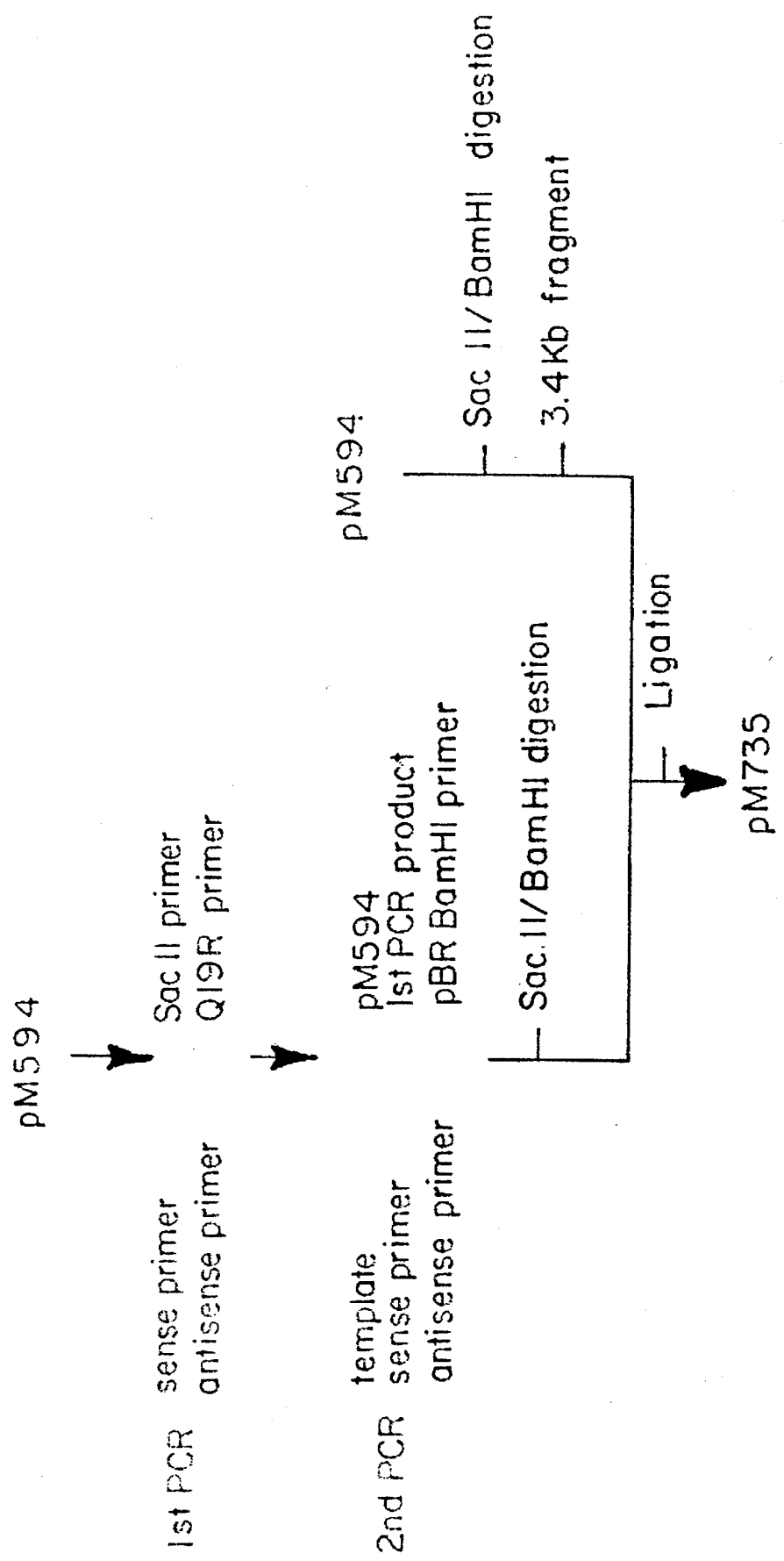

Fig. 22A

HindIII primer
5'-ACGCAAGTTCACGTAAAAAGC-3'
5'-ACGCAAGTTCACGTAAAAAGCTTAAAAAAGGGTATAAAATAAA ATG AAA CAA AGT
                       HindIII                              Met Lys Gln Ser
                                                           phoA signal peptide
                                                                        -20

```
                                         -15                                              -10                                           -5                                          -1
ACT ATT GCA CTG GCA CTC TTA CTG GCA TTT ACC CCT GTT ACA AAG GCC         5'-AAG GCC
Thr Ile Ala Leu Ala Leu Leu Leu Ala Phe Thr Pro Val Thr Lys Ala

SacII primer
GCG GCC TGT AAT CTA CCA ATA GTC-3'                                                   10                                      15
GCG GCC TGT AAT CTA CCA ATA GTC CGG GGC CCC TGC CGA GCC TTC ATC CGT
Ala Ala Cys Asn Leu Pro Ile Val Arg Gly Pro Cys Arg Ala Phe Ile Arg
Polypeptide Q19R                                        3'-CG GCT CGG AAG TAG GCA
                                                                          Q19R primer
                              20                                              25                                      30
CTC TGG GCA TTT GAT GCT GTC AAG GGG AAG TGC GTC CTC TTC CCC TAC GGG
Leu Trp Ala Phe Asp Ala Val Lys Gly Lys Cys Val Leu Phe Pro Tyr Gly
GAG ACC CGT AAA CTA-5'
                              35                      40                                      45                                  50
GGC TGC CAG GGC AAC GGG AAC AAG TTC TAC TCA GAG AAG GAG TGC AGA GAG
Gly Cys Gln Gly Asn Gly Asn Lys Phe Tyr Ser Glu Lys Glu Cys Arg Glu
```

Fig. 22B

```
         55              60              65
TAC TGC GGT GTC CCT GGT GAT GAG GAG CTG CTG CGC TTC TCC AAC
Tyr Cys Gly Val Pro Gly Asp Glu Glu Leu Leu Arg Phe Ser Asn
       BamH I
    CAACTGGATCCTCTACGCCCGGAACGCATCGT-3'
3'-GAGATGCGGGCCTTGCGTAGCA-5'
    pBR BamHI primer
``` pM735(Q19R)

Fig. 24A

```
                HindIII primer
          5'-ACGCAAGTTCACGTAAAAAGC-3'
          5'-ACGCAAGTTCACGTAAAAGCTTAAAAAGGTATAAATAAA ATG AAA CAA AGT
                                    HindIII                Met Lys Gln Ser
                                                           phoA signal peptide
                                                                    -20

-15                            -10                       -5
ACT ATT GCA CTG GCA CTC TTA CTG TTT ACC CCT GTG ACA AAG GCC
Thr Ile Ala Leu Ala Leu Leu Leu Phe Thr Pro Val Thr Lys Ala
                                                          -1

1                              5                          10                          15
GCG GCC TGT AAT CTA CCA ATA GTC CGG GGC CCC TGC CGA GCC TTC ATC AAG
Ala Ala Cys Asn Leu Pro Ile Val Arg Gly Pro Cys Arg Ala Phe Ile Lys
          Polypeptide Q19K/Y46E                    3'-ACG GCT CGG AAG TAG TTC
                                                         Q19K primer 20                         25                         30
CTC TGG GCA TTT GAT GCT GTC AAG GGG AAG TGC GTC CTC TTC CCC TAC GGG
Leu Trp Ala Phe Asp Ala Val Lys Gly Lys Cys Val Leu Phe Pro Tyr Gly
GAG ACC CGT AAA C-5'

35                         40                         45                         50
GGC TGC CAG GGC AAC GGG AAC AAG TTC GAA TCA GAG AAG GAG TGC AGA GAG
Gly Cys Gln Gly Asn Gly Asn Lys Phe Glu Ser Glu Lys Glu Cys Arg Glu
```

Fig. 24B

```
                55                  60                  65
TAC TGC GGT GTC CCT GGT GAT GGT GAT GAG GAG CTG CTG CGC TTC TCC AAC
Tyr Cys Gly Val Pro Gly Asp Gly Asp Glu Glu Leu Leu Arg Phe Ser Asn

BamH I
    CAACTGGATCCTCTACGCCGGAACGCATCGT-3'
TGA
... 3'-GAGATGCGGCCTTGCGTAGCA-5'
             pBR BamHI primer
``` pM736(Q19K/Y46E)

Fig. 25

R11E primer     5'-TCG GCA GGG GCC TTC GAC TAT TGG TAG-3'

Fig. 27A

```
                    HindIII primer
         5'-ACGCAAGTTCACGTAAAAAGC-3'
         5'-ACGCAAGTTCACGTAAAAAGCTTAAAAAAGGGTATAAAATAAA ATG AAA CAA AGT
                                HindIII                      Met Lys Gln Ser
                                                             phoA signal peptide
                                                                       -20

-15                              -10                        -5                                  -1
ACT ATT GCA CTG GCA CTC TTA CTG TTT ACC CCT GTG ACA AAG GCC
Thr Ile Ala Leu Ala Leu Leu Leu Phe Thr Pro Val Thr Lys Ala 1                           5                           10                          15
GCG GCC TGT AAT CTA CCA ATA GTC GAA GGC CCC TGC CGA GCC TTC ATC CAG
Ala Ala Cys Asn Leu Pro Ile Val Glu Gly Pro Cys Arg Ala Phe Ile Gln
                  3'-GAT GGT TAT CAG CTT CCG GGG ACG GCT-5'
                                              R11E primer
                              20                          25                          30
CTC TGG GCA TTT GAT GCT GTC AAG GGG AAG TGC GTC CTC TTC CCC TAC GGG
Leu Trp Ala Phe Asp Ala Val Lys Gly Lys Cys Val Leu Phe Pro Tyr Gly
              Polypeptide R11E/Y46E 35                          40                          45                          50
GGC TGC CAG GGC AAC GGG AAC AAG TTC GAA TCA GAG AAG GAG TGC AGA GAG
Gly Cys Gln Gly Asn Gly Asn Lys Phe Glu Ser Glu Lys Glu Cys Arg Glu
```

Fig. 27B

```
              55                  60                       65
TAC TGC GGT GTC CCT GGT GAT GAG GGT GAT GAG CTG CTG CGC TTC TCC AAC
Tyr Cys Gly Val Pro Gly Asp Glu Gly Asp Glu Leu Leu Arg Phe Ser Asn
        BamH I
TGA CAACTGGATCCTCTACGCCGGAACGCATCGT-3'
    3'-GAGATGCGGCCTTGCGTAGCA-5'
            pBR BamHI primer
``` pM726B(R11E/Y46E)

Fig. 29A

HindIII primer
5'-ACGCAAGTTCACGTAAAAAGC-3'
5'-ACGCAAGTTCACGTAAAAAGCTTAAAAAAGGGTATAAAATAAA ATG AAA CAA AGT
                      HindIII                                Met Lys Gln Ser
                                                             phoA signal peptide

```
                                     -15                                         -10                                     -5                                      -1
ACT ATT GCA CTG GCA CTC TTA CCG TTA CTG TTT ACC CCT GTG ACA AAG GCC
Thr Ile Ala Leu Ala Leu Leu Pro Leu Leu Phe Thr Pro Val Thr Lys Ala 1                            5                                          10                                       15
GCG GCC TGT AAT CTA CCA ATA GTC CGG GGC CCC TGC CGA GCC TTC ATC CAG
Ala Ala Cys Asn Leu Pro Ile Val Arg Gly Pro Cys Arg Ala Phe Ile Gln
Polypeptide Y46E-AN 20                                         25                                        30
CTC TGG GCA TTT GAT GCT GTC AAG GGG AAG TGC GTC CTC TTC CCC TAC GGG
Leu Trp Ala Phe Asp Ala Val Lys Gly Lys Cys Val Leu Phe Pro Tyr Gly 35                                        40                                       45                                        50
GGC TGC CAG GGC AAC GGG AAC AAG TTC GAA TCA GAG AAG GAG TGC AGA GAG
Gly Cys Gln Gly Asn Gly Asn Lys Phe Glu Ser Glu Lys Glu Cys Arg Glu
```

Fig. 29B

```
                55                    60                          65
TAC TGC GGT GTC CCT GGT GAT GGT GAT GAG CTG CTG CGC TTC TCC AAC
Tyr Cys Gly Val Pro Gly Asp Gly Asp Glu Leu Leu Arg Phe Ser Asn

BamH I
TGA CAACTGGATCCTCTACGCCGGAACGCATCGT-3'
    3'-GAGATGCGGCCTTGCGTAGCA-5'
         pBR BamHI primer
``` pM575C(Y46E-AN)

Fig. 31A

```
                    HindIII primer
       5'-ACGCAAGTTCACGTAAAAAGC-3'
       5'-ACGCAAGTTCACGTAAAAAGCTTAAAAAAGGGTATAAATAAA ATG AAA CAA AGT
                                HindIII                     Met Lys Gln Ser
                                                                        -20
                                                            phoA signal peptide
                                                                         -1

ACT ATT GCA CTG GCA CTC TTA CCG TTA CTG TTT ACC CCT GTG ACA AAG GCC
       Thr Ile Ala Leu Ala Leu Leu Pro Leu Leu Phe Thr Pro Val Thr Lys Ala
             -15                    -10                     -5

GCG GCC TGT AAT CTA CCA ATA GTC CGG GGC CCC TGC CGA GCC TTC ATC AAG
       Ala Ala Cys Asn Leu Pro Ile Val Arg Gly Pro Cys Arg Ala Phe Ile Lys
       1                 5                   10                  15
       Polypeptide Q19K-AN CTC TGG GCA TTT GAT GCT GTC AAG GGG AAG TGC GTC CTC TTC CCC TAC GGG
       Leu Trp Ala Phe Asp Ala Val Lys Gly Lys Cys Val Leu Phe Pro Tyr Gly
                       20                  25                  30

GGC TGC CAG GGC AAC GGG AAC AAG TTC TAC TCA GAG AAG GAG TGC AGA GAG
       Gly Cys Gln Gly Asn Gly Asn Lys Phe Tyr Ser Glu Lys Glu Cys Arg Glu
           35                  40                  45                  50
```

Fig. 31B

```
                55              60                 65
TAC TGC GGT GTC CCT GGT GAT GGT GAT GAG GAG CTG CTG CGC TTC TCC AAC
Tyr Cys Gly Val Pro Gly Asp Gly Asp Glu Glu Leu Leu Arg Phe Ser Asn

BamH I
TGA CAACTGGGATCCTCTACGCCGGAACGCATCGT-3'
    3'-GAGATGCGGCCTTGCGTAGCA-5'
        pBR BamHI primer
``` pM576B(Q19K-AN)

Fig. 33A

```
                            HindIII primer
               5'-ACGCAAGTTCACGTAAAAAGC-3'
               5'-ACGCAAGTTCACGTAAAAAGCTTAAAAAAGGGTATAAAATAAA ATG AAA CAA AGT
                                         HindIII                      Met Lys Gln Ser
                                                                           -20
                                                                      phoA signal peptide -15                              -10                    -5                          -1
ACT ATT GCA CTG GCA CTC TTA CCG TTA CTG TTT ACC CCT GTG ACA AAG GCC
Thr Ile Ala Leu Ala Leu Leu Pro Leu Leu Phe Thr Pro Val Thr Lys Ala 1                              5                      10                         15
GCG GCC TGT AAT CTA CCA ATA GTC CGG GGC CCC TGC CGA GCC TTC ATC CGT
Ala Ala Cys Asn Leu Pro Ile Val Arg Gly Pro Cys Arg Ala Phe Ile Arg
Polypeptide Q19R/Y46E 20                             25                         30
CTC TGG GCA TTT GAT GCT GTC AAG GGG AAG TGC GTC CTC TTC CCC TAC GGG
Leu Trp Ala Phe Asp Ala Val Lys Gly Lys Cys Val Leu Phe Pro Tyr Gly 35                              40                        45                      50
GGC TGC CAG GGC AAC GGG AAC AAG TTC GAA TCA GAG AAG GAG TGC CGA GAG
Gly Cys Gln Gly Asn Gly Asn Lys Phe Glu Ser Glu Lys Glu Cys Arg Glu
```

Fig. 33B

```
                  55                  60                          65
TAC TGC GGT GTC CCT GGT GAT GGT GAT GAG CTG CTG CGC TTC TCC AAC
Tyr Cys Gly Val Pro Gly Asp Gly Asp Glu Glu Leu Leu Arg Phe Ser Asn
        BamH I
TGA CAACTGGATCCTCTACGCCGGAACGCATCGT-3'
    3'-GAGATGCGGCCTTGCGTAGCA-5'
        pBR BamHI primer
``` pM737B(Q19R/Y46E)

Fig. 34

Linker 710

AGCTTAAAAA AGGGTATAAA ATAAAAATGAA ACAAAGTACT ATTGCACTGG CACTCTTACC
         ATTTTT TCCCATATTT TATTTTACTT TGTTTCATGA TAACGTGACC GTGAGAATGG

GTTACTGTTT ACCCCTGTGA CAAAGGCCGC TGTGCTACCG CAAGAAGAAG AAGGCTCGGG
CAATGACAAA TGGGGACACT GTTTCCGGCG ACACGATGGC GTTCTTCTTC TTCCGAGCCC

TATGGCCGCC TGTAATCTAC CAATAGTCCG GGGCC
ATACCGGCGG ACATTAGATG GTTATCAGGC C

Fig. 35

Y46D primer    5'    GGG AAC AAG TTC GAC TCA GAG AAG G    3'

HindIII primer
5'-ACGCAAGTTCACGTAAAAGC-3'
5'-ACGCAAGTTCACGTAAAAGCTTAAAAAAGTTATAAAAATAAA ATG AAA CAA ACT
             HindIII                               -20
                                                         Met Lys Gln Ser ATT GCA CTG GCA CTC TTA CCG TTA CTG TTT ACC CCT GTG ACA AAG
Ile Ala Leu Ala Leu Leu Pro Leu Leu Phe Thr Pro Val Thr Lys
                                                                                1

GCC GCT GTG CTA CCG CAA GAA GAA GGC TCG GGT ATG GCC GCC
Ala Ala Val Leu Pro Gln Glu Glu Gly Ser Gly Met Ala Ala
                                5

TGT AAT CTA CCA ATA GTC CGG GGC CCC TGC CGA GCC TTC ATC AAG
Cys Asn Leu Pro Ile Val Arg Gly Pro Cys Arg Ala Phe Ile Lys
                                     3'-ACG GCT CGG AAG TAG TTC
                                                             Q19K primer
              10                                        15

CTC TGG GCA TTT GAT GCT GTC AAG GGG AAG TGC GTC CTC TTC CCC
Leu Trp Ala Phe Asp Ala Val Lys Gly Lys Cys Val Leu Phe Pro
GAG ACC CGT-5'
      20                       25                                    30

Fig. 36B

```
                              Y46D primer
                    5'- GGG AAC AAG AAG TTC GAC TCA GAG AAG
TAC GGG GGC TGC CAG GGC AAG GGG AAC AAG AAG TTC GAC TCA GAG AAG
Tyr Gly Gly Cys Gln Gly Lys Gly Asn Lys Lys Phe Asp Ser Glu Lys
             35                      40                      45

G-3'
GAG TGC AGA GAG TAC TGC GGT GTC CCT GGT GAT GGT GAT GAG GAG
Glu Cys Arg Glu Tyr Cys Gly Val Pro Gly Asp Gly Asp Glu Glu
             50                      55                      60

BamHI
CTG CTG CGC TTC TCC AAC TGA   CAACTGATCCTCTACGCCGGACGGCATCGT
Leu Leu Arg Phe Ser Asn ...  3'- GAGATGCGGCCTGCGTAGCA-5'
             65         68               pBR BamHI primer
```

HindIII primer
5'-ACGCAAGTTCACGTAAAAAGC-3'
ACGCAAGTTCACGTAAAAAGCTTAAAAAAGGGTATAAAATAAA ATG AAA CAA AGT ACT
        HindIII            Met Lys Gln Ser Thr ATT GCA CTG GCA CTC TTA CCG TTA CTG TTT ACC CCT GTG ACA AAG
Ile Ala Leu Ala Leu Leu Pro Leu Leu Phe Thr Pro Val Thr Lys GCC GCT GTG CTA CCG CAA GAA GAA GGC TCG GGT ATG GCC GCC
Ala Ala Val Leu Pro Gln Glu Glu Gly Ser Gly Met Ala Ala
 5                      1

TGT AAT CTA CCA ATA GTC CGG GGC CCC TGC CGA GCC TTC ATC CGT
Cys Asn Leu Pro Ile Val Arg Gly Pro Cys Arg Ala Phe Ile Arg
              3'-CG                            
     10                 15
                                Q19R primer
                          GCT CGG AAG TAG GCA CTC TGG GCA TTT GAT GCT GTC AAG GGG AAG TGC GTC CTC TTC CCC
Leu Trp Ala Phe Asp Ala Val Lys Gly Lys Cys Val Leu Phe Pro
GAG ACC CGT AAA CTA-5'
Glu
    20             25          30

Fig. 37B

```
                                                    Y46D primer
                                          5'- GGG AAC AAG AAG TTC GAC TCA GAG AAG
TAC GGG GGC TGC CAG GGC AAC GGG AAC AAG AAG TTC GAC TCA GAG AAG
Tyr Gly Gly Cys Gln Gly Asn Gly Asn Lys Phe Asp Ser Glu Lys
         35                    40                    45
G-3'
GAG TGC AGA GAG TAC TGC GGT GTC CCT GGT GAT GGT GAT GAG GAG
Glu Cys Arg Glu Tyr Cys Gly Val Pro Gly Asp Gly Asp Glu Glu
         50                    55                    60
                                          BamHI
CTG CTG CGC TTC TCC AAC TGA . . . CAACTGGATCCTCTACGCCCGGACGCATCGT
Leu Leu Arg Phe Ser Asn                3'- GAGATGCGGCCTGCGTAGCA-5'
         65         68                         pBR BamHI primer
```

Fig. 38

R11Q primer    5'   CG GCA GGG GCC CTG GAC TAT TGG TA 3'

```
           HindIII primer
5'-ACGCAAGTTCACGTAAAAAGC-3'
   ACGCAAGTTCACGTAAAAAGCTTAAAAAAGGGTATAAATAAA ATG AAA CAA AGT ACT
                        HindIII                     Met Lys Gln Ser Thr ATT GCA CTG GCA CTC TTA CCG TTA CTG TTT ACC CCT GTG ACA AAG
Ile Ala Leu Ala Leu Leu Pro Leu Leu Phe Thr Pro Val Thr Lys GCC GCT GTG CTA CCG CAA GAA GAA GGC TCG GGT ATG GCC GCC
Ala Ala Val Leu Pro Gln Glu Glu Gly Ser Gly Met Ala Ala
                                                          1

TGT AAT CTA CCA ATA GTC CAG GGC CCC TGC CGA GCC TTC ATC AAG
Cys Asn Leu Pro Ile Val Gln Gly Pro Cys Arg Ala Phe Ile Lys
              3'-AT GGT TAT CAG GTC CCG GGG ACG GCT CGG AAG TAG TTC
                 R11Q primer                              Q19K primer
                    5                       10                      15

CTC TGG GCA TTT GAT GCT GTC AAG GGG AAG TGC GTC CTC TTC CCC
Leu Trp Ala Phe Asp Ala Val Lys Gly Lys Cys Val Leu Phe Pro
GAG ACC CGT-5'
      20                      25                      30
```

Fig. 39B

```
                                              Y46D primer
                               5'- GGG AAC AAG AAG TTC GAC TCA GAG AAG
                                   GGG AAC AAG AAG TTC GAC TCA GAG AAG
                                   Gly Asn Lys Phe Asp Ser Glu Lys
                                    40                          45

TAC GGG GGC TGC CAG GGC                                              GAG TGC AGA GAG TAC TGC GGT GTC CCT GGT GAT GGT GAT GAG GAG
Tyr Gly Gly Cys Gln Gly                                              Glu Cys Arg Glu Tyr Cys Gly Val Pro Gly Asp Gly Asp Glu Glu
         35                                                                   50                          55                          60
G-3'

BamHI
CTG CTG CGC TTC TCC AAC TGA CAACTGGATCCTCTACGCCGGACGCATCGT
Leu Leu Arg Phe Ser Asn ...  3'- GAGATGCGGCCTGCGTAGCA-5'
         65             68              pBR BamHI primer
```

Fig. 40

R11D primer    5' CG GCA GGG GCC ATC GAC TAT TGG TA   3'

Hind III primer
5'-ACGCAAGTTCACGTAAAAAGC-3'
ACGCAAGTTCACGTAAAAAGCTTAAAAAAGGGTATAAATAAA ATG AAA CAA AGT ACT
                     HindIII                             Met Lys Gln Ser Thr ATT GCA CTG GCA CTC TTA CCG TTA CTG TTT ACC CCT GTG ACA AAG
Ile Ala Leu Ala Leu Leu Pro Leu Leu Phe Thr Pro Val Thr Lys
                            5                          10

GCC GCT GTG CTA CCG CAA GAA GGC TCG GGT ATG GCC
Ala Ala Val Leu Pro Gln Glu Gly Ser Gly Met Ala
                                              1

TGT AAT CTA CCA ATA GTC GAT GGC CCC TGC CGA GCC TTC ATC AAG
Cys Asn Leu Pro Ile Val Asp Gly Pro Cys Arg Ala Phe Ile Lys
                            3'-AT GGT TAT CAG CTA CCG GGG ACG GCT CGG AAG TAG TTC
                                         R11D primer                Q19K primer
                    20                              25                      30

CTC TGG GCA TTT GAT GCT GTC AAG GGG AAG TGC GTC CTC TTC CCC
Leu Trp Ala Phe Asp Ala Val Lys Gly Lys Cys Val Leu Phe Pro
GAG ACC CGT-5'
                    20                              25                      30

Fig. 41B

```
                                                Y46D primer
                                    5'- GGG AAC AAG AAG TTC GAC TCA GAG AAG
TAC GGG GGC TGC CAG GGC AAC GGG AAC AAG AAG TTC GAC TCA GAG AAG
Tyr Gly Gly Cys Gln Gly Asn Gly Asn Lys Lys Phe Asp Ser Glu Lys
             35                  40                  45

G-3'
GAG TGC AGA GAG TAC TGC GGT GTC CCT GGT GAT GGT GAT GAG GAG
Glu Cys Arg Glu Tyr Cys Gly Val Pro Gly Asp Gly Asp Glu Glu
             50                  55                  60

BamHI
CTG CTG CGC TTC TCC AAC TGA CAACTGGATCCTCTACGCCGGACGCATCGT
Leu Leu Arg Phe Ser Asn ...        3'- GAGATGCGGCCTGCGTAGCA-5'
             65       68                    pBR BamHI primer
```

Fig. 42

R11L primer    5' CG GCA GGG GCC CAG GAC TAT TGG TA   3'

HindIII primer
5'-ACGCAAGTTCACGTAAAAAGC-3'
5'-ACGCAAGTTCACGTAAAAAGCTTAAAAAAAGGGTATAAAATAAA ATG AAA CAA ACT
                      HindIII                                    Met Lys Gln Ser ATT GCA CTG GCA CTC TTA CCG TTA CTG TTT ACC CCT GTG ACA AAG
Ile Ala Leu Ala Leu Leu Pro Leu Leu Phe Thr Pro Val Thr Lys
                          5                               1

GCC GCT GTG CTA CCG CAA GAA GAA GGC TCG GGT ATG GCC GCC
Ala Ala Val Leu Pro Gln Glu Glu Gly Ser Gly Met Ala Ala
                                                        1

TGT AAT CTA CCA ATA GTC CTG GGC CCC TGC CGA GCC TTC ATC AAG
Cys Asn Leu Pro Ile Val Leu Gly Pro Cys Arg Ala Phe Ile Lys
              3'-AT GGT TAT CAG GAC CCG GGG ACG GCT-5'          3'-ACG GCT CGG AAG TAG TTC
                 R11L primer                                        Q19K primer
                      10                                              15

CTC TGG GCA TTT GAT GCT GTC AAG GGG AAG TGC GTC CTC TTC CCC
Leu Trp Ala Phe Asp Ala Val Lys Gly Lys Cys Val Leu Phe Pro
GAG ACC CGT-5'
     20                              25                    30

Fig. 43B

```
                                                          Y46D primer
                                        5'- GGG AAC AAG AAG TTC GAC TCA GAG AAG
TAC GGG GGC TGC CAG GGC    GGG AAC AAG AAG TTC GAC TCA GAG AAG
Tyr Gly Gly Cys Gln Gly    Gly Asn Lys Lys Phe Asp Ser Glu Lys
              35                         40                     45

G-3'
GAG TGC AGA GAG TAC TGC GGT GTC CCT GGT GAT GGT GAT GAG GAG
Glu Cys Arg Glu Tyr Cys Gly Val Pro Gly Asp Gly Asp Glu Glu
          50                      55                     60

BamHI
CTG CTG CGC TTC TCC AAC TGA CAACTGGATCCTCTACGCCGGACGCATCGT
Leu Leu Arg Phe Ser Asn ...    3'- GAGATGCGGCCTGCGTAGCA-5'
          65           68               pBR BamHI primer
```

HindIII primer
5'-ACGCAAGTTCACGTAAAAAGC-3'
ACGCAAGTTCACGTAAAAAGCTTAAAAAAGGGTATAAATAAA ATG AAA CAA AGT ACT
                     HindIII                                Met Lys Gln Ser Thr ATT GCA CTG GCA CTC TTA CCG TTA CTG TTT ACC CCT GTG ACA AAG
Ile Ala Leu Ala Leu Leu Pro Leu Leu Phe Thr Pro Val Thr Lys GCC GCT GTG CTA CCG CAA GAA GAA GGC CCC TGC CGA GCC TTC ATC AAG
Ala Ala Val Leu Pro Gln Glu Glu Gly Pro Cys Arg Ala Phe Ile Lys
                                          1

TGT AAT CTA CCA ATA GTC GAA GGC CCC TGC CGA GCC TTC ATC AAG
Cys Asn Leu Pro Ile Val Glu Gly Pro Cys Arg Ala Phe Ile Lys
                5                        10                    15
     3'-GAT GGT TAT CAG CTT CCG GGG ACG          3'-ACG GCT CGG AAG TAG TTC
        R11E primer                                       Q19K primer CTC TGG GCA TTT GAT GCT GTC AAG GGG AAG TGC GTC CTC TTC CCC
Leu Trp Ala Phe Asp Ala Val Lys Gly Lys Cys Val Leu Phe Pro
         20                      25                       30
GAG ACC CGT-5'

Fig. 44B

```
                                              Y46E primer
                              5'-GG AAC AAG AAG TTC GAA TCA GAG AAG
TAC GGG GGC TGC CAG GGC AAC AAG AAG TTC GAA TCA GAG AAG
Tyr Gly Gly Cys Gln Gly Asn Lys Phe Glu Ser Glu Lys
         35                      40                      45

G-3'
GAG TGC AGA GAG TAC TGC GGT GTC CCT GGT GAT GGT GAT GAG GAG
Glu Cys Arg Glu Tyr Cys Gly Val Pro Gly Asp Gly Asp Glu Glu
         50                      55                      60

BamHI
CTG CGC TTC TCC AAC TGA CAACTGGATCCTCTACGCCGGACGCATCGT
Leu Arg Phe Ser Asn                  3'-GAGATGCGGCCTGCGTAGCA-5'
         65        68                           pBR BamHI primer
```

POLYPEPTIDE, DNA FRAGMENT ENCODING THE SAME, DRUG COMPOSITION CONTAINING THE SAME AND PROCESS FOR PRODUCING THE SAME

This application is a divisional of application Ser. No. 07/972,387, filed on Nov. 5, 1992, now U.S. Pat. No. 5,451,659 the entire contents of which are hereby incorporated by reference.

FIELD OF THE INVENTION

This invention relates to a novel polypeptide, a novel DNA fragment encoding the novel polypeptide, a vector containing the novel DNA fragment, a transformant capable of producing the novel polypeptide, a process for producing the novel polypeptide, a drug composition containing the novel polypeptide as an effective ingredient and a protease inhibition process in which the novel polypeptide is used.

BACKGROUND OF THE INVENTION

As it is universally known, various proteases including trypsin and chymotrypsin exist in the body. While these proteases take important roles in the body such as digestion, defense mechanism, blood coagulation and fibrinolysis and the like, it has been revealed by previous studies that they also cause diseases and troubles directly or indirectly. Shock, pancreatitis, disseminated intravascular coagulation syndrome (DIC) and the like are known as typical diseases which are caused by abnormal activation of proteases.

Various types of protease inhibitors have been used with the aim of treating such protease-related diseases. The protease inhibitors so far used as pharmaceutical drugs for the treatment of these diseases are divided into two groups, namely chemically synthesized compounds and natural substances in most cases, chemically synthesized compounds are applicable to oral administration and have a broad enzyme inhibition spectrum, while each of the natural substances inhibits each own specific protease and is possessed of other functions than its enzyme inhibition function, such as a cell growth enhancing activity and the like.

Inhibition spectrum of each natural protease inhibitor is greatly related to the kinds and sequence of amino acids on its active center. For example, trypsin type enzymes are inhibited by a protease inhibitor when an amino acid of a principal position $P_1$ on the active center of the protease inhibitor is Lys or Arg, chymotrypsin type enzymes are inhibited when the $P_1$ amino acid is Phe or Tyr and elastase type enzymes are inhibited when the $P_1$ amino acid is Ala, Ser or Val (Laskowski M., Jr., *Biochem. Pharmacol.*, vol. 29, pp. 2089–2094, 1980). In consequence, it is assumed that inhibition spectrum of a natural protease inhibitor can be changed by substituting an amino acid which is a composing element of the active center of the inhibitor. Such an approach has already been applied to several natural protease inhibitors. For example, Brinkmann et al. have reported that chymotrypsin inhibition activity of aprotinin was improved when positions $P_1$ and $P'_2$ on the active center of aprotinin were substituted by a hydrophobic amino acid such as Phe, Tyr, Leu or the like (Thomas Brinkmann et al., *Eur. J. Biochem.*, vol. 202, pp. 95–99, 1991). In addition, Fritz et al. have prepared a substance by substituting an amino acid on the active center of Bikunins (HI-30) by other amino acid, and have measured its elastase- and trypsin-inhibiting activities (Japanese Patent Application Kokai No. 3-255099, 1991; European Patent EP401508, 1990).

Since changes in the properties of a protease inhibitor caused by such an amino acid substitution exert influence not only upon its enzyme inhibition spectrum but also upon its route of administration, pharmacological function and the like, it is important to develop various types of protease inhibitors having such new characteristics for use in the treatment of diseases and to use the new inhibitors according to the conditions of each disease to be treated.

SUMMARY OF THE INVENTION

In view of the above, it therefore becomes an object of the present invention to provide a novel polypeptide as a protease inhibitor having new characteristics as described above, especially having high FXa inhibition activity, which comprises, at least as a pare of the polypeptide, an amino acid sequence resulting from substitution of an amino acid for at least one amino acid in the following amino acid sequence (1), wherein the amino acid substitution is at least one substitution selected from the following substitution means (i) to (iii).

| Amino acid sequence (1) |
| --- |
| Cys Asn Leu Pro Ile Val Arg Gly Pro Cys |
| Arg Ala Phe Ile Gln Leu Trp Ala Phe Asp |
| Ala Val Lys Gly Lys Cys Val Leu Phe Pro |
| Tyr Gly Gly Cys Gln Gly Asn Gly Asn Lys |
| Phe Tyr Ser Glu Lys Glu Cys Arg Glu Tyr |
| Cys (Seq. I.D. NO.: 66) |

Substitution means
(i) Substitution of 15 position Gln counting from the N-terminus by an amino acid other than Gln.
(ii) Substitution of 42 position Tyr counting from the N-terminus by an amino acid other than Tyr.
(iii) Substitution of 7 position Arg counting from the N-terminus by an amino acid other than Arg.

Another object of the present invention is to provide a DNA fragment having a nucleotide sequence which encodes the novel polypeptide, a vector containing the DNA fragment, a transformant transformed with the DNA fragment or with the vector containing the DNA fragment and a process for producing the novel polypeptide.

A further object of the present invention is to provide a drug composition containing the novel polypeptide as an effective ingredient and a protease inhibition process in which the novel polypeptide is used.

Other objects and advantages of the present invention will be made apparent as the description progresses.

BRIEF DESCRIPTION OF THE DRAWINGS

FIG. 1 shows nucleotide sequences of oligonucleotides S33, S34, S35, S18, S19 and S20.

FIG. 5 shows the nucleotide sequence of the Y46E primer.

FIG. 6 shows the nucleotide sequence of the ScaI sense primer.

FIG. 7 shows the nucleotide sequence of the BamHI primer.

FIG. 9 shows the nucleotide sequence of a region of plasmid pM575B from its HindIII site to its BamHI site, and a corresponding amino acid sequence.

FIG. 10 shows the nucleotide sequence of the oligomer TV12DD.

FIG. 11 shows the nucleotide sequence of the HindIII primer.

FIG. 12 shows the nucleotide sequence of the Q19K primer.

FIG. 13 shows the nucleotide sequence of the pBR BamHI primer.

FIG. 16 shows the nucleotide sequence of the a region of plasmid pM576 from its HindIII site to its BamHI site, and a corresponding amino acid sequence.

FIG. 17 shows the nucleotide sequence of the AN68 primer.

FIG. 18 shows the nucleotide sequence of the SacII primer.

FIG. 19 shows the nucleotide sequence of the Q19R primer.

FIG. 21 is a graph showing a process for the construction of plasmid pM735.

FIG. 22 shows the nucleotide sequence of a region of plasmid pM735 from its HindIII site to its BamHI site, and a corresponding amino acid sequence.

FIG. 24 shows the nucleotide sequence of a region of plasmid pM736 from its HindIII site to its BamHI site, and a corresponding amino acid sequence.

FIG. 25 shows the nucleotide sequence of the R11E primer.

FIG. 27 shows the nucleotide sequence of a region of plasmid pM726B from its HindIII site to its BamHI site, and a corresponding amino acid sequence.

FIG. 29 shows the nucleotide sequence of a region of plasmid pM575C from its HindIII site to its BamHI site, and a corresponding amino acid sequence.

FIG. 31 shows the nucleotide sequence of a region of plasmid pM576B from its HindIII site to its BamHI site, and a corresponding amino acid sequence.

FIG. 33 shows the nucleotide sequence of a region of plasmid pM737B from its HindIII site to its BamHI site, and a corresponding amino acid sequence.

FIG. 34 shows the nucleotide sequence of Linker 710.

FIG. 35 shows the nucleotide sequence of the Y46D primer.

FIG. 36 shows the nucleotide sequence of a region of plasmid pM727 from its HindIII site to its BamHI site, and a corresponding amino acid sequence.

FIG. 37 shows the nucleotide sequence of a region of plasmid pM744 from its HindIII site to its BamHI site, and a corresponding amino acid sequence.

FIG. 38 shows the nucleotide sequence of the R11Q primer.

FIG. 39 shows the nucleotide sequence of a region of plasmid pM741 from its HindIII site to its BamHI site, and a corresponding amino acid sequence.

FIG. 40 shows the nucleotide sequence of R11D primer.

FIG. 41 shows the nucleotide sequence of a region of plasmid pM742 from its HindIII site to its BamHI site, and a corresponding amino acid sequence.

FIG. 42 shows the nucleotide sequence of the R11L primer.

FIG. 43 shows the nucleotide sequence of a region of plasmid pM743 from its HindIII site to its BamHI site, and a corresponding amino acid sequence.

FIG. 44 shows the nucleotide sequence of a region of plasmid pM738 from its HindIII site to its BamHI site, and a corresponding amino acid sequence.

DETAILED DESCRIPTION OF THE INVENTION

Figure 2:
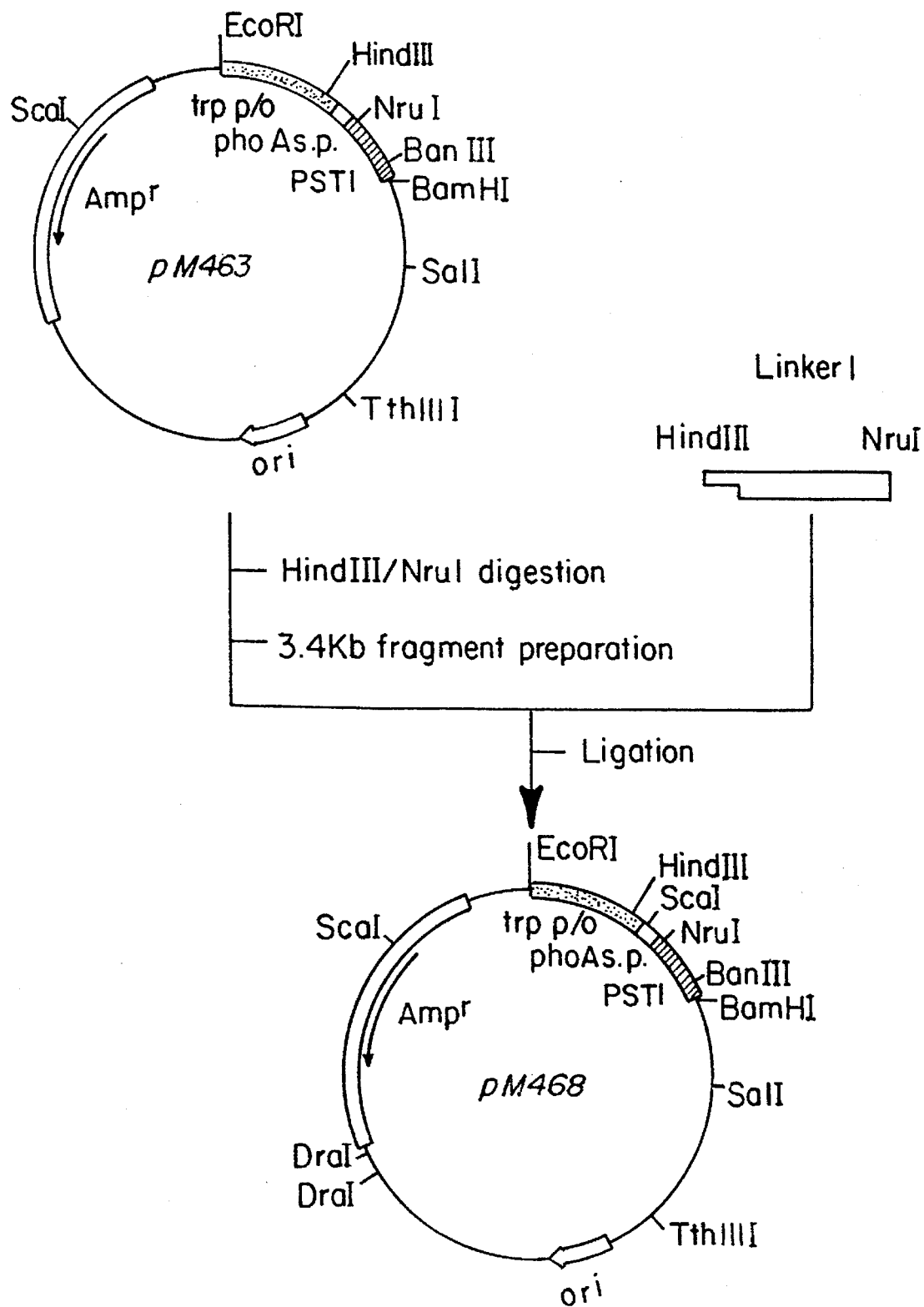
FIG. 2 is a schematic for a process for the construction of plasmid pM468.

With the aim of overcoming aforementioned problems involved in the prior art, the inventors of the present invention have conducted intensive studies on the development of a new protease inhibitor by introducing a mutation into a polypeptide which comprises an amino acid sequence represented by the following formula 1.

| Formula 1 | | | | | | | | | |
|---|---|---|---|---|---|---|---|---|---|
| | | | | 5 | | | | | 10 |
| Cys | Asn | Leu | Pro | Ile | Val | Arg | Gly | Pro | Cys |
| | | | | 15 | | | | | 20 |
| Arg | Ala | Phe | Ile | Gln | Leu | Trp | Ala | Phe | Asp |
| | | | | 25 | | | | | 30 |
| Ala | Val | Lys | Gly | Lys | Cys | Val | Leu | Phe | Pro |
| | | | | 35 | | | | | 40 |
| Tyr | Gly | Gly | Cys | Gln | Gly | Asn | Gly | Asn | Lys |
| | | | | 45 | | | | | 50 |
| Phe | Tyr | Ser | Glu | Lys | Glu | Cys | Arg | Glu | Tyr |
| Cys | | | | | | | | | |

(SEQ. I.D. NO.: 67)

The polypeptide represented by the above amino acid sequence of formula 1 has been found for the first time by the present inventors as a polypeptide having an activity to inhibit activated blood coagulation factor X (to be referred to as "FXa" hereinafter) (Japanese Patent Application No. 03-325220). The amino acid sequence of this polypeptide coincides with a part of the amino acid sequence of urinary trypsin inhibitor (UTI) or Bikunins (HI-30). However, the polypeptide represented by the above amino acid sequence of formula 1 is clearly different from UTI or HI-30, because the polypeptide of formula 1 has a high FXa-inhibiting activity while the latter two peptides hardly show such an activity. The inventors of the present invention have conducted intensive studies with the aim of improving the value of the polypeptide of formula 1. As the results, the present inventors have succeeded in obtaining a novel polypeptide having new characteristics by substituting an amino acid at a specific position in the above amino acid sequence with another amino acid, a position which could not be predicted from the information so far available. In other words, the inventors of the present invention have succeeded in developing a novel polypeptide having new characteristics unknown in the prior art by substituting an amino acid at a specific position with another amino acid, at a position which is different from the active center reported by Wachter et al. and by Sailer (Wachter et al, *Hoppe-Seyler's Z. Physiol Chem* vol. 360, pp. 1297–1303, 1979; and Jean-Philippe Sailer, TIBS, vol. 15, pp. 435–439, 1990).

According to a first aspect of the present invention, there is provided a novel polypeptide which contains, at least as a part thereof, an amino acid sequence resulting from substitution of an amino acid for at least one amino acid in the aforementioned amino acid sequence represented by formula 1.

According to a second aspect of the present invention, there is provided a novel DNA fragment containing a nucleotide sequence which encodes the polypeptide described in the first aspect of the present invention.

According to a third aspect of the present invention, there is provided a vector which contains the DNA fragment described in the second aspect of the present invention.

According to a fourth aspect of the present invention, there is provided a transformant which is transformed with the DNA fragment described in the second aspect of the present invention.

According to a fifth aspect of the present invention, there is provided a transformant which is transformed with the vector described in the third aspect of the present invention.

According to a sixth aspect of the present invention, there is provided a process for producing the polypeptide described in the first aspect of the present invention, which comprises the following steps:
(a) preparing a DNA fragment containing a nucleotide sequence which encodes the polypeptide described in the first aspect of the present invention,
(b) isolating a transformant by transforming a host cell with the DNA fragment prepared in the above step (a), and
(c) culturing the transformant obtained in the above step b) thereby allowing the transformant to produce the polypeptide described in the first aspect of the present invention and subsequently recovering said polypeptide from cultured medium.

According to a seventh aspect of the present invention, there is provided a process for producing the polypeptide described in the first aspect of the present invention, which comprises the following order of steps of:
(a) preparing a DNA fragment containing a nucleotide sequence which encodes the polypeptide described in the first aspect of the present invention,
(b) preparing a vector which contains the DNA fragment obtained in the above step (a),
(c) isolating a transformant by transforming a host cell with the vector obtained in the above step b), and
(d) culturing the transformant obtained in the above step c) thereby allowing it to produce a polypeptide described in the first aspect of the present invention and subsequently recovering said polypeptide from cultured medium.

According to an eighth aspect of the present invention, there is provided a drug composition which contains the polypeptide described in the first aspect of the present invention as an active ingredient.

According to a ninth aspect of the present invention, there is provided a protease inhibition process which comprises using the polypeptide described in the first aspect of the present invention.

The following describes the present invention in detail

The novel polypeptide of the first aspect of the present invention is characterized in that it contains, at least as a part thereof, an amino acid sequence resulting from substitution of at least one amino acid in the aforementioned amino acid sequence represented by formula 1 with a different amino acid.

The term "a polypeptide containing an amino acid sequence as a part thereof" as used herein means that, when a polypeptide is defined by its primary structure, the polypeptide may be defined either by the amino acid sequence itself or by an amino acid sequence in which the N-terminus, the C-terminus or both termini of the former amino acid sequence is or are supplemented with one or more optional amino acids. Polypeptide-defining elements other than the primary structure, such as the presence of a sugar chain and the like, are not particularly limited.

Preferably, substitution of an amino acid may be effected at least at the 7 position, the 15 position or 42 position of the amino acid sequence of the aforementioned formula 1, counting from its N-terminus. In other words, an amino acid sequence to be used at least as a part of the novel polypeptide of the first aspect of the present invention may be derived from the amino acid sequence of formula 1 by substituting only Arg at the 7 position of the sequence with another amino acid, only Gln at the 15 position with another amino acid or only Tyr at the 42 position with another amino acid, counting from the N-terminus of the amino acid sequence. Also, at least two of the 7 position Arg, 15 position Gln and 42 position Tyr may be substituted simultaneously with other amino acids. In addition to these substitutions, one or more other amino acids at different positions may be substituted by optional amino acids.

Preferably, the substitution of the amino acids may at least increase the protease inhibiting activity of the polypeptide or improve the secretion of the polypeptide from host cells when the polypeptide is produced by recombinant DNA techniques in comparison with the original polypeptide prior to the amino acid substitution.

More preferably, the substitution of the amino acids may be effective for improving at least one property of the polypeptide selected from the group consisting of;
(i) increasing the activities of the polypeptide to inhibit FXa,
(ii) having an improved secretion from a transformant when the polypeptide is produced by recombinant DNA techniques, and
(iii) increasing the activities of the polypeptide to inhibit elastase.

Substitution of the 15 position Gln or 42 position Tyr by other amino acids is effective for changing protease inhibiting activity of a polypeptide which contains the amino acid sequence of formula 1, especially for altering its activity to inhibit at least FXa. In addition, substitution of the 7 position Arg with another amino acid is effective for changing its protease inhibiting activity, especially at least elastase.

Substitution of the 7 position Arg with another amino acid is effective for easy secretion of the resulting polypeptide from host cells when the polypeptide is produced by recombinant DNA techniques. When an least two of the 7 position, 15 position and 42 position amino acids are substituted simultaneously by other amino acids, it is possible no obtain additive effects of the employed substitutions.

The polypeptide of the first aspect of the present invention may preferably contain, at least as a part thereof, an amino acid sequence resulting from at least one substitution in the amino acid sequence of formula 1, which is selected from the following substitutions (1) to (11);

(1) substitution of Lys for the 15 position Gln counting from the N-terminus,
(2) substitution of Arg for the 15 position Gln counting from the N-terminus,
(3) substitution of Glu for the 42 position Tyr counting from the N-terminus,
(4) substitution of Asp for the 42 position Tyr counting from the N-terminus,
(5) substitution of Glu for the 7 position Arg counting from the N-terminus,
(6) substitution of Gln for the 7 position Arg counting from the N-terminus,
(7) substitution of Asp for the 7 position Arg counting from the N-terminus,
(8) substitution of Leu for the 7 position Arg counting from the N-terminus,
(9) substitution of Asn for the 7 position Arg counting from the N-terminus,
(10) substitution of Ser for the 7 position Arg counting from the N-terminus, and
(11) substitution of Ala for the 7 position Arg counting from the N-terminus.

Aforementioned effects of the substitution of at least one amino acid in the amino acid sequence of formula 1 on the properties of the resulting polypeptide can also be found when the N-terminus, the C-terminus or both termini of the formula 1 sequence is or are supplemented with one or more optional amino acids. In consequence, the novel polypeptide of the present invention may contain, at lease as a part thereof, an amino acid sequence in which the N-terminus, the C-terminus or both termini of the amino acid sequence resulting from substitution of at least one amino acid in the amino acid sequence of formula 1 by other amino acid is or are further added with one or more optional amino acids. The kinds and numbers of amino acids to be added are not particularly limited, provided that the characteristic nature of the novel polypeptide of the present invention is not spoiled completely by the amino acid addition.

A preferred amino acid sequence to be added to the N-terminus may be selected from the following sequences (1) to (5);

(1) Asp Asp Ala Ala (SEQ. I.D. NO.:69),
(2) Thr Val Ala ala (SEQ. I.D. NO.:71)
(3) Val Ala Ala,
(4) Ala Ala, and
(5) Ala.

A derivative of each of the above amino acid sequences (1) to (5) may also be used as an amino acid sequence to be added to the N-terminus, such as a derivative in which at least one amino acid in any of the amino acid sequences (1) to (5) is substituted with another optional amino acid, a derivative in which at least one optional amino acid is added to or deleted from any of the amino acid sequences (1) to (5) or a derivative in which such substitution, addition and deletion are effected simultaneously in any of the amino acid sequences (1) to (5). These added sequences are useful when the novel polypeptide is produced using an *Escherichia coli* cell culture.

A preferred amino acid sequence to be added to the C-terminus may be selected be from the following sequences (1) to (15);

(1) Gly Val Pro Gly Asp Gly Asp Glu Glu Leu Leu Arg Phe Ser Asn SEQ. I.D. NO.: 73),
(2) Gly Val Pro Gly Asp Gly Asp Glu Glu Leu Leu Arg Phe Ser,
(3) Gly Val Pro Gly Asp Gly Asp Glu Glu Leu Leu Arg Phe,
(4) Gly Val Pro Gly Asp Gly Asp Glu Glu Leu Leu Arg,
(5) Gly Val Pro Gly Asp Gly Asp Glu Glu Leu Leu,
(6) Gly Val Pro Gly Asp Gly Asp Glu Glu Leu,
(7) Gly Val Pro Gly Asp Gly Asp Glu Glu,
(8) Gly Val Pro Gly ASp Gly Asp Glu,
(9) Gly Val Pro Gly Asp Gly Asp,
(10) Gly Val Pro Gly ASp Gly,
(11) Gly Val Pro Gly Asp,
(12) Gly Val Pro Gly,
(13) Gly Val Pro,
(14) Gly Val, and
(15) Gly.

A derivative of each of the above amino acid sequences (1) to (15) may also be used as an amino acid sequence to be added to the C-terminus side, such as a derivative in which at least one amino acid in any of the amino acid sequences (1) to (15) is substituted by other optional amino acid, a derivative in which at least one optional amino acid is added to or deleted from any of the amino acid sequences (1) to (15) or a derivative in which such substitution, addition and deletion are effected simultaneously in any of the amino acid sequences (1) to (15). These sequences are useful when the novel polypeptide is produced using an *Escherichia coli* strain.

It goes without saying that the above-mentioned preferred amino acid sequences may be added to each N-terminus, C-terminus or both termini of N- and C-termini.

Most preferred examples of the amino acid sequence of the novel polypeptide of the first aspect of the present invention are shown in the SEQUENCE LISTING attached hereto as amino acids 1–68 or 1–70 of Sequence ID Nos. 2, 4, 6, 8, 10, 12, 14, 16, 35, 36, 37, 38, 39, 40, 41, 42 and 43.

The novel polypeptide according to the first aspect of the present invention may have a sugar chain.

Recent advances in the technology have rendered possible application of various chemical modifications polypeptides, such as alkylation, oxidation, reduction, hydrolysis and the like. Also, formation of a salt with a pharmacologically acceptable acid or base and linkage of polyethylene glycol or the like to a polypeptide from a drug delivery system (DDS) point of view are usually used techniques. In consequence, polypeptides to which such modifications are applied are also included in the novel polypeptide of the present invention.

Preferably, the novel polypeptide of the first aspect of the present invention may have at least a protease inhibition activity as one of its characteristic properties. The protease inhibition activity may preferably be inhibition of at least one of FXa, elastase and trypsin.

The novel polypeptide according to the first aspect of the present invention may be obtained by any means. For instance, it may be obtained by chemical synthesis using a peptide synthesizer (for example, model 431 manufactured by Applied Biosystems). It may be obtained also by known recombinant DNA techniques disclosed for instance by T. Maniatis et al. in *Molecular Cloning, a laboratory manual* (Cold Spring Harbor Laboratory, 1982), using a DNA fragment which encodes the novel polypeptide of the present invention. A preferred example of the production of the novel polypeptide of the present invention by means of recombinant DNA techniques will be described later in relation to the sixth and seventh aspect of the present invention.

Next, the novel DNA fragment of the second aspect of the present invention is described.

The novel DNA fragment of the present invention contains, at least as a pare thereof, a nucleotide sequence which encodes the novel polypeptide of the first aspect of the present invention. In other words, the novel DNA fragment of the present invention is characterized in that it comprises a nucleotide sequence which encodes a polypeptide that contains, at least as a part thereof, an amino acid sequence resulting from substitution of a different amino acid for at lease one amino acid in the aforementioned amino acid sequence of formula 1.

The phrase "a DNA fragment containing a nucleotide sequence as a part thereof" as used herein means that the DNA fragment may be defined either by the nucleotide sequence itself or by a nucleotide sequence in which the 5' end, the 3' end or both ends of the former nucleotide sequence is or are supplemented with one or more optional nucleotides. The novel DNA fragment of the present invention may have any nucleotide sequence, provided that the novel polypeptide of the first aspect of the present invention is produced in appropriate hose cells which have been transformed with the DNA fragment by an appropriate means. Since it is well known that multiple codons exist corresponding to one amino acid (for most amino acids), the nucleotide sequence which encodes the novel polypeptide of the first aspect of the present invention is not limited to a single sequence and, therefore, the nucleotide sequence of the novel DNA fragment of the present invention is also not limited to a single sequence. However, a nucleotide sequence which encodes the aforementioned amino acid sequence of formula 1 may preferably have the following formula 2.

Preferably, the novel DNA fragment of the present invention is a DNA fragment contains, at least as a part thereof, a nucleotide sequence in which one or more nucleotides in the nucleotide sequence of the above formula 2 are substituted by other nucleotides selected from adenine (A), guanine (G), thymidine (T) and cytosine (C).

When the amino acid sequence of the polypeptide of the first aspect of the present invention is taken into consideration, it is preferable to effect the nucleotide substitution in the aforementioned formula 2 at a 19 to 21 position nucleotide sequence, at a 43 to 45 position nucleotide sequence or at a 124 to 126 position nucleotide sequence, counting from the 5' end of the formula 2 nucleotide sequence. In other words, in the nucleotide sequence which is contained at least as a part of the novel DNA fragment the second aspect of the present invention, the nucleotide substitution by other nucleotides may be effected only at a 19 to 21 position nucleotide sequence CGG, at a 43 to 45 position nucleotide sequence CAG or at a 124 to 126 position nucleotide sequence TAC, counting from the 5' end of the nucleotide sequence of formula 2. Also, the nucleotide substitution may be effected by other nucleotides at least two of these positions. In addition to these nucleotide sequence substitutions, one or more other nucleotides at different positions may be substituted by optional nucleotides.

The aforementioned 19 to 21 position nucleotide sequence CGG which encodes Arg may be substituted by an optional nucleotide sequence, preferably by a nucleotide sequence that encodes Glu, Gln, Asp, Leu, Asn, Ser or Ala. The 43 to 45 position nucleotide sequence CAG which encodes Gln may be substituted by an optional nucleotide sequence, preferably by a nucleotide sequence that encodes Lys or Arg. The 124 to 126 position nucleotide sequence TAC which encodes Tyr may be substituted by an optional nucleotide sequence, preferably by a nucleotide sequence that encodes Glu or Asp.

More preferably, the novel DNA fragment of the second aspect of the present invention may contain, at least as a part thereof, a derivative of the nucleotide sequence of formula 2 resulting from at least one substitution selected from the following substitutions (1) to (11);

(1) substitution of AAG for the 43 to 45 position nucleotide sequence CAG counting from the 5' end,
(2) substitution of CGT for the 43 to 45 position nucleotide sequence CAG counting from the 5' end,
(3) substitution of GAA for the 124 to 126 position nucleotide sequence TAC counting from the 5' end,

| Formula 2 | | | | | | | | | |
|---|---|---|---|---|---|---|---|---|---|
| 1 | | | 10 | | | 20 | | | 30 |
| TGC | AAT | CTC | CCC | ATA | GTC | CGG | GGC | CCC | TGC |
| | | | 40 | | | 50 | | | 60 |
| CGA | GCC | TTC | ATC | CAG | CTC | TGG | GCA | TTT | GAT |
| | | | 70 | | | 80 | | | 90 |
| GCT | GTC | AAG | GGG | AAG | TGC | GTC | CTC | TTC | CCC |
| | | | 100 | | | 110 | | | 120 |
| TAC | GGG | GGC | TGC | CAG | GGC | AAC | GGG | AAC | AAG |
| | | | 130 | | | 140 | | | 150 |
| TTC | TAC | TCA | GAG | AAG | GAG | TGC | AGA | GAG | TAC |
| TGC | | | | | | | | | |
| (SEQ. I.D. NO.: 66) | | | | | | | | | |

(4) substitution of GAC for the 124 to 126 position nucleotide sequence TAC counting from the 5' end,
(5) substitution of GAA for the 19 to 21 position nucleotide sequence CGG counting from the 5' end, (6) substitution of CAG for the 19 to 21 position nucleotide sequence CGG counting from the 5' end,
(7) substitution of GAT for the 19 to 21 position nucleotide sequence CGG counting from the 5' end,
(8) substitution of CTG for the 19 to 21 position nucleotide sequence CGG counting from the 5' end,
(9) substitution of AAC for the 19 to 21 position nucleotide sequence CGG counting from the 5' end,
(10) substitution of AGC for the 19 to 21 position nucleotide sequence CGG counting from the 5' end, and
(11) substitution of GCG for the 19 to 21 position nucleotide sequence CGG counting from the 5' end.

The DNA fragment of the present invention may contain, at least as a part thereof, a nucleotide sequence in which one or more optional nucleotides are added to its 5' end, 3' end or both ends of the nucleotide sequence resulting from the substitution of at least one nucleotide in the nucleotide sequence of formula 2. The kinds and numbers of the nucleotides to be added are not limited, provided that the finally obtained DNA fragment contains a nucleotide sequence which encodes the polypeptide of the first aspect of the present invention. For example, the 5' end may be supplemented with an initiation codon, a promoter, a ribosome binding region, a signal peptide-encoding sequence or the like, and the 3' end may be supplemented with a termination codon. In addition, a nucleotide sequence which is recognized by an appropriate restriction enzyme may be added to the 5' end and/or the 3' end, or a nucleotide sequence which encodes other polypeptides may be added to the 5' end and/or the 3' end with the aim of producing the novel polypeptide of the first aspect of the present invention in the form of a fused protein with another polypeptide.

Preferred examples of the nucleotide sequence to be added to the 5' end include those which encode the amino acid sequences described as "preferred amino acid sequences to be added to the N-terminus" in the foregoing description about the polypeptide of the first aspect of the present invention, or which encode derivatives of these amino acid sequences resulting from deletion, addition, substitution and the like of one or more amino acids. Any nucleotide sequence which encodes such an amino acid sequence may be added to the 5' end as a preferred example, but a more preferred example may be selected from the following sequences (1) to (5).
(1) GAC GAC GCC GCC (SEQ. I.D. NO:68)
(2) ACC GTC GCC GCC (SEQ. I.D. NO:70)
(3) GTC GCC GCC
(4) GCC GCC
(5) GCC Preferred examples of the nucleotide sequence to be added to the 3' end include those which encode the amino acid sequences described as "preferred amino acid sequences to be added to the C-terminus" in the foregoing description about the polypeptide of the first aspect of the present invention, or which encode derivatives of these amino acid sequences resulting from deletion, addition, substitution and the like of one or more amino acids. Any nucleotide sequence which encodes such an amino acid sequence may be added to the 3' end as a preferred example, but a more preferred illustrative example may be selected from the following sequences (1) to (15);
(1) GGT GTC CCT GGT GAT GGT GAT GAG GAG CTG CTG CGC TTC TCC AAC (SEQ. I.D. NO:72),
(2) GGT GTC CCT GGT GAT GGT GAT GAG GAG CTG CTG CGC TTC TCC,
(3) GGT GTC CCT GGT GAT GGT GAT GAG GAG CTG CTG CGC TTC,
(4) GGT GTC CCT GGT GAT GGT GAT GAG GAG CTG CTG CGC,
(5) GGT GTC CCT GGT GAT GGT GAT GAG GAG CTG CTG,
(6) GGT GTC CCT GGT GAT GGT GAT GAG GAG CTG,
(7) GGT GTC CCT GGT GAT GGT GAT GAG GAG,
(8) GGT GTC CCT GGT GAT GGT GAT GAG,
(9) GGT GTC CCT GGT GAT GGT GAT,
(10) GGT GTC CCT GGT GAT GGT,
(11) GGT GTC CCT GGT GAT,
(12) GGT GTC CCT GGT,
(13) GGT GTC CCT,
(14) GGT GTC, and
(15) GGT.

It goes without saying that the above-mentioned preferred DNA sequences may be added to each 5' end, 3' end or both ends of 5' and 3' ends.

Most preferred examples of the nucleotide sequence of the novel DNA fragment of the second aspect of the present invention are shown in the SEQUENCE LISTING attached hereto as Sequence ID Nos. 1, 3, 5, 7, 9, 11, 13, 15, 17, 19, 21, 23, 25, 27, 29, 31 and 33.

The novel DNA fragment of the present invention may be obtained by any means. For instance, it may be obtained by chemical synthesis or by recombinant DNA techniques. Chemical synthesis of the novel DNA fragment of the present invention may be effected, for example, in the following manner. First, a desired nucleotide sequence is designed and the thus designed DNA fragment is divided into appropriately sized small fragments. An oligomer which corresponds to each of the thus divided fragments is synthesized using an fully automatic DNA synthesizer (for example, model 394 manufactured by Applied Biosystems). The thus synthesized oligomer is subjected to annealing. If necessary, 5'-end phosphorylation is carried out using T4 polynucleotide kinase prior to the annealing step. Thereafter, the thus annealed fragments are subjected, if necessary, to ligation with T4 DNA ligase, and then cloned into an appropriate vector.

When the novel DNA fragment of the present invention is prepared by means of recombinant DNA techniques, it may be obtained by nucleotide sequence modification and DNA amplification making use of an appropriate cDNA library, a chromosomal DNA library or a DNA fragment which encodes the amino acid sequence of formula 1, in accordance with usually used techniques such as site-directed mutagenesis (Kramer, W. et al., *Nucleic Acid Res.*, vol. 12, pp. 9441–9456, 1984; Kunkel, T. A. et al., *Methods in Enzymology*, vol. 154, pp. 357–382, 1987) and polymerase chain reaction (to be referred to as "PCR" hereinafter) (*PCR Protocols, A Guide to Methods and Applications*, edited by Michael, A. I. et al., Academic Press, 1990).

A cDNA library or a chromosomal DNA library to be used may be chosen from commercially available articles, or prepared from appropriate tissues or cells according to usually used means (cf. *Molecular Cloning, A Laboratory Manual*, edited by T. Maniatis et al., Cold Spring Harbor Laboratory, 1982). A DNA fragment which encodes the amino acid sequence of formula 1 may be obtained not only by chemical synthesis but also from an appropriate DNA library optionally making use of known recombinant DNA techniques such as hybridization (cf. Wallace, R. B. et al., *Nucleic Acid Res.*, vol. 9, pp. 879–894, 1981).

On the basis of the disclosure of the novel DNA fragment of the present invention, its complementary DNA fragments and RNA fragments can also be obtained. The DNA fragment of the present invention may also include sequences linked to such a complementary DNA or RNA fragment.

According to the third aspect of the present invention, there is provided a vector which contains the novel DNA fragment of the second aspect of the present invention.

in addition to the DNA fragment of the second aspect of the present invention, the vector of the present invention may further contain additional nucleotide sequences such as a promoter, a ribosome binding region, a signal peptide-encoding sequence, a selection marker sequence and the like, as well as a sequence which is used to amplify copy numbers of the DNA of interest. The vector of the present invention may be used for any purpose. For example, it may be used as an expression vector or as a cloning vector.

Vectors for expression use generally have a promoter, an optional ribosome binding region and other such sequences which are necessary for expression of genes. In the vector of the present invention, these necessary sequences are used by selecting them in such a way that they can function in host cells to be transformed with the vector. When a polypeptide expressed in the cells of a transformant is secreted outside the cells, a vector may generally contain a nucleotide sequence which encodes a signal peptide in addition to the above necessary sequences. In consequence, when the vector of the third aspect of the present invention is used as an expression vector, it may contain not only the DNA fragment of the second aspect of the present invention but also those nucleotide sequences necessary for expression and, if required, a nucleotide sequence which encodes a signal peptide.

The vector of the third aspect of the present invention may be obtained by inserting the DNA fragment of the second aspect of the present invention into an appropriate commercially available or known vector in accordance with usually used means (cf. *Molecular Cloning, A Laboratory Manual*, edited by T. Maniatis et al., Cold Spring Harbor Laboratory, 1982). The origin of the vector to be used for the insertion of the DNA fragment of the second aspect of the present invention is not particularly limited. Such a vector may be selected from various virus vectors, plasmid vectors, phage vectors and the like, such as pUC118, pBR322, pEFN-BOS, λgt10, pKK223-3, YAC, Baculo virus vector and the like. If necessary, optional nucleotide sequences such as a ribosome binding region, a selection marker sequence and the like may be synthesized chemically and inserted into the vector together with the DNA fragment of the second aspect of the present invention. Alternatively, the DNA fragment of the second aspect of the present invention may be inserted into a commercially available vector which already contains these desired nucleotide sequences.

A most preferred vector of the present invention is a plasmid vector which contains at least a tryptophan promoter, a kanamycin or ampicillin resistant gene and the DNA fragment of the second aspect of the present invention.

According to the fourth aspect of the present invention, there is provided a transformant transformed with the novel DNA fragment of the second aspect of the present invention. A transformant which can produce the novel polypeptide of the first aspect of the present invention is preferable as the transformant of the fourth aspect of the present invention. A transformant which either secrets the polypeptide outside the cell or which accumulates the polypeptide in the cell is preferable as the transformant of the fourth aspect of the present invention.

The transformant of the fourth aspect of the present invention may be obtained by introducing the novel DNA fragment of the second aspect of the present invention into appropriate host cells in accordance with a usually used means such as a calcium chloride technique, a method in which a calcium phosphate-DNA complex is used, a microinjection technique, electroporation or the like.

Preferably, in addition to a nucleotide sequence encoding the novel polypeptide of the first aspect of the present invention, the novel DNA fragment of the second aspect of the present invention to be used for the preparation of the transformant may contain additional nucleotide sequences which encode a promoter, a ribosome binding region and the like that are necessary for the expression of the novel polypeptide of the first aspect of the present invention. If necessary, the DNA fragment to be used may contain a nucleotide sequence which encodes a signal peptide in addition to other necessary nucleotide sequences for the expression of the polypeptide. These promoter, ribosome binding region, signal peptide-encoding sequences and the like may be of various origins, provided that they can function in the host cells to be used.

Host cells to be used for the insertion of the novel DNA fragment of the second aspect of the present invention are not strictly limited, provided that they are suitable for use in the expression of the novel polypeptide of the first aspect of the present invention. Such suitable host cells may be selected from either eukaryotic cells such as HeLa cells, Namalwa cells, COS cells, CHO cells, yeast cells, SF cells and the like or prokaryotic cells such as *E. coli* cells, *Bacillus subtilis* cells and the like.

According to the fifth aspect of the present invention, there is provided a transformant transformed with the vector of the third aspect of the present invention. A transformant which can produce the novel polypeptide of the present invention is preferable as the transformant of the fifth aspect of the present invention. A transformant which either secrets the polypeptide outside the cell or which accumulates the polypeptide in the cell is preferable as the transformant of the fifth aspect of the present invention.

The transformant of the fifth aspect of the present invention is obtained by transforming an appropriate host cells with the vector of the third aspect of the present invention by a usually used means such as a calcium chloride technique, a rubidium chloride technique, Hanahan's method (Hanahan, D., Techniques for Transformation of *E. coli*; in *DNA Cloning*, vol. 1, Glover, D. M. (ed.), pp. 109 . 136, IRL Press, 1985) or the like.

Host cells to be used for the transformation by the vector of the third aspect of the present invention are not strictly limited, provided that they are suitable for use in the expression of the novel polypeptide of the first aspect of the present invention. Such suitable hose cells may be selected from either eukaryotic cells such as HeLa cells, Namalwa cells, COS cells, CHO cells, yeast cells, SF cells and the like or prokaryotic cells such as *E. coli* cells, *B. subtilis* cells and the like.

As it is universally known, a host cell and a vector function mutually. Taking this into consideration, it is preferable to obtain the inventive transformant by selecting an appropriate origin of the vector, a nucleotide sequence necessary for expression in the vector and an appropriate host in such a combination that the novel polypeptide of the first aspect of the present invention can be expressed efficiently.

Illustrative examples of the combination of expression vector with host cells include: an expression vector containing the early promoter gene of simian virus 40 (SV40) with COS-7 cells; and an expression vector originated from plasmid pBR322 containing nucleotide sequences which encode a tryptophan promoter and a tryptophan SD sequence with *E. coli* HB101 cells.

As will be described later in Examples, the present inventors have prepared E. coli JE5505 transformants transformed with the vector of the third aspect of the present invention. These transformants have been deposited by the present inventors in the Patent Microorganisms Depositary Center of Fermentation Research Institute, Agency of Industrial Science and Technology (1-1-1, Higashi, Yatabecho, Tsukuba-gun, Ibaraki, Japan). The following shows deposition numbers and names of these transformants.

| Date deposited | Deposition No. | Name |
| --- | --- | --- |
| September 11, 1990 | FERM P-11726 | E. coli JE5505 (pM552) |
| September 10, 1991 | FERM BP-3561 (transferred from FERM P-11726) | |
| July 16, 1991 | FERM P-12357 | E. coli JE5505 (pM575B) |
| October 17, 1991 | FERM BP-3613 (transferred from FERM P-12357) | |
| July 16, 1991 | FERM P-12358 | E. coli JE5505 (pM576) |
| October 17, 1991 | FERM BP-3614 (transferred from FERM P-12358) | |
| May 1, 1992 | FERM P-12945 | E. coli JE5505 (pM735) |
| May 1, 1992 | FERM P-12946 | E. coli JE5505 (pM736) |
| October 21, 1992 | FERM BP-4041 | E. coli JE5505 (pM741) |

The following describes sixth and seventh aspects of the present invention, concerning processes suitable for the production of the novel polypeptide of the first aspect of the present invention, to which recombinant DNA techniques are applied.

According to the sixth aspect of the present invention, there is provided a process for the production of the novel polypeptide of the first aspect of the present invention which comprises the steps of:

a) preparing a DNA fragment containing a nucleotide sequence which encodes the novel polypeptide of the first aspect of the present invention, b) preparing a transformant by transforming host cells with the DNA fragment obtained in the above step a), and c) culturing the transformant obtained in the above step b) to allow the transformant to produce the novel polypeptide of the first aspect of the present invention and subsequently recovering said polypeptide from the cultured medium.

In the above step a), the phrase "a DNA fragment containing a nucleotide sequence which encodes the novel polypeptide of the first aspect of the present invention" preferably means a DNA fragment of the second aspect of the present invention Preferably this DNA fragment may further contain a nucleotide sequence which is necessary for the expression of the novel polypeptide of the first aspect of the present invention, in addition to a nucleotide sequence that encodes said novel polypeptide. If necessary, said DNA fragment may also contain a nucleotide sequence which encodes a signal peptide.

The transformant obtained in the above step b) belongs preferably to the transformant of the fourth aspect of the present invention, and it can therefore be obtained by the process described in the foregoing in relation to the fourth aspect of the present invention.

The thus obtained transformant in the above step b) is used in the subsequent step c). Culturing of the transformant may be effected by generally used means for the culturing of microorganisms or mammalian cells, in accordance with the procedure disclosed for instance in Seibutsu Kagaku Kogaku (or Biochemical Engineering; S. Aiba et al., 1976, Tokyo University Press) or in Soshiki Baiyo (or Tissue Culture; J. Nakai et al., 1976, Asakura Shoten).

Next, the novel polypeptide of the first aspect of the present invention thus produced by the transformant is recovered from the cultured medium of said transformant. In this instance, the thus produced novel polypeptide of the first aspect of the present invention may be isolated preferably from the cultured cells of the transformant when the product is not secreted extracellularly, or from culture supernatant when secreted into the medium. Purification and recovery of the novel polypeptide of the first aspect of the present invention from a cultured broth containing said polypeptide may be carried out in the light of various generally used means for the purification of polypeptides which have been disclosed in many reports and books such as Seikagaku Jikken Koza (or Biochemical Experiments; vol. I, Protein Chemistry, 1976, edited by The Japanese Biochemical Society, Tokyo Kagaku Dojin). When the polypeptide of the present invention forms an inclusion body inside the transformant cells, it is preferable to carry solubilization, denaturation and refolding in its purification (cf. Thomas E. Creighton, J. Mol. Biol., vol. 87, pp. 563–577, 1974).

Examples of protein purification techniques include ammonium sulfate precipitation, ultrafiltration, isoelectric precipitation, gel filtration, ion exchange chromatography, various affinity chromatographic techniques such as hydrophobic chromatography, antibody chromatography and the like, chromatofocusing, absorption chromatography and reverse phase chromatography. Consequently, recovery and purification of the novel polypeptide of the first aspect of the present invention may be carried out by selecting suitable ones from these techniques and, if necessary, making use of an HPLC system and the like, in appropriate order of the techniques.

According to the seventh aspect of the present invention, there is provided a process for the production of the novel polypeptide of the first aspect of the present invention which comprises the steps of:

a) preparing a DNA fragment containing a nucleotide sequence which encodes the novel polypeptide of the first aspect of the present invention, b) constructing a vector containing the DNA fragment obtained in the above step a)

c) preparing a transformant by transforming host cells with the vector obtained in the above step b), and d) culturing the transformant obtained in the above step c) to allow the transformant to produce the novel polypeptide of the first aspect of the present invention and subsequently recovering said polypeptide from the cultured medium.

In the above step a), the term "a DNA fragment containing a nucleotide sequence which encodes the novel polypeptide of the first aspect of the present invention" preferably means a DNA fragment of the second aspect of the present invention.

The vector obtained in the above step b) is preferably the vector of the third aspect of the present invention. More preferably, the vector obtained in the above step b) is a vector which further contains a nucleotide sequence necessary for the expression of the polypeptide of the first aspect of the present invention, in addition to a nucleotide sequence that encodes said polypeptide. If necessary, said vector may also contain a nucleotide sequence which encodes a signal peptide. A process for the construction of such a vector has already been described in the foregoing in relation to the third aspect of the present invention.

The transformant thus obtained in the above step c) belongs preferably to the transformant of the fifth aspect of the present invention, and it can therefore be obtained by the process described in the foregoing in relation to the fifth aspect of the present invention.

The thus obtained transformant in the above step c) is used in the subsequent step d). Processes for the culturing of the transformant and subsequent recovery and purification of the novel polypeptide of the present invention from the cultured medium are the same as those described in the foregoing in relation to the sixth aspect of the present invention.

Thus, processes for the production of the novel polypeptide have been described with respect to the sixth and seventh aspects of the present invention. In the practice of these processes, a DNA fragment which contains a fused nucleotide sequence consisting of a nucleotide sequence coding for the polypeptide of the first aspect of the present invention and another nucleotide sequence encoding another polypeptide (*E. coli*β-galactosidase for example) or a part thereof may be used as the DNA fragment that contains a nucleotide sequence encoding the novel polypeptide of the first aspect of the present invention. In such an instance, a transformant transformed with said DNA fragment or with a vector prepared therefrom will produce a fused polypeptide consisting of the novel polypeptide of the present invention and another polypeptide (*E. coli*62 -galactosidase for example). In that case, it is possible to obtain the novel polypeptide of the first aspect of the present invention by recovering said fused polypeptide and then treating it with appropriate chemical compounds, enzymes and the like to cue out and remove the additional polypeptide portion, followed by purification if necessary.

Next, the drug composition of the eighth aspect of the present invention is described.

The drug composition provided by the present invention contains the novel polypeptide of the first aspect of the present invention as an active ingredient. A single polypeptide or a plurality of polypeptides may be contained in the drug composition, provided that they belong to the novel polypeptide of the first aspect of the present invention.

Though it is possible to provide the medical field with a fully effective drug composition of the present invention even if the drug composition of the eighth aspect of the present invention is composed solely of the novel polypeptide of the first aspect of the present invention (for example, an article of the polypeptide processed through pharmaceutically necessary seeps such as lyophilizing, sterile filtration and the like), the drug composition may further contain pharmaceutically acceptable auxiliary components in a pharmaceutically acceptable amount.

Such auxiliary components to be included in the drug composition of the present invention are a base, a stabilizer, an antiseptic agent, a preservation agent, an emulsifying agent, a suspending agent, a solvent, a solubilizing agent, a lubricant, a corrective agent, a coloring agent, an aromatic agent, a soothing agent, an excipient, a binder, a thickening agent, a buffer and the like. Illustrative examples of these auxiliary components include calcium carbonate, lactose, sucrose, sorbitol, mannitol, starch, amylopectin, cellulose derivatives, gelatin, cacao butter, distilled water for injection use, sodium chloride solution, Ringer solution, glucose solution, human serum albumin (HSA) and the like. Of these components, gelatin and albumin are especially useful as protein stabilizers. The auxiliary components to be added to the drug composition of the present invention may be selected in the light of "A List of Pharmaceutical Additives" (published by the Committee on Pharmaceutical Affairs Law, Tokyo Drug Industry Association and the Committee on Pharmaceutical Affairs Law Research, Osaka Drug Association) and decided depending on the dosage form and the like of the drug composition.

Dosage forms of the drug composition of the present invention are not particularly limited and can be selected according to each application purpose from for example injections, tablets, capsules, pills, granules, suppositories, solutions, suspensions, emulsions, powders, ointments, creams, gels, cataplasmas, lotions and the like.

Dose of the drug composition of the present invention may vary depending on the content of active ingredient and conditions, age, sex, weight and the like of each patient to be treated. Preferably, however, the drug composition of the present invention may be administered in an amount of from 0.1 to 1,000 mg/kg, more preferably from 0.2 to 50 mg/kg, most preferably from 0.2 to 20 mg/kg, as the amount of the active agent. The drug composition of the present invention can be administered by various means depending on the conditions of each patient, such as oral administration, intramuscular injection, intraperitoneal injection, intradermal injection, subcutaneous injection, intravenous injection, intraarterial administration, rectal administration, vaginal administration and the like as well as airway inhalation of the drug composition making it into an aerosol dosage form, buccal dissolution, percutaneous absorption, mucosal absorption and the like, of which intravenous injection is particularly preferred.

Diseases and symptoms which may be prevented and/or treated by making use of the drug composition of the present invention include infestation, multiple organ failure, shock, pancreatitis, disseminated intravascular coagulation syndrome, ischemic heart disease, nephritis, hepatic cirrhosis, re-obstruction at the time of blood circulation reconstructive operation, edema caused by increased vascular permeability, adult respiratory distress syndrome, rheumatoid arthritis, arthritis, allergic diseases and the like.

Application of the drug composition of the present invention is not limited to the prevention and/or treatment of specific diseases. In can be used suitably as a blood coagulation inhibitor. Also, in addition to its direct administration to the body, the inventive drug composition can be used for the purpose of preventing blood coagulation, by binding and adsorbing it to the surface of medical devices such as artificial blood vessel, artificial organs, catheters and the like making use of a cross-linking agent and the like.

Next, the ninth aspect of the present invention is described.

The protease inhibition process of the ninth aspect of the present invention is characterized in that it uses the novel polypeptide of the first aspect of the present invention. More particularly, the ninth aspect of the present invention is a process for inhibiting the activity of a protease which comprises allowing the novel polypeptide of the first aspect of the present invention to react with said protease.

The protease to be inhibited in the protease inhibition process of the present invention is not particularly limited and may be a single protease or a plurality of proteases, provided that they are sensitive to the novel polypeptide of the first aspect of the present invention. However, at least one protease, especially trypsin, FXa, or elastase may be used preferably as the protease to be inhibited.

In the protease inhibition process of the present invention, a protease and the novel polypeptide of the first aspect of the present invention are allowed to react with each other under appropriate reaction conditions such as temperature, pH, time and the like, thereby effecting inhibition of the protease activity. The reaction may be carried out in a test tube or the like (in vitro) or in the body of an animal (in vivo, ex vivo).

If necessary, the reaction may be carried out in the presence of other substances, drugs and the like in addition to the novel polypeptide of the first aspect of the present invention. The novel polypeptide to be applied to the enzyme inhibition process of the present invention may be used in the form of a composition containing auxiliary components and the like.

EXAMPLES

Examples of the present invention are given below by way of illustration and not by way of limitation. Abbreviations used herein are based on idiomatic expressions. Experiments were carried out in the light of the following reports and books.

1. *Labo Manual Genetic Engineering*; M. Muramatsu, 1989, Maruzen
2. *Gene Manipulation Techniques*; Y. Takagi, 1980, Kodansha
3. *Gene Manipulation Manual*; Y. Takagi, 1980, Kodansha
4. *Molecular Cloning, A Laboratory Manual*; T. Maniatis et al., 1982, Cold Spring Harbor Laboratory
5. *Methods in Enzymology*; vol. 65, L. Grossman, 1980, Academic Press
6. *Methods in Enzymology*; vol. 68, R. Wu, 1979, Academic Press
7. *PCR Protocols, A Guide to Methods and Applications*; Michadel, A. I. et al., 1990, Academic Press
8. *Molecular Cloning, A Laboratory Manual* (second edition); T. Maniatis et al., 1989, Cold Spring Harbor Laboratory Example 1

Construction of plasmid pM469

Plasmid pM469 to be used later in Example 2 as an expression vector was prepared from plasmid pM463 by the following method. Plasmid pM463 used herein as the starting material is a derivative of plasmid pBR322, which contains a nucleotide sequence for the replication in *E. coli* cells, an ampicillin resistance gene, a tryptophan promoter, a nucleotide sequence coding for an alkaline phosphatase signal peptide and a nucleotide sequence encoding a human pancreatic secretion trypsin inhibitor (to be referred to as "PSTI" hereinafter) (Kanamori, T. et al., *Gene*, vol. 66, pp. 295—300, 1988).

First, plasmid pM463 was double-digested with restriction endonucleases HindIII and NruI and the resulting mixture of DNA fragments was electrophorsed on a 0.7% agarose gel. A DNA fragment of about 3.4 kb thus isolated by the electrophoresis was absorbed to diethylaminoethyl cellulose paper (to be referred to as "DEAE cellulose paper" hereinafter) and then extracted with a high concentration salt solution (2M NaCl/10 mM Tris-HCl buffer (pH 7.5)/1 mM EDTA) to recover the DNA fragment of about 3.4 kb.

Separately from this, a linker consisting of an SD sequence, a nucleotide sequence encoding an *E. coli* alkaline phosphatase signal peptide and a nucleotide sequence encoding a part of N-terminal side amino acid sequence of PSTI was divided into six designed fragments (FIG. 1, SEQ. I.D. NOS.:44–49). Each of the thus designed fragments was synthesized using a chemical synthesizer (381A, Applied Biosystems, Inc.) (cf. FIG. 1). Of these 6 fragments thus synthesized, S34, S35, S18 and S19 were subjected to 5'-end phosphorylation with T4 polynucleotide kinase (Takara Shuzo Co., Ltd.) in the presence of ATP. Subsequently, each of the combinations of S33 with phosphorylated S34, phosphorylated S35 with phosphorylated S18 and phosphorylated S19 with S20 was subjected to annealing, followed by their ligation making use of a DNA ligation kit (Takara Shuzo Co., Ltd.). The thus ligated sample was then electrophoresed on a 8% polyacrylamide gel to separate and extract a DNA fragment (linker 1) of about 100 bp which was subsequently purified by phenol treatment and ethanol precipitation. The thus obtained DNA fragment of about 100 bp and the aforementioned DNA fragment of about 3.4 kb were ligated, and *E. coli* HB101 was transformed with the thus ligated product to isolate an ampicillin-resistant colony as a transformant of interest. Plasmid DNA was prepared from the thus obtained transformant and named plasmid pM468 (cf. FIG. 2).

Figure 3:
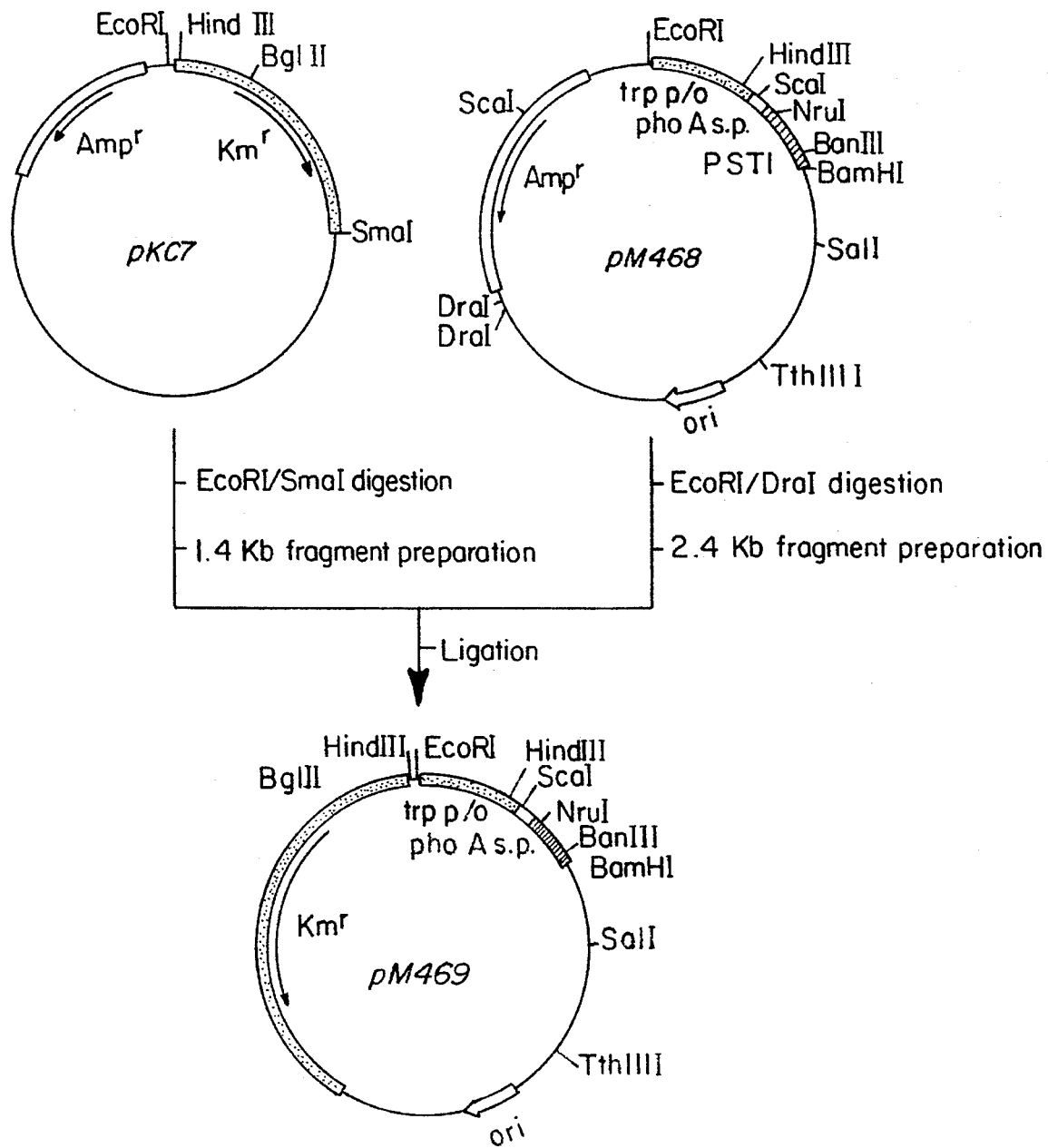
FIG. 3 is a schematic for a process for the construction of plasmid pM469.

The thus obtained plasmid pM468 was double-digested with EcoRI and DraI, and a DNA fragment of about 2.4 kb was isolated and recovered using DEAE cellulose paper in the same manner as described above. Separately from this, plasmid pKC7 containing a kanamycin resistance gene ($km^r$) (Ngarajarao, R. et al., *Gene*, vol. 7, pp. 79–82, 1979) was double-digested with restriction endonucleases EcoRi and SmaI to prepare a DNA fragment of about 1.4 kb containing the kanamycin resistance gene. The thus obtained DNA fragment of about 1.4 kb and the aforementioned DNA fragment of about 2.4 kb were ligated, and *E. coli* HB101 was transformed with the thus ligated product to isolate a kanamycin-resistant colony as a transformant of interest. Plasmid DNA was prepared from the thus obtained transformant and named plasmid pM469 (cf. FIG. 3).

Example 2

Production of polypeptide Y46E

A polypeptide, Y46E, having an amino acid sequence derived from the aforementioned formula 1 amino acid sequence by substituting Glu for the 42 position Tyr of the formula 1 sequence counting from its N-terminus was prepared in the following manner.

(1) Cloning of DNA fragment

Figure 4:
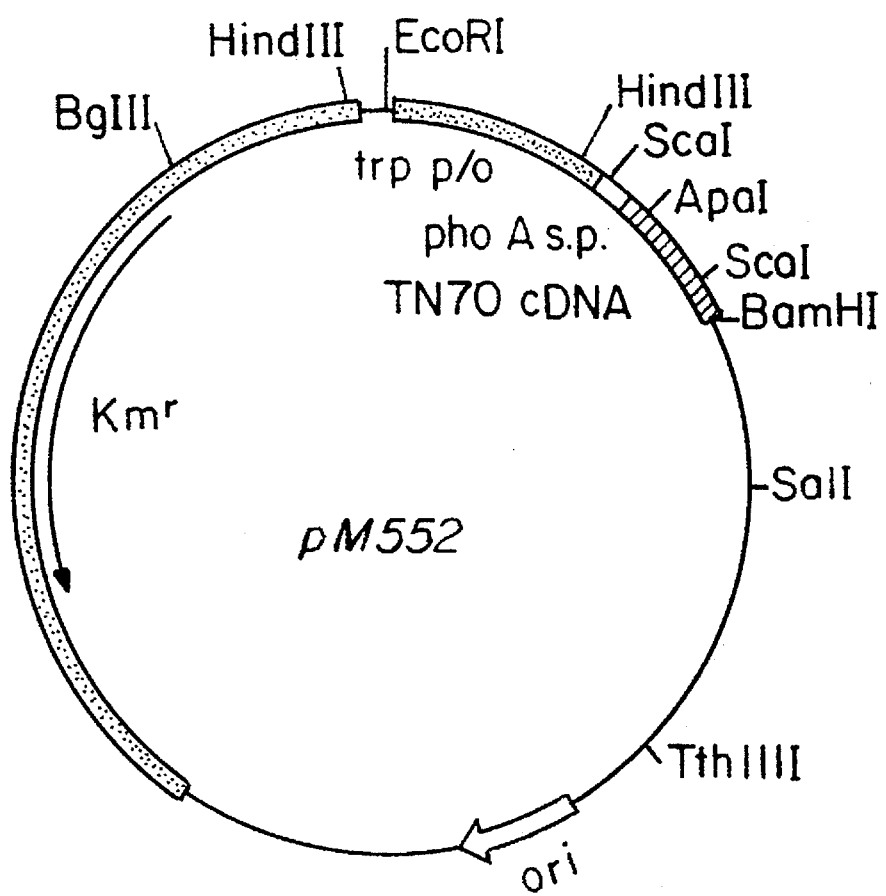
FIG. 4 is a map plasmid pM552.

A DNA fragment encoding the polypeptide Y46E was prepared by means of site-directed mutagenesis (cf. Kunkel, T. A. et al., *Methods in Enzymology*, vol. 154, p. 367, 1987) using plasmid pM552 (cf. Japanese Patent Application No. 3-325220). The pM552 is a plasmid which has been constructed by inserting into plasmid pM469 a nucleotide sequence that encodes a polypeptide TN70 represented by the following amino acid sequence of formula 3, that is, a DNA fragment (TN70 DNA) represented by the following nucleotide sequence of formula 4. The plasmid pM552 contains a tryptophan promoter, a nucleotide sequence coding for an alkaline phosphatase signal peptide and a kanamycin resistance gene (cf. FIG. 4).

| Formula 3 (SEQ. I.D. NO.: 75) | | | | | | | | | |
|---|---|---|---|---|---|---|---|---|---|
| Thr | Val | Ala | Ala | Cys | Asn | Leu | Pro | Ile | Val |
| Arg | Gly | Pro | Cys | Arg | Ala | Phe | Ile | Gln | Leu |
| Trp | Ala | Phe | Asp | Ala | Val | Lys | Gly | Lys | Cys |
| Val | Leu | Phe | Pro | Tyr | Gly | Gly | Cys | Gln | Gly |
| Asn | Gly | Asn | Lys | Phe | Tyr | Ser | Glu | Lys | Glu |
| Cys | Arg | Glu | Tyr | Cys | Gly | Val | Pro | Gly | Asp |

-continued

| Gly | Asp | Glu | Glu | Leu | Leu | Arg | Phe | Ser | Asn |
|-----|-----|-----|-----|-----|-----|-----|-----|-----|-----|
| | | | | Formula 4 (SEQ. I.D. NO.: 74) | | | | | |
| ACC | GTC | GCC | GCC | TGC | AAT | CTC | CCC | ATA | GTC |
| CGG | GGC | CCC | TGC | CGA | GCC | TTC | ATC | CAG | CTC |
| TGG | GCA | TTT | GAT | GCT | CTC | AAG | GGG | AAG | TGC |
| GTC | CTC | TTC | CCC | TAC | GGG | GGC | TGC | CAG | GGC |
| AAC | GGG | AAC | AAG | TTC | TAC | TCA | GAG | AAG | GAG |
| TGC | AGA | GAG | TAC | TGC | GGT | GTC | CCT | GGT | GAT |
| GGT | GAT | GAG | GAG | CTG | CTG | CGC | TTC | TCC | AAC |

First, plasmid pM552 was double-digested with HindIII and BamHI, and the thus digested fragments were subjected to 1% agarose gel electrophoresis. A DNA fragment of about 310 bp containing the nucleotide sequence of formula 4 was extracted from the agarose gel and then purified by means of phenol treatment and ethanol precipitation. Using T4 DNA ligase (already described in the foregoing), the thus obtained DNA fragment of about 310 bp was ligated with a phage vector M13mp18 which has been double-digested with HindIII and BamHI in advance. Thereafter, the thus ligated product was transfected into E. coli JM109 cells (transfection) to obtain M13 phage.

Next, site-directed mutagenesis was carried out making use of a Mutan™-K kit (Takara Shuzo Co., Ltd. ) and according to the manufacturer's instructions. That is, an E. coli strain BW313 (HfrKL16PO/45 [lysA(61–62)], dutl, ung1, thi-1, relA1) provided with the kit as an indicator strain was infected with the M13 phage to obtain phage plaques. A single plaque was inoculated into 2×YT medium using the BW313 as an indicator strain and cultured at 37° C. for 6 hours. Thereafter, single stranded DNA (ssDNA) was extracted and purified from the resulting phage culture broth by means of phenol treatment and ethanol precipitation. Separately from this, Y46E primer (FIG. 5, SEQ. I.D. NO.:50) for mutagenesis use was synthesized using the aforementioned chemical synthesizer and purified using an OPC column (Applied Biosystems, Inc.), and the 5'-end of the thus purified oligomer Y46E was phosphorylated using T4 polynucleotide kinase and ATP. The thus phosphorylated oligomer was subjected to annealing with the just obtained ssDNA by incubating them at 65° C. for 15 minutes and then at 37° C. for 15 minutes. The resulting reaction mixture was then incubated at 25° C. for 2 hours in the presence of E. coli DNA ligase and T4 DNA polymerase provided with the Mutan™-K kit to synthesize a complementary chain. After terminating the reaction with EDTA, the resulting complementary chain was transfected into E. coli BMH 71–18 (mutS (Δ(lac-proAB), thi, supE, mutS215::Tn10(tet$^r$)/F' traD36, proAB lacI$^q$, lacZΔM15)) provided with the kit, and phage plaques were obtained using JM109 as an indicator strain. Phage particles were recovered from each single plaque thus obtained and cultured using JM109 as an indicator strain to obtain a phage solution from which ssDNA was extracted and purified by means of phenol treatment and ethanol precipitation. Thereafter, the nucleotide sequence of each ssDNA sample was determined using a DNA sequencer (370A, Applied Biosystems, Inc.) to select an ssDNA sample into which the desired mutation had been introduced.

Next, PCR was carried out in the following method, using the thus obtained ssDNA as a template. That is, a ScaI primer (FIG. 6, SEQ. I.D. NO.:51) to be used as a sense primer and a BamHI primer (FIG. 7, SEQ. I.D. NO.:52) to be used as an antisense primer were synthesized using the aforementioned chemical synthesizer and then purified using the aforementioned OPC column. The thus obtained ScaI sense primer and BamHI antisense primer were added to a 100 μl solution containing the aforementioned ssDNA, and the resulting mixture was subjected to the PCR reaction using Gene Amp® PCR Reagent Kit (Takara Shuzo Co., Ltd.) by repeating 30 cycles of the reaction. In this instance, each reaction cycle was effected by a series of incubation at 94° C. for 1 minute, 55° C. for 2 minutes and 72° C. for 3 minutes in that order. Thereafter, the DNA fragment of the present invention was purified from the resulting reaction mixture by means of phenol treatment and ethanol precipitation.

(2) Construction of expression vector

Figure 8:
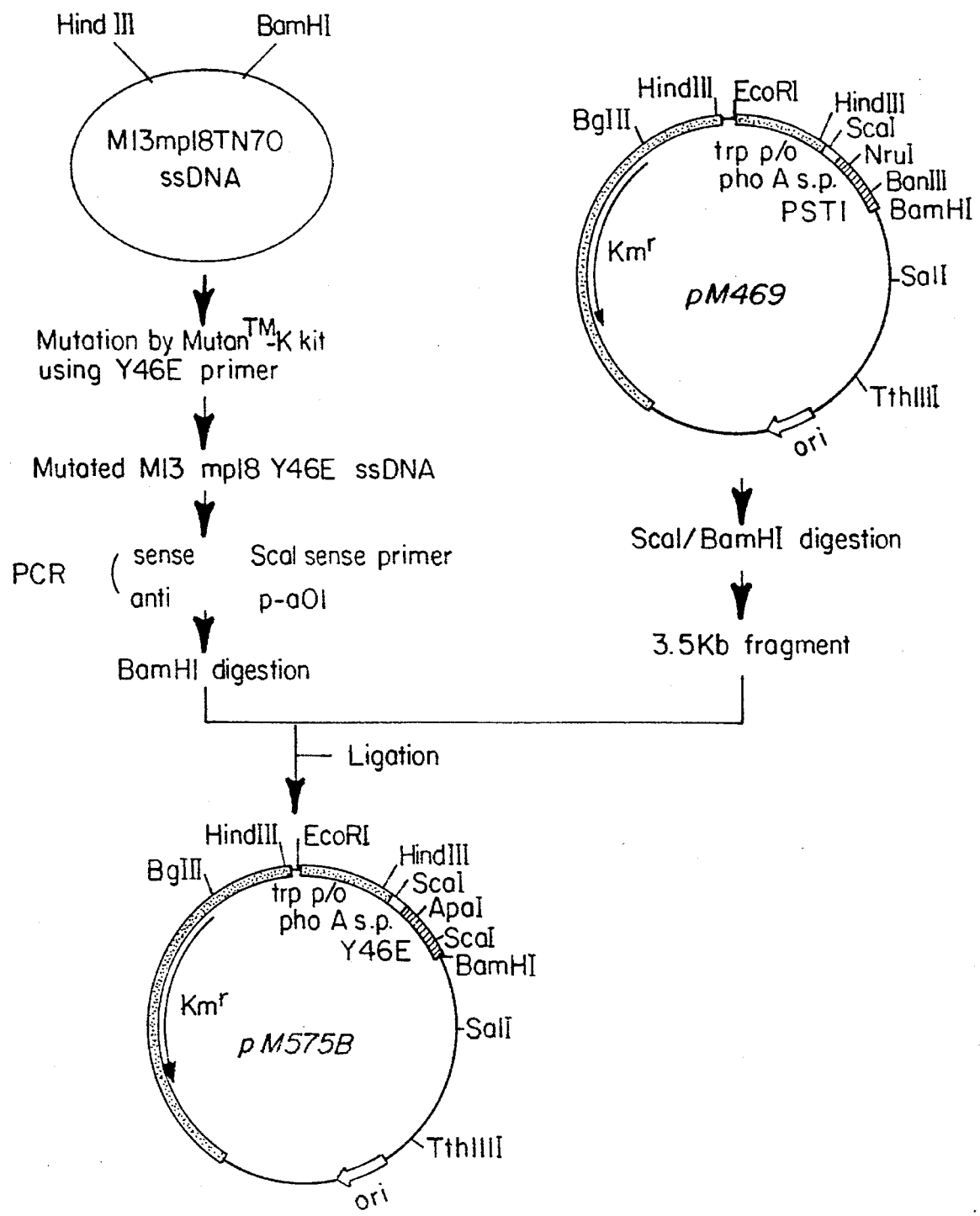
FIG. 8 is a schematic of a process for the construction of plasmid pM575B.

Plasmid pM469 obtained in Example 1 was double-digested with ScaI and BamHI, and the resulting DNA fragments were subjected to 0.7% low melting agarose gel electrophoresis. A DNA fragment of about 3.5 kb was purified from the agarose gel by cutting out a gel portion containing the fragment, melting the cut out gel portion at 65° C. and then treating the resulting solution with phenol, followed by ethanol precipitation. Next, the DNA fragment of the present invention obtained in the above procedure (1) was digested with BamHI and then ligated with the just obtained DNA fragment of about 3.5 kb to obtain an expression plasmid pM575B (cf. FIG. 8).

The thus obtained plasmid pM575B was double-digested with HindIII and BamHI, and a DNA fragment of interest having a size of about 310 bp was extracted and purified by means of phenol treatment and ethanol precipitation. The thus purified DNA fragment was ligated with each of the phage vectors M13mp18 and M13mp19 (Takara Shuzo Co., Ltd.) which have been double-digested with HindIII and BamHI in advance, and each of the ligated products was transfected into E. coli JM109 to form plaques. Thereafter, ssDNA was prepared from each of the resulting plaques and subjected to sequencing using a DNA sequencer (370A, Applied Biosystems, Inc.). The thus confirmed nucleotide sequence of a region of plasmid pM575B from its HindIII site to its BamHI site containing the DNA fragment of interest and its corresponding amino acid sequence are shown in FIG. 9 (see SEQ. I.D. NO.:1 in the SEQUENCE LISTING).

(3) Preparation and culturing of transformant

A transformant, E. coli JE5505 (pM575B), was prepared by transforming E. coli JE5505 with the plasmid pM575B obtained in the above procedure (2) in accordance with the Hanahan's method (Hanahan D., Techniques for Transformation of E. coli; in DNA Cloning, vol. 1, Glover, D .M. (ed.) , pp. 109–136, IRL Press, 1985). The thus prepared transformant, E. coli JE5505 (pM575B), was cultured at 37° C. for about 8 hours in L-broth containing 50 μ/ml of kanamycin (first seed culture). The resulting culture broth was inoculated in about 100 volumes of the same medium and cultured overnight at 37° C. (second seed culture). The main culture was then carried out by inoculating the resulting culture broth in 50 volumes of M9CA medium containing 50 μg/ml of kanamycin and culturing at 37° C. for about 1 hour. After adding 3-β-indole acrylic acid (Wako Pure Chemical Industries, Ltd.) to a final concentration of 10 μg/ml, the culturing was continued for additional 16 hours. Thereafter, culture filtrate was obtained from the resulting culture broth by centrifugation.

The culture filtrate thus prepared was diluted with 0.1% BSA (bovine serum albumin)/0.2M triethanolamine-HCl buffer (pH 7.8) to each predetermined concentration, and the diluted samples were used for the measurement of trypsin-inhibiting activity in accordance with the procedure described in Example 17 (1). In this instance, culture filtrate of a transformant, E. coli JE5505 (pM553), was used as a control in the activity measurement, which has been obtained by deleting the aforementioned nucleotide sequence of formula 4 from plasmid pM552 to obtain a plasmid pM553 and by transforming E. coli JE5505 with the thus obtained plasmid pM553.

Markedly high trypsin-inhibiting activity was found in the culture filtrate of E. coli JE5505 (pM575B) in comparison with the control. The transformant E. coli JE5505 (pM575B) has been deposited by the present inventors on Jul. 16, 1991, in the Fermentation Research Institute, Agency of Industrial Science and Technology, and has been assigned the designation FERM P-12357 which was subsequently transferred to the International Depositary Authority on Oct. 17, 1991, as FERM BP-3613.

(4) Purification of inventive polypeptide from culture supernatant of E. coli JE5505 (pM575B)

The novel polypeptide of the present invention was recovered and purified from culture supernatant of the transformant E. coil JE5505 (pM575B) obtained in the above procedure (3) by the following method.

(a) Ammonium Sulfate Precipitation

Ammonium sulfate was added to one liter of the culture supernatant to a level of 80% saturation. The mixture was stirred until ammonium sulfate was completely dissolved and then the solution was allowed to stand overnight at 4° C. The sample was cetrifuged at 12,000×g for 30 minutes at 4° C., and the thus obtained pellet was dissolved in 25 ml of distilled water. After removing the insoluble precipitate by centrifugation, the supernatant was concentrated to 1 ml using an ultrafiltration membrane (molecular weight cutoff of 1,000; Diaflow membrane YM-1, Grace Company). Thereafter, the thus concentrated sample was centrifuged at 5,860×g for 10 minutes at 4° C. to recover supernatant.

(b) Gel filtration

The concentrated sample obtained in the above step (a) was applied to a column (1 cmø×115 cm) packed with Sephadex G-50 (Pharmacia) which had been equilibrated with PBS⁻ (phosphate buffered saline). The loaded sample was eluted with PBS⁻ at a flow rate of 0.2 ml/min to obtain 2 ml fractions.

A portion of each fraction was collected and checked for its trypsin-inhibiting activity in accordance with the procedure described in Example 17 (1). Thereafter, active fractions were pooled and dialyzed overnight at 4° C. against 20 mM Tris-HCl buffer (pH 8.5) using a dialysis membrane (molecular weight cutoff of 1,000; Spectrum Medical Industries, Inc.).

(c) Anion exchange chromatography

Anion exchange chromatography was carried out using an FPLC system (Pharmacia) using the following method. The dialyzed sample obtained in the above step (b) was applied to Mono Q column (5 mmø×50 mm, Pharmacia) which had been equilibrated with 20 mM Tris-HCl (pH 8.5). Elution was carried out at a flow rate of 1 ml/min with a linear gradient of 0 to 0.4M NaCl/20 mM Tris-HCl (pH 8.5)/48 min. Protein concentration in the eluent was monitored by absorbance an 280 nm and each protein peak was collected. A portion of each collected fraction was checked for its trypsin-inhibiting activity in accordance with the procedure described in Example 17 (1) and active fractions were pooled.

(d) Reverse phase chromatography

The active fraction pooled in the above sled (c) was applied to a Vydac C18 column (4.6 mmø×25.0 cm, The Separations Group) which had been equilibrated with 0.04% trifluoroacetic acid solution. Using a Waters 625 LC system (Waters Associates, Inc.), elution was carried out at a flow rate of 1 ml/min with a linear density gradient of 0 to 100% acetonitrile/0.04% trifluoroacetic acid/30 min. Protein concentration in the eluent was monitored by absorbance at 280 nm and each protein peak was collected. A portion of each fraction was checked for its trypsin-inhibiting activity in accordance with the procedure described in Example 17 (1) and active fractions were pooled. The pooled sample was dried under reduced pressure using a centrifugation vacuum concentrator (Tomy Seiko Co., Ltd.) to obtain a purified polypeptide sample. The purified polypeptide was used for the SDS-polyacrylamide gel electrophoresis in the following step (5), the amino acid sequence analysis in the step (6) and the activity measurement in Example 12.

(5) SDS-polyacrylamide gel electrophoresis

The purified polypeptide sample obtained in the above procedure (4) was subjected to SDS-polyacrylamide gel electrophoresis (to be referred to as "SDS-PAGE" hereinafter) in accordance with Laemmli's method (Laemmli, U. K., Nature, vol. 227, pp. 680–685, 1970). That is, the purified polypeptide was dissolved in 100 μl of distilled water, and a portion of the solution was mixed with the same volume of Seprasol II (Daiichi Pure Chemicals Co., Ltd.). The mixture was treated at 100° C. for 5 minutes and then electrophoresed with 15% gel (8 cm×9 cm, 1 mm in thickness) at 15 mA for 50 minutes and then at 30 mA for 35 minutes. In this instance, a commercial molecular weight marker kit was used (Electrophoresis Calibration Kit, Pharmacia). After the electrophoresis, staining was carried out with a commercial silver staining kit (2D-Silver Staining Reagent II, Daiichi Pure Chemicals Co., Ltd.). The purified sample showed a single band by SDS-PAGE.

(6) Determination of amino acid sequence

The purified polypeptide sample obtained in the above procedure (4) was dissolved in 50% acetic acid solution and its amino acid sequence was determined using Model 477A Protein Sequencing System 120A PTH Analyzer (Applied Biosystems Inc.). Identification of the amino acid sequence was determined by detecting PTH-amino acid at an absorbance of 270 nm, based on the retention time of standard PTH-amino acids (Applied Biosystems Inc.) which have been isolated in the same procedure.

As a results, it was confirmed that the purified polypeptide sample obtained in the above procedure (4) was the polypeptide of interest, Y46E (cf. amino acids 1–70 of SEQ. I.D. No.:2 in SEQUENCE LISTING).

Example 3

Production of polypeptide O19K

A polypeptide, Q19K, having an amino acid sequence derived from the aforementioned formula 1 amino acid sequence by substituting Lys for the 15 position Gln of the formula 1 sequence counting from its N-terminus was prepared in the following manner.

(1) Cloning of DNA fragment

Plasmid pM558 was derived from the aforementioned plasmid pM552 in the following manner. First, an oligomer TV12DD (FIG. 10, SEQ. I.D. NO.:53 ) for mutation introduction use was synthesized chemically. Next, ssDNA was prepared using M13 phage obtained in Example 2 (1) from E. coli JM109, in the same manner as in Example 2 (1) making use of the aforementioned Mutan™-K kit, and the desired mutation was introduced into the ssDNA using the TV12DD. Thereafter, PCR was carried out in accordance with the procedure described in Example 2 (1) using the thus mutation-introduced ssDNA as a template. In this instance, ScaI sense primer prepared in Example 2 (1) was used as the sense primer and an M13 primer RV (Takara Shuzo Co., Ltd. ) was used as the antisense primer. The thus obtained PCR product was digested with BamHI and inserted into plasmid pM469 in the same manner as in Example 2 (2) to obtain plasmid pM558.

Site-directed mutagenesis was carried out by PCR, using the method of Landt et al. (Landt, O. et al., Gene, vol. 96, pp. 125–128, 1990), using the thus obtained plasmid pM558 as a template for PCR use. First, a HindIII primer (FIG. 11, SEQ. I.D. NO.:54) and a Q19K primer (FIG. 12, SEQ. I.D. NO.:55) to be used respectively as a sense primer and an antisense primer in the first PCR were synthesized chemically. First PCR was carried out making use of the aforementioned Gene Amp® PCR Reagent Kit, using the thus synthesized sense and antisense primers and plasmid pM558 as a template and repeating 30 cycles of the reaction. In this instance, each reaction cycle was effected by a series of incubations at 94° C. for 1 minute, 55° C. for 2 minutes and 72° C. for 3 minutes in that order. A portion of the amplified product, of the first PCR was applied to 1.5% agarose gel electrophoresis to confirm formation of a DNA fragment of interest having a size of about 160 bp. The DNA fragment of interest was then extracted and purified from the gel by means of phenol treatment and ethanol precipitation, and the thus purified DNA fragment was dissolved in TE buffer. Thereafter, a second PCR was carried out in the same manner as the above first PCR using the thus dissolved DNA fragment as a sense primer and the plasmid DM558 as a template. In this instance, a pBR BamHI primer (FIG. 13, SEQ. I.D. NO.:56) prepared as in Example 2-(2), obtained by chemical synthesis was used as an antisense primer.

A portion of the amplified product of the second PCR was applied to 1.5% agarose gel electrophoresis to confirm formation of a DNA fragment of interest having a size of about 350 bp. The DNA fragment was then extracted and purified from the gel by means of phenol treatment and ethanol precipitation to obtain the DNA fragment of the present invention.

(2) Construction of expression vector

Figure 14:
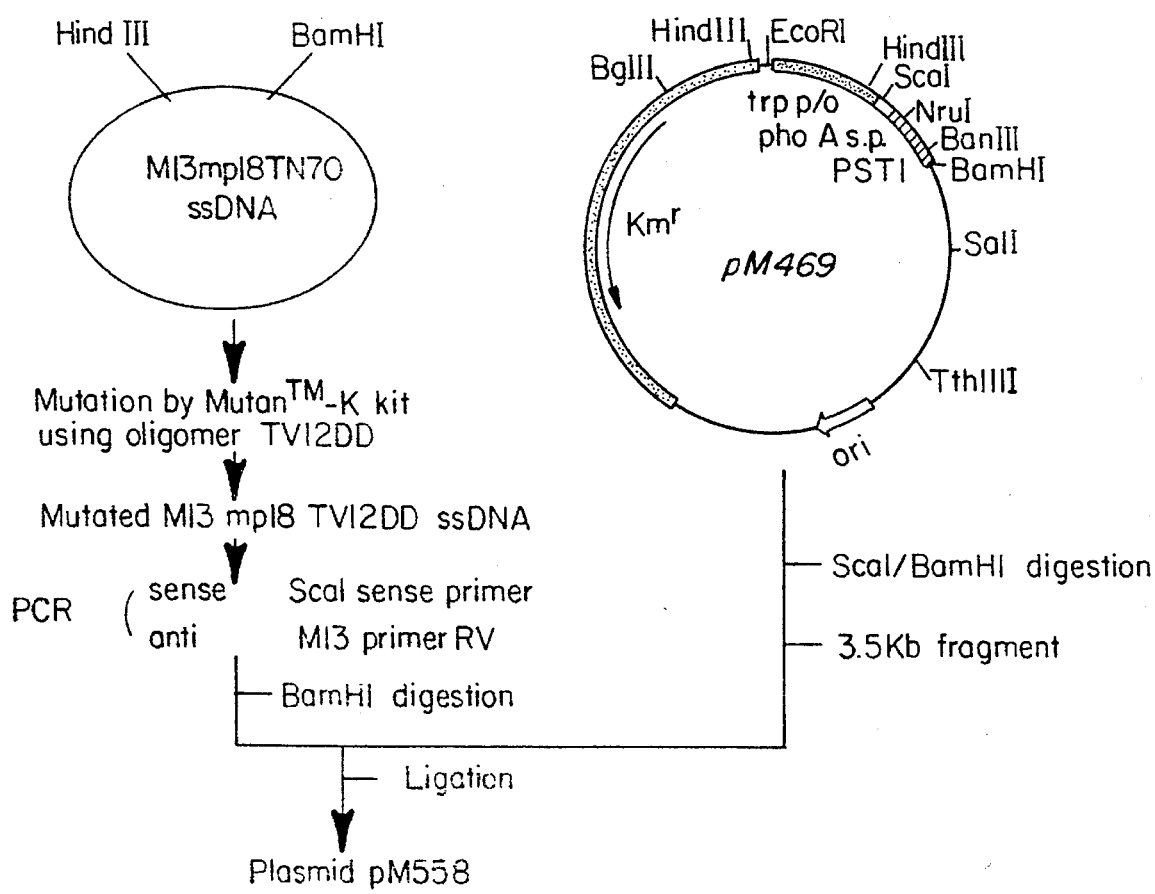
FIG. 14 is a schematic for a process for the construction of plasmid pM576.
Figure 15:
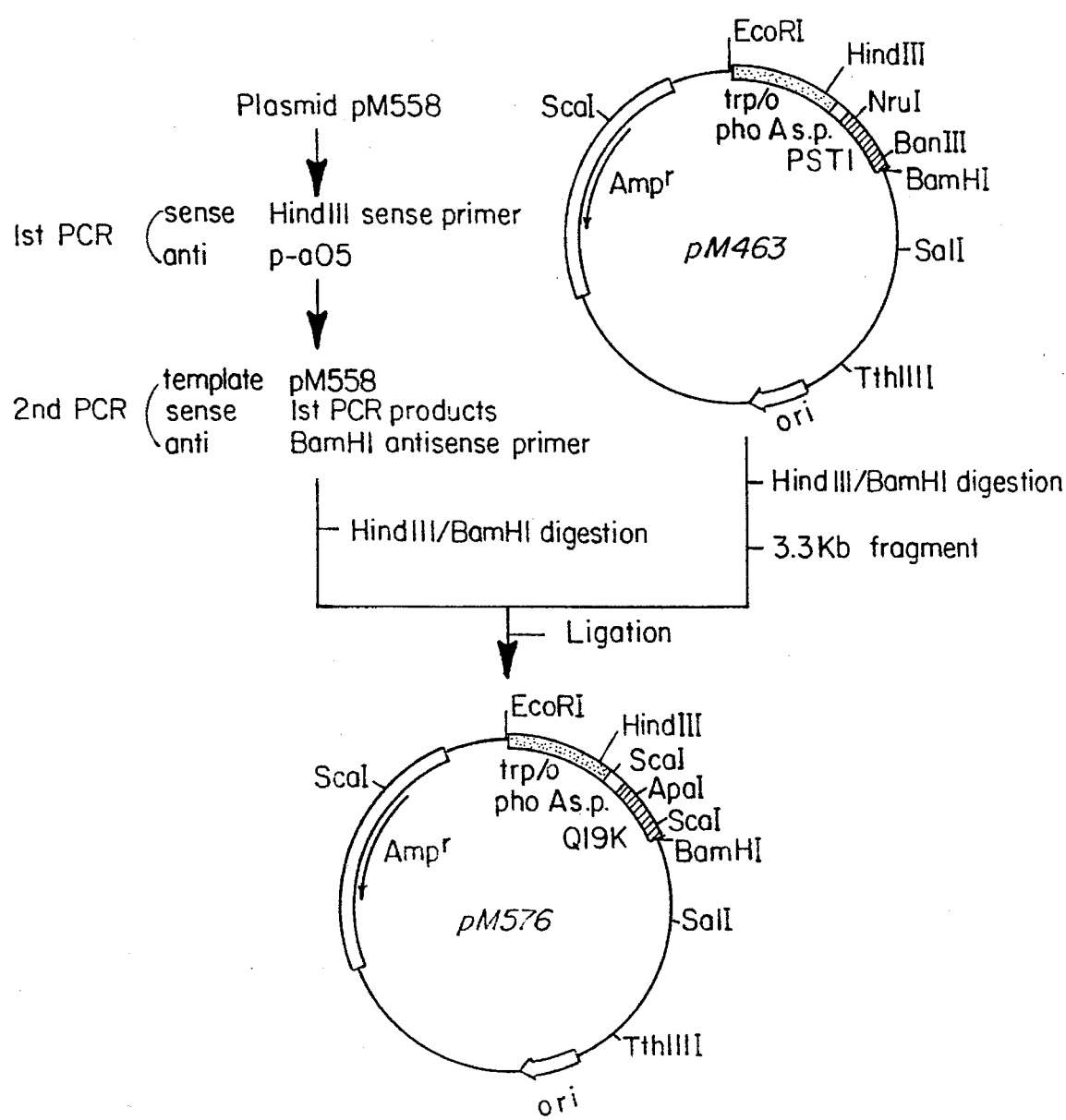
FIG. 15 is a schematic for a process for the construction of plasmid pM576.

The plasmid pM463 (Kanamori T. et al. ) described in the foregoing was double-digested with HindIII and BamHI, and the thus digested mixture was subjected to 0.7% low melting point agarose gel electrophoresis no obtain a DNA fragment of about 3.3 kb. Next, the DNA fragment of the present invention having a size of about 350 bp obtained in the above step (1) was double-digested with HindIII and BamHI, and the thus digested fragment was ligated with the just described DNA fragment of about 3.3 kb using the aforementioned T4 DNA ligase, thereby obtaining an expression plasmid pM576 (cf. FIGS. 14 and 15).

The thus obtained expression plasmid pM576 was double-digested with HindIII and BamHI, and a DNA fragment of interest having a size of about 310 bp was extracted and purified. The thus purified DNA fragment of interest was ligated with each of the aforementioned phage vectors M13mp18 and M13mp19 which have been double-digested with HindIII and BamHI in advance, and the thus ligated product was transfected into E. coli JM109. Thereafter, ssDNA was prepared from each of the resulting plaques and subjected to sequencing using the aforementioned DNA sequencer. The thus confirmed nucleotide sequence of a region of plasmid pM576 from its HindIII site to its BamHI site containing the novel DNA fragment of the present invention and its corresponding amino acid sequence are shown in FIG. 16 (cf. SEQ. I.D. NO.:3 in the SEQUENCE LISTING).

(3) Preparation and culturing of transformant

A transformant, E. coli JE5505 (pM576), was isolated by transforming E. coli JE5505 with the plasmid pM576 obtained in the above procedure (2), in accordance with Hanahan's method. The thus isolated transformant was subsequently cultured in the same manner as in Example 2 (3) to recover culture supernatant, except that ampicillin was added to the culture medium to a final concentration of 50 μg/ml in stead of kanamycin.

The culture supernatant was diluted with 0.1% BSA/0.2M triethanolamine-HCl buffer (pH 7.8), and the diluted samples were used for the measurement of trypsin-inhibiting activity in accordance with the procedure described in Example 17 (1). In this instance, culture supernatant of a transformant, E. coli JE5505 (pM463C), was used as a control in the activity measurement, which has been obtained by deleting the polypeptide Q19K-encoding nucleotide sequence from plasmid pM576 .

Markedly high trypsin-inhibiting activity was found in the culture supernatant of E. coli JE5505 (pM576) in comparison with the control. The transformant E. coli JE5505 (pM576) has been deposited by the present inventors on Jul. 16, 1991, in the Fermentation Research Institute, Agency of Industrial Science and Technology, and has been assigned the designation FERM P-12358 which was subsequently transferred to the International Depository Authority on Oct. 17, 1991, as FERM BP-3614.

(4) Purification of the novel polypeptide of the present invention from culture supernatant of E. coli JE5505 (pM576)

The polypeptide of the present invention was purified from the culture supernatant obtained in the above procedure (3) by means of ammonium sulfate precipitation, gel filtration, anion exchange chromatography and reverse phase chromatography in accordance with the procedure described in Example 2 (4). The obtained purified sample was used for the following SDS-PAGE (5), amino acid analysis (6) and activity measurement in Example 12.

(5) SDS-PAGE

The purified polypeptide sample obtained in the above procedure (4) was subjected to SDS-PAGE in accordance with the procedure described in Example 2 (5). After the electrophoresis, staining was carried out with the aforementioned commercial silver staining kit. The purified sample showed a single band by SDS-PAGE.

(6) Determination of amino acid sequence

The purified polypeptide sample obtained in the above procedure (4) was dissolved in 50% acetic acid solution and its amino acid sequence was determined in accordance with the procedure described in Example 2 (6).

As a result, it was confirmed that the purified polypeptide sample obtained in the above procedure (4) was the polypeptide Q19K of the present invention (cf. amino acids 1–70 of SEQ. I.D. NO.:4 of the SEQUENCE LISTING).

Example 4

Production of polypeptide Q19R

A polypeptide, Q19R, having an amino acid sequence derived from the aforementioned formula 1 amino acid sequence by substituting Arg for the 15 position Gln of the formula 1 sequence counting from its N-terminus was prepared in the following method.

(1) Cloning of DNA fragment

Plasmid pM594 was derived from the aforementioned plasmid pM552 in the following procedure. First, an ANa68 primer (FIG. 17, SEQ. I.D. NO.:57) was synthesized chemically. Using the aforementioned pM552 as a template, the thus synthesized AN68 primer as an antisense primer and the HindIII primer prepared in Example 3 (1) as a sense primer, a first PCR was carried out in accordance with the procedure described in Example 3 (1) making use of the aforementioned Gene Amp® PCR Reagent Kit. A portion of the amplified product of the first PCR was applied to 1.5% agarose gel electrophoresis to confirm formation of a DNA fragment of interest having a size of about 130 bp. The DNA fragment of interest was then extracted and purified from the gel by means of phenol treatment and ethanol precipitation, and the thus purified DNA fragment was dissolved in TE buffer. Thereafter, a second PCR was carried out in the same manner as the above first PCR using the thus dissolved DNA fragment as a sense primer and the plasmid pM552 as a template. In this instance, the pBR BamHI primer prepared in Example 3 (1) was used as an antisense primer. A portion of the amplified product of the second PCR was applied to 1.5% agarose gel electrophoresis to confirm formation of a DNA fragment of interest having a size of about 350 bp. The DNA fragment was extracted and purified from the gel by means of phenol treatment and ethanol precipitation, and the thus purified fragment was digested with HindIII and BamHI to obtain a DNA fragment of about 300 bp. Thereafter, the thus obtained DNA fragment was inserted into plasmid pM463 in the same manner as in Example 3 (2) to obtain plasmid pM594.

Next, sine-directed mutagenesis was carried out by the method of Landt et al. in the following manner. Firstly, a SacII primer (FIG. 18, SEQ. I.D. NO.:58) and a Q19R primer (FIG. 19, SEQ. I.D. NO.:59) were obtained by chemical synthesis to be used respectively as a sense primer and an antisense primer. A first PCR was carried out in the same manner as described above, using the thus synthesized sense and antisense primers and the aforementioned plasmid pM594 as a template. A portion of the amplified product of the first PCR was applied to 4% agarose gel electrophoresis to confirm formation of a DNA fragment of interest having a size of about 70 bp. The DNA fragment of interest was then extracted and purified from the gel by means of phenol treatment and ethanol precipitation, and the thus purified DNA fragment was dissolved in TE buffer. Thereafter, a second PCR was carried out in the same manner as the above first PCR using the thus dissolved DNA fragment as a sense primer and the plasmid pM594 as a template. In this instance, the pBR BamHI primer prepared in Example 3 (1) was used as an antisense primer. A portion of the amplified product of the second PCR was applied to 1.5% agarose gel electrophoresis to confirm formation of a DNA fragment of interest having a size of about 260 bp. The DNA fragment was then extracted and purified from the gel by means of phenol treatment and ethanol precipitation to obtain the DNA fragment of the present invention.

(2) Construction of expression vector

Figure 20:
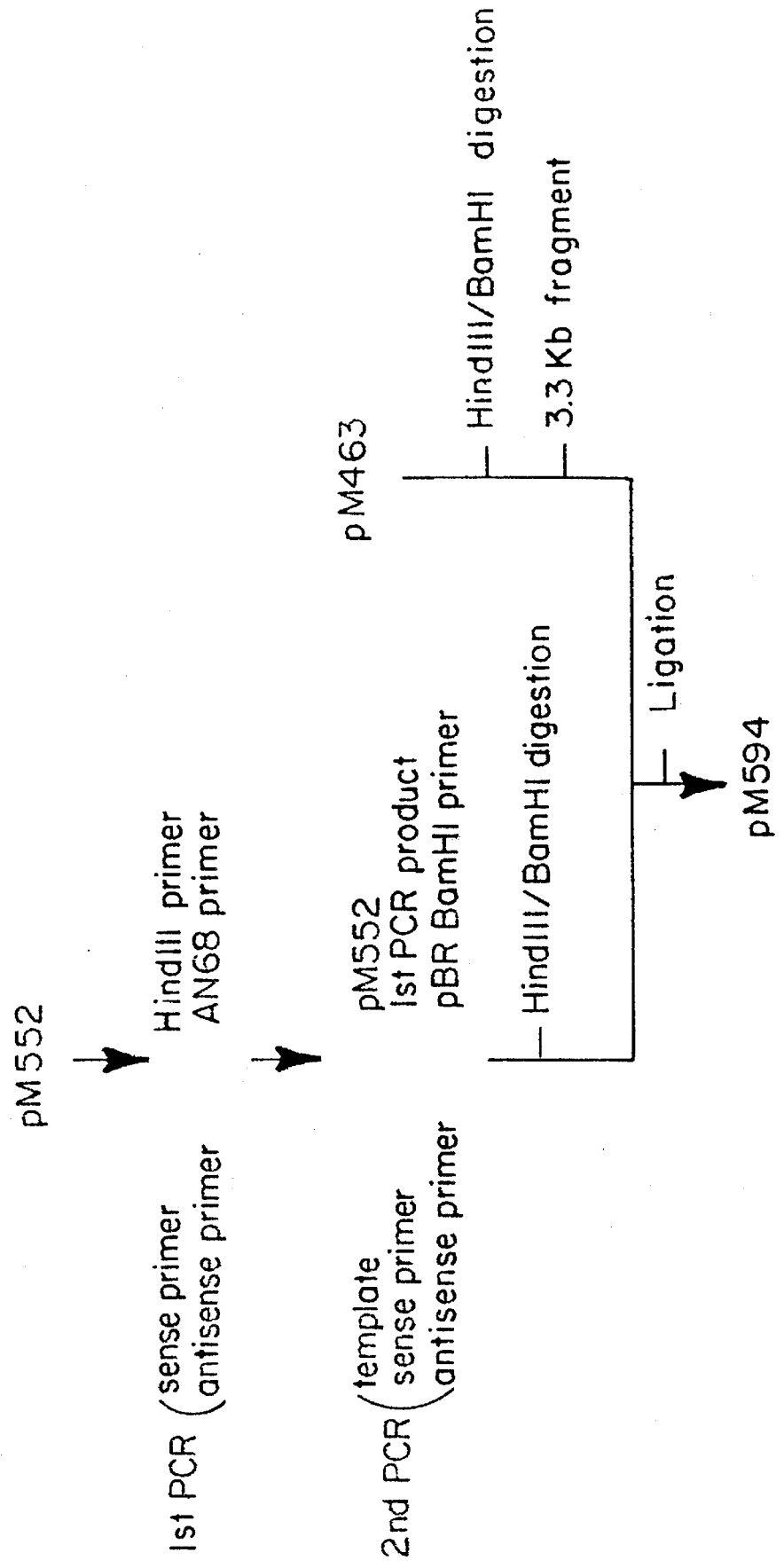
FIG. 20 is a schematic of a process for the construction of plasmid pM735.

The plasmid pM594 was double-digested with SacII and BamHI, and a DNA fragment of interest having a size of about 3.4 kb was extracted and purified from the digested sample. The thus purified DNA fragment was ligated with the DNA fragment of about 260 bp obtained in the above step (1) using the aforementioned T4 DNA ligase, thereby obtaining an E. coli expression plasmid pM735 (cf. FIGS. 20 and 21). The thus obtained plasmid pM735 was double-digested with HindIII and BamHI, and a DNA fragment of interest having a size of about 300 bp was extracted and purified. Thereafter, sequencing was carried out in the same manner as described in Example 2 (2) using the aforementioned DNA sequencer.

The thus confirmed nucleotide sequence of a region of plasmid pM735 from its HindIII site to its BamHI site containing the novel DNA fragment of the present invention and its corresponding amino acid sequence are shown in FIG. 22 (cf. SEQ. I.D. NO.:5 in the SEQUENCE LISTING).

(3) Preparation and culturing of transformant

A transformant, E. coli JE5505 (pM735), was isolated by transforming E. coli JE5505 with the plasmid pM735 obtained in the above procedure (2), in accordance with the Hanahan's method. The thus isolated transformant was subsequently cultured in the same manner as in Example 3 (3) to recover culture supernatant.

The culture supernatant thus prepared was diluted with 0.1% BSA/0.2M triethanolamine-HCl buffer (pH 7.8), and the diluted samples were used for the measurement of trypsin-inhibiting activity in accordance with the procedure described in Example 17 (1). In this instance, culture supernatant of the transformant, E. coil JE5505 (pM463 C), prepared in Example 3 (3) was used as a control in the activity measurement. As the results, markedly high trypsin-inhibiting activity was found in the culture filtrate of E. coli JE5505 (pM735) in comparison with the control.

The transformant E. coil JE5505 (pM735) has been deposited by the present inventors on May 1, 1992, in the Fermentation Research Institute, Agency of Industrial Science and Technology, and has been assigned the designation FERM P-12945.

(4) Purification of the novel polypeptide of the present invention from culture supernatant of E. coil JE5505 (pM735)

The polypeptide of the present invention was purified from the culture supernatant obtained in the above procedure (3) by means of ammonium sulfate precipitation, gel filtration, anion exchange chromatography and reverse phase chromatography in accordance with the procedure described in Example 2 (4). The thus obtained purified sample was used for the following SDS-PAGE (5), amino acid analysis (6) and activity measurement in Example 17.

(5) SDS-PAGE

The purified polypeptide sample obtained in the above procedure (4) was subjected to SDS-PAGE in accordance with the procedure described in Example 2 (5). After the electrophoresis, staining was carried out with the aforementioned commercial silver staining kit. The purified sample showed a single band by SDS-PAGE.

(6) Determination of amino acid sequence

The purified polypeptide sample obtained in the above procedure (4) was dissolved in 50% acetic acid solution and its amino acid sequence was determined in accordance with the procedure described in Example 2 (6).

As the results, it was confirmed that the purified polypeptide sample obtained in the above procedure (4) is the polypeptide Q19R of the present invention (cf. amino acids 1–68 of SEQ. I.D. NO.:6 of the SEQUENCE LISTING).

Example 5

Production of polypeptide Q19K/Y46E

A polypeptide, Q19K/Y46E, having an amino acid sequence derived from the aforementioned formula 1 amino acid sequence by substituting Lys for the 15 position Gln, as well as Glu for the 42 position Tyr, of the formula 1 sequence counting from its N-terminus was prepared in the following manner.

(1) Cloning of DNA fragment

A first PCR was carried out in the same manner as in Example 3 (1), making use of the aforementioned Gene Amp® PCR Reagent Kit and using the HindIII primer and the Q19K primer prepared in Example 3 (1) as sense and antisense primers and the plasmid pM594 prepared in Example 4 (1) as a template. A portion of the amplified product of the first PCR was applied to 1.5% agarose gel electrophoresis to confirm formation of a DNA fragment of interest having a size of about 170 bp. The DNA fragment of interest was then extracted and purified from the gel by means of phenol treatment and ethanol precipitation, and the thus purified DNA fragment was dissolved in TE buffer. Thereafter, a second PCR was carried out in the same manner as the above first PCR using the thus dissolved DNA fragment as a sense primer and plasmid pM575B as a template. In this instance, the pBR BamHI primer prepared in Example 3 (1) was used as an antisense primer. A portion of the amplified product by the second PCR was applied to 1.5% agarose gel electrophoresis to confirm formation of a DNA fragment of interest having a size of about 350 bp. The DNA fragment was then extracted and purified by means of phenol treatment and ethanol precipitation to obtain the DNA fragment of the present invention.

(2) Construction of expression vector

Figure 23:
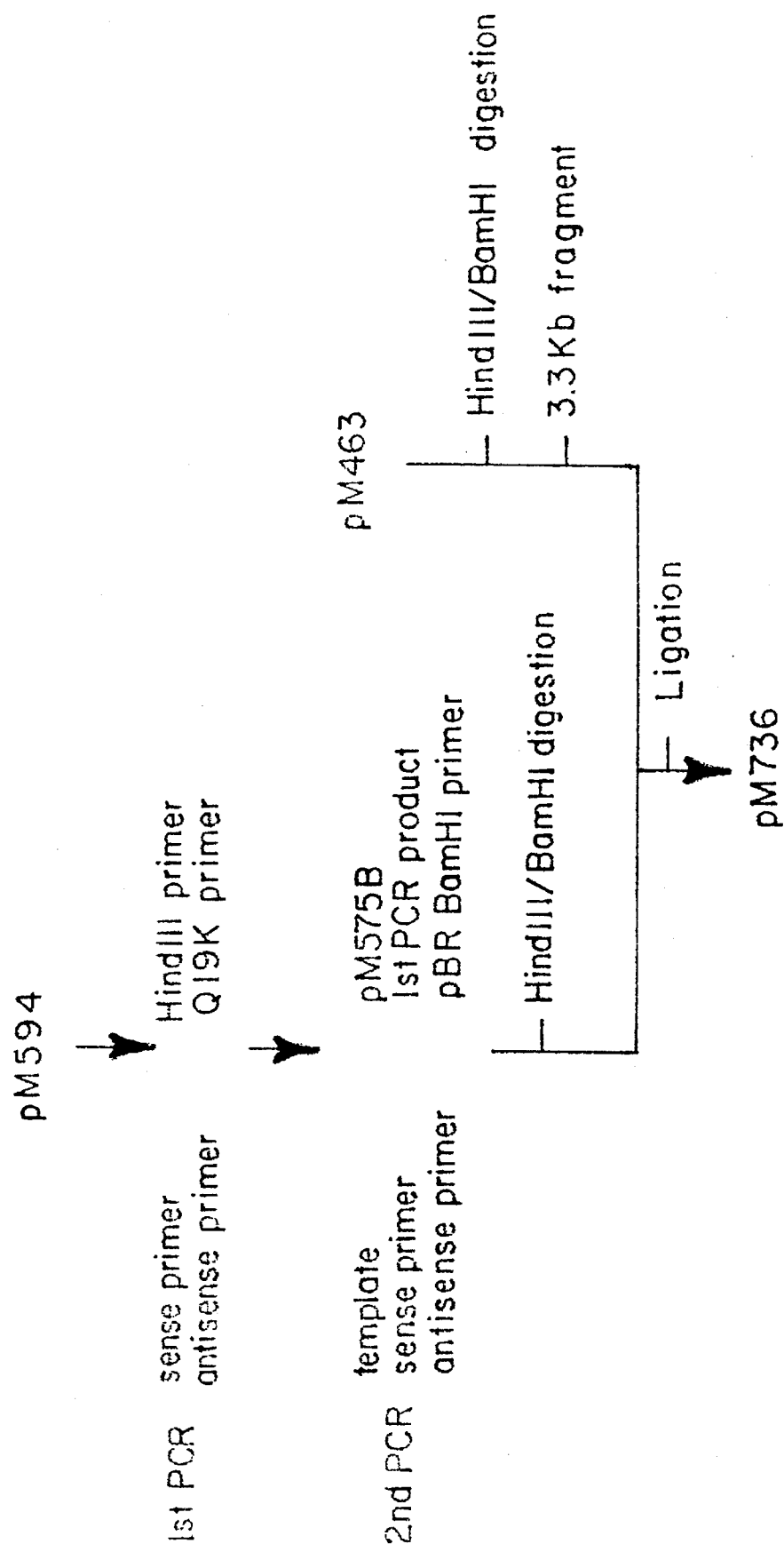
FIG. 23 is a schematic of a process for the construction of plasmid DM736.

The DNA fragment of the present invention obtained in the above step (1) was inserted into plasmid pM463 in accordance with the procedure of Example 3 (2) to prepare an expression plasmid pM736 (cf. FIG. 23). The thus prepared plasmid pM736 was double-digested with HindIII and BamHI, and a DNA fragment of interest having a size of about 300 bp was extracted and purified. The thus purified DNA fragment of interest was subjected to sequencing using the aforementioned DNA sequencer in the same manner as described in Example 2 (2). The thus confirmed nucleotide sequence of a region of plasmid pM736 from its HindIII site to its BamHI site containing the novel DNA fragment of the present invention and its corresponding amino acid sequence are shown in FIG. 24 (cf. SEQ. I.D. NO.:7 in the SEQUENCE LISTING).

(3) Preparation and culturing of transformant

A transformant, E. coli JE5505 (pM736), was isolated by transforming E. coli JE5505 with the plasmid pM736 obtained in the above procedure (2). The thus isolated transformant was subsequently cultured in the same manner as in Example 3 (3) to recover culture supernatant.

The culture supernatant thus prepared was diluted with 0.1% BSA/0.2M triethanolamine-HCl buffer (pH 7.8), and the diluted samples were used for the measurement of trypsin-inhibiting activity in accordance with the procedure described in Example 17 (1). In this instance, culture supernatant of the transformant, E. coli JE5505 (pM463 C), prepared in Example 3 (3) was used as a control in the activity measurement. As the results, markedly high trypsin-inhibiting activity was found in the culture supernatant of E. coli JE5505 (pM736) in comparison with the control.

The transformant E. coli JE5505 (pM736) has been deposited by the present inventors on May 1, 1992, in the Fermentation Research Institute, Agency of Industrial Science and Technology, and has been assigned the designation FERM P-12946.

(4) Purification of the novel polypeptide of the present invention from culture supernatant of E. coli JE5505 (pM736)

The polypeptide of the present invention was purified from the culture supernatant obtained in the above procedure (3) by means of ammonium sulfate precipitation, gel filtration, anion exchange chromatography and reverse phase chromatography in accordance with the procedure described in Example 2 (4). The thus purified polypeptide sample was used for the following SDS-PAGE (5), amino acid analysis (6) and activity measurement in Example 17.

(5) SDS-PAGE

The purified polypeptide sample obtained in the above procedure (4) was subjected to SDS-PAGE in accordance with the procedure described in Example 2 (5). After the electrophoresis, staining was carried out with the aforementioned commercial silver staining kit. The purified sample showed a single band by SDS-PAGE.

(6) Determination of amino acid sequence

The purified polypeptide sample obtained in the above procedure (4) was dissolved in 50% acetic acid solution and its amino acid sequence was determined in accordance with the procedure described in Example 2 (6).

As the results, it was confirmed that the purified polypeptide sample obtained in the above procedure (4) is the polypeptide Q19K/Y46E of the present invention (cf. amino acids 1–68 of SEQ. I.D. NO.:8 of the SEQUENCE LISTING).

Example 6

Production of polypeptide R11E/Y46E

A polypeptide, R11E/Y46E, having an amino acid sequence derived from the aforementioned formula 1 amino acid sequence by substituting Glu for the 7 position Arg, as well as Glu for the 42 position Tyr, of the formula 1 sequence counting from its N-terminus was prepared in the following method.

(1) Cloning of DNA fragment

An R11E primer (FIG. 25, SEQ. I.D. NO.:60) was synthesized chemically to be used as an antisense primer. Using the antisense primer thus synthesized and the HindIII sense primer prepared in Example 3 (1), a first PCR was carried out in accordance with the procedure described in Example 3 (1), making use of the aforementioned Gene Amp® PCR Reagent Kit. In this instance, plasmid pM594, prepared in Example 4 (1) was used as a template. A portion of the amplified product of the first PCR was applied to 1.5% agarose gel electrophoresis to confirm presence of a band of interest having a size of about 150 bp. The thus amplified product was extracted and purified by means of phenol treatment and ethanol precipitation, and the purified product was dissolved in TE buffer. Thereafter, a second PCR was carried out in the same manner as the above first PCR using the thus dissolved product as a sense primer and the aforementioned plasmid pM575B as a template. In this instance, the pBR BamHI primer prepared in Example 3 (1) was used as an antisense primer. A portion of the amplified product of the second PCR was applied to 1.5% agarose gel electrophoresis to confirm formation of a DNA fragment of interest having a size of about 350 bp. The DNA fragment was then extracted and purified by means of phenol treatment and ethanol precipitation to obtain the DNA fragment of the present invention.

(2) Construction of expression vector

Figure 26:
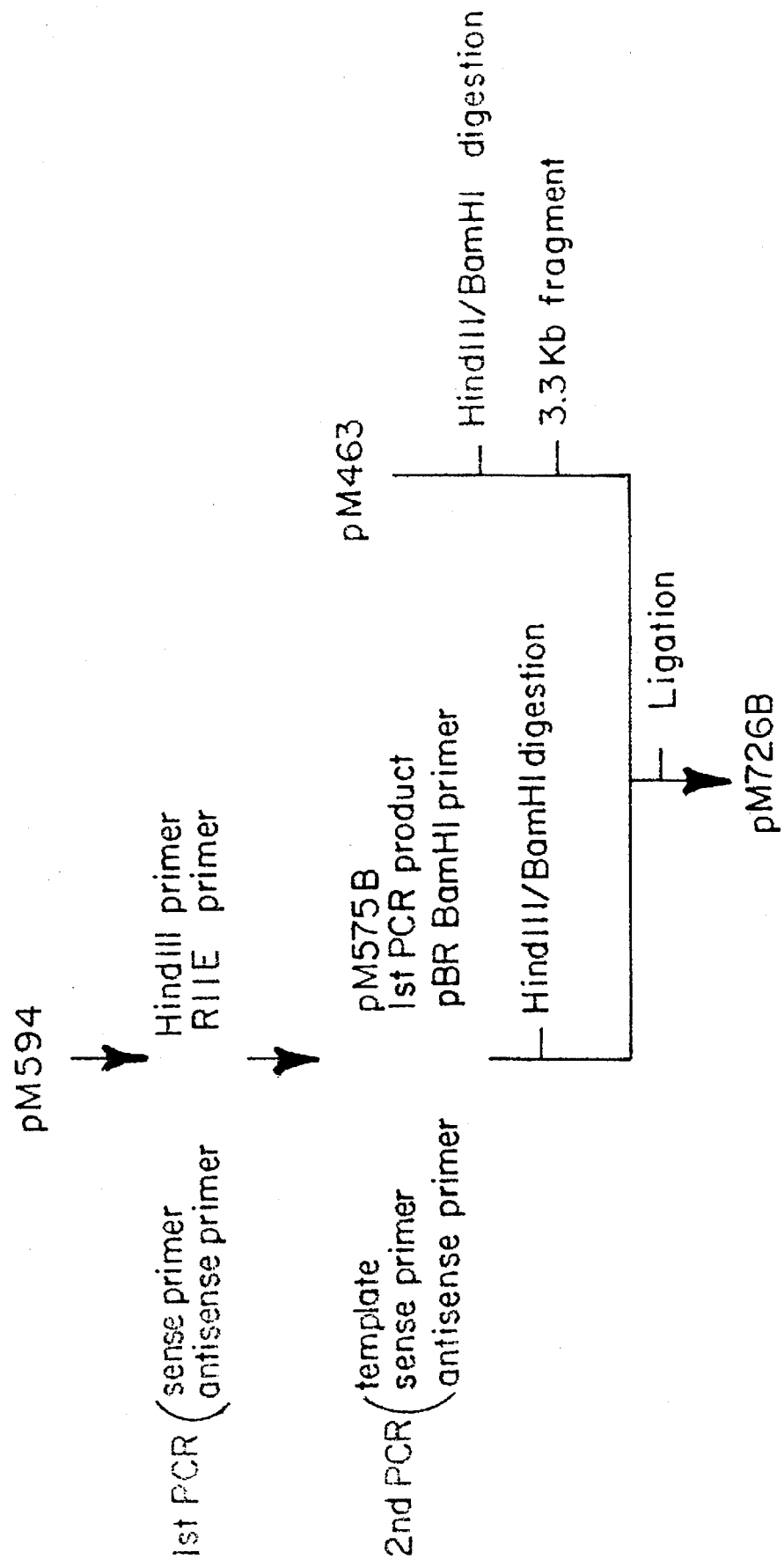
FIG. 26 is a schematic of a process for the construction of plasmid pM726B.

The DNA fragment of the present invention having a size of about 350 bp prepared in the above step (1) was inserted into plasmid pM463 in the same manner as in Example 3 (2) to obtain an expression plasmid pM726B (cf. FIG. 26). The thus obtained expression plasmid pM726B was double-digested with HindIII and BamHI, and a DNA fragment of interest having a size of about 300 bp was extracted and purified. The thus purified DNA fragment of interest was subjected to sequencing using the aforementioned DNA sequencer in the same manner as in Example 2 (2).

The thus confirmed nucleotide sequence of a region of plasmid pM726B from its HindIII site to its BamHI site containing the novel DNA fragment of the present invention and its corresponding amino acid sequence are shown in FIG. 27 (cf. SEQ. I.D. NO.:9 in the SEQUENCE LISTING).

(3) Preparation and culturing of transformant

A transformant, *E. coli* JE5505 (pM726B), was isolated by transforming *E. coli* JE5505 with the plasmid pM726B obtained in the above procedure (2), in accordance with Hanahan's method. The thus isolated transformant was subsequently cultured in the same manner as in Example 3 (3) to recover culture supernatant.

The culture supernatant thus prepared was diluted with 0.1% BSA/0.2M triethanolamine-HCl buffer (pH 7.8), and the diluted samples were used for the measurement of trypsin-inhibiting activity in accordance with the procedure described in Example 17 (1). In this instance, culture supernatant of the transformant, *E. coli* JE5505 (pM463 C), obtained in Example 3 (3) was used as a control in the activity measurement. As a result, markedly high trypsin-inhibiting activity was found in the culture supernatant of *E. coli* JE5505 (pM726B) in comparison with the control.

(4) Purification of the novel polypeptide of the present invention from culture supernatant of *E. coli* JE5505 (pM726B)

The polypeptide of the present invention was purified from the culture supernatant obtained in the above procedure (3) by means of ammonium sulfate precipitation, gel filtration, anion exchange chromatography and reverse phase chromatography in accordance with the procedure described in Example 2 (4). The purified polypeptide sample was used for the following SDS-PAGE (5), amino acid analysis (6) and activity measurement in Example 17.

(5) SDS-PAGE

The purified polypeptide sample obtained in the above procedure (4) was subjected to SDS-PAGE in accordance with the procedure described in Example 2 (5). After the electrophoresis, staining was carried out with the aforementioned commercial silver staining kit. The purified sample showed a single band by SDS-PAGE.

(6) Determination of amino acid sequence

The purified polypeptide sample obtained in the above procedure (4) was dissolved in 50% acetic acid solution and its amino acid sequence was determined in accordance with the procedure described in Example 2 (6).

As a result, it was confirmed that the purified polypeptide sample obtained in the above procedure (4) is the aimed polypeptide R11E/Y46E of the present invention (cf. amino acids 1–68 of SEQ. I.D. NO.:10 of the SEQUENCE LISTING).

Example 7

Production of polypeptide Y46E-AN

A polypeptide, Y46E-AN, having an amino acid sequence derived from the aforementioned formula 1 amino acid sequence by substituting Glu for the 42 position Tyr of the formula 1 sequence counting from its N-terminus was prepared in the following manner.

(1) Cloning of DNA fragment and construction of expression vector

Figure 28:
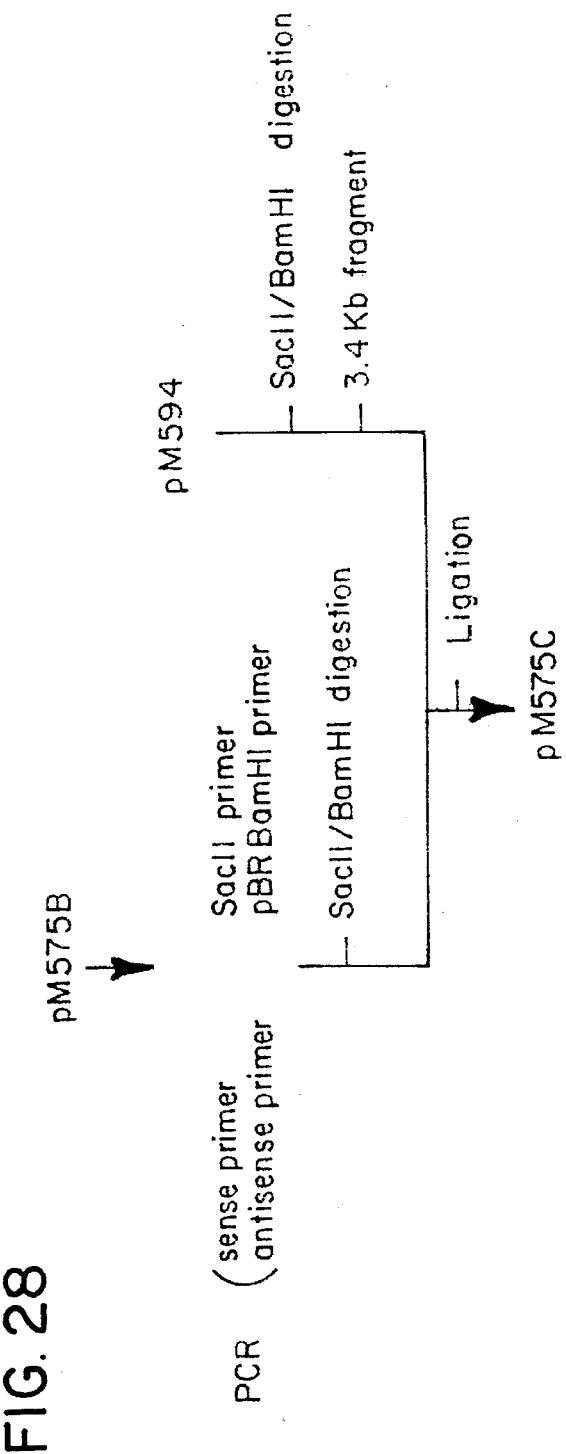
FIG. 28 is a schematic of a process for the construction of plasmid pM575C.

PCR was carried out in the same manner as in Example 3 (1), making use of the aforementioned Gene Amp® PCR Reagent Kit and using the SacII primer prepared in Example 4 (1) and the pBR BamHI primer prepared in Example 3 (1) as sense and antisense primers and the aforementioned plasmid pM575B as a template. A portion of the amplified product of the PCR was applied to 1.5% agarose gel electrophoresis to confirm presence of a single band of interest having a size of about 250 bp. The thus amplified product was extracted and purified by means of phenol treatment and ethanol precipitation, and the thus purified product was digested with SacII and BamHI to obtain a DNA fragment of about 220 bp. The thus obtained DNA fragment of about 220 bp was ligated with a DNA fragment having a size of about 3.4 kb which have been prepared from plasmid pM594 by double-digesting it with SacII and BamHI, thereby obtaining an expression plasmid pM575C (cf. FIG. 28). The thus prepared plasmid pM575C was double-digested with HindIII and BamHI, and a DNA fragment of interest having a size of about 300 bp was extracted and purified Thereafter, the thus purified DNA fragment was subjected to sequencing using the aforementioned DNA sequencer in the same manner as described in Example 2 (2).

The thus confirmed nucleotide sequence of a region of plasmid pM575C from its HindIII site to its BamHI site containing the novel DNA fragment of the present invention and its corresponding amino acid sequence are shown in FIG. 29 (cf. SEQ. I.D. NO.:11 in the SEQUENCE LISTING).

(2) Preparation and culturing of transformant

A transformant, *E. coli* JE5505 (pM575C), was isolated by transforming *E. coli* JE5505 with the plasmid pM575C obtained in the above procedure (1), in accordance with Hanahan's method. The thus isolated transformant was subsequently cultured in the same manner as in Example 3 (3) to recover culture supernatant.

The culture supernatant thus prepared was diluted with 0.1% BSA/0.2M triethanolamine-HCl buffer (pH 7.8), and the diluted samples were used for the measurement of trypsin-inhibiting activity in accordance with the procedure described in Example 17 (1). In this instance, culture supernatant of the transformant, *E. coli* JE5505 (pM463C), obtained in Example 3 (3) was used as a control in the activity measurement. Markedly high trypsin-inhibiting activity was found in the culture supernatant of *E. coli* JE5505 (pM575C) in comparison with the control.

(3) Purification of the novel polypeptide of the present invention from culture supernatant of *E. coli* JE5505 (pM575C)

The polypeptide of the present invention was purified from the culture supernatant obtained in the above procedure (2) by means of ammonium sulfate precipitation, gel filtration, anion exchange chromatography and reverse phase chromatography in accordance with the procedure described in Example 2 (4). The thus obtained purified sample was used for the following SDS-PAGE (4), amino acid analysis (5) and activity measurement in Example 17.

(4) SDS-PAGE

The purified polypeptide sample obtained in the above procedure (3) was subjected to SDS-PAGE in accordance with the procedure described in Example 2 (5). After completion of the electrophoresis, staining was carried out with the aforementioned commercial silver staining kit. The purified sample showed a single band by SDS-PAGE.

(5) Determination of amino acid sequence

The purified polypeptide sample obtained in the above procedure (3) was dissolved in 50% acetic acid solution and its amino acid sequence was determined in accordance with the procedure described in Example 2 (6).

As a result, it was confirmed that the purified polypeptide sample obtained in the above procedure (3) is the aimed polypeptide Y46E-AN of the present invention (cf. amino acids 1–68 of SEQ. I.D. NO.:12 of the SEQUENCE LISTING).

Example 8

Production of polypeptide O19K-AN

A polypeptide, Q19K-AN, having an amino acid sequence derived from the aforementioned formula 1 amino acid sequence by substituting Lys for the 15 position Gln of the formula 1 sequence counting from its N-terminus was prepared in the following method.

(1) Cloning of DNA fragment and construction of expression vector

Figure 30:
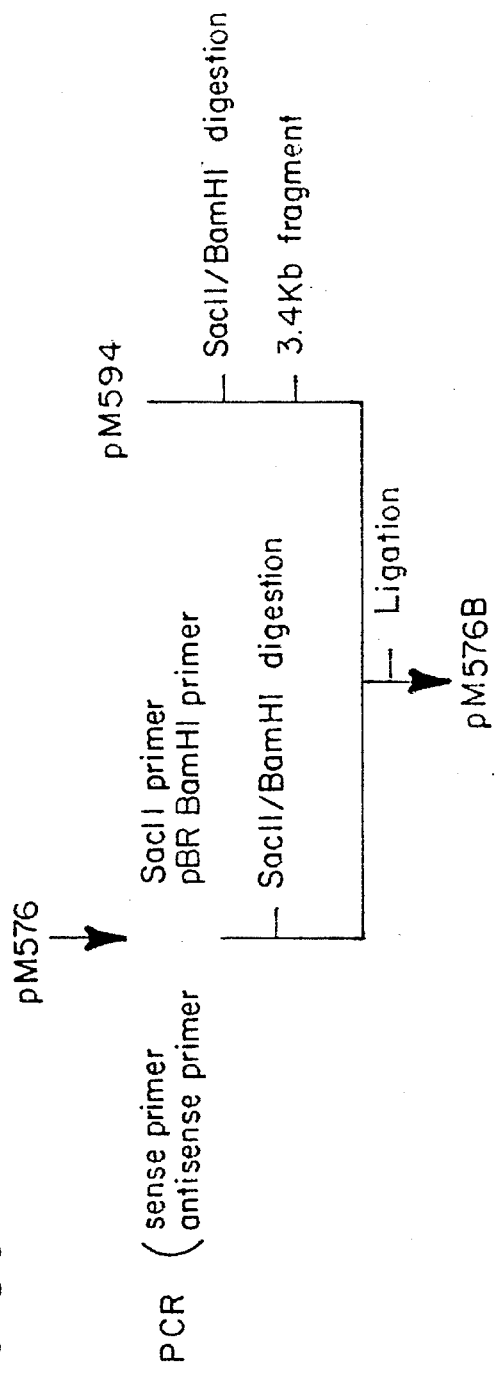
FIG. 30 is a schematic of a process for the construction of plasmid pM576B.

PCR was carried out in the same manner as in Example 3 (1), making use of the aforementioned Gene Amp® PCR Reagent Kit and using the SacII primer prepared in Example 4 (1) and the pBR BamHI primer prepared in Example 3 (1) as sense and antisense primers and the aforementioned plasmid pM576 as a template. A portion of the amplified product of the first PCR was applied to 1.5% agarose gel electrophoresis to confirm presence of a single band of interest having a size of about 250 bp. The thus amplified product was extracted and purified by means of phenol treatment and ethanol precipitation, and the thus purified product was digested with SacII and BamHI to obtain a DNA fragment of about 220 bp. The thus obtained DNA fragment of about 220 bp was ligated with a DNA fragment having a size of about 3.4 kb which was prepared from plasmid pM594 by double-digesting it with SacII and BamHI, thereby obtaining an expression plasmid pM576B (cf. FIG. 30). The thus prepared plasmid pM576B was double-digested with HindIII and BamHI, and a DNA fragment of interest having a size of about 300 bp was extracted and purified. Thereafter, the thus purified DNA fragment was subjected to sequencing using the aforementioned DNA sequencer in the same manner as described in Example 2 (2).

The thus confirmed nucleotide sequence of a region of plasmid pM576B from its HindIII site to its BamHI site containing the novel DNA fragment of the present invention and its corresponding amino acid sequence are shown in FIG. 31 (cf. SEQ. I.D. NO.:13 in the SEQUENCE LISTING).

(2) Preparation and culturing of transformant

A transformant, E. coli JE5505 (pM576B), was isolated by transforming E. coli JE5505 with the plasmid pM576B obtained in the above procedure (1), in accordance with Hanahan's method. The thus isolated transformant was subsequently cultured in the same manner as in Example 3 (3) to recover culture supernatant.

The culture supernatant thus prepared was diluted with 0.1% BSA/0.2M triethanolamine-HCl buffer (pH 7.8), and the diluted samples were used for the measurement of trypsin-inhibiting activity in accordance with the procedure described in Example 17 (1). In this instance, culture supernatant of the transformant, E. coli JE5505 (pM463C), obtained in Example 3 (3) was used as a control in the activity measurement. As the results, markedly high trypsin-inhibiting activity was found in the culture supernatant of E. coli JE5505 (pM576B) in comparison with the control.

(3) Purification of the novel polypeptide of the present invention from culture supernatant of E. coli JE5505 (pM576B)

The polypeptide of the present invention was purified from the culture supernatant obtained in the above procedure (2) by means of ammonium sulfate precipitation, gel filtration, anion exchange chromatography and reverse phase chromatography in that order in accordance with the procedure described in Example 2 (4). The thus obtained purified sample was used for the following SDS-PAGE (4), amino acid analysis (5) and activity measurement in Example 17.

(4) SDS-PAGE

The purified polypeptide sample obtained in the above procedure (3) was subjected to SDS-PAGE in accordance with the procedure described in Example 2 (5). After completion of the electrophoresis, staining was carried out with the aforementioned commercial silver staining kit. The purified sample showed a single band by SDS-PAGE.

(5) Determination of amino acid sequence

The purified polypeptide sample obtained in the above procedure (3) was dissolved in 50% acetic acid solution and its amino acid sequence was determined in accordance with the procedure described in Example 2 (6).

As a result, it was confirmed that the purified polypeptide sample obtained in the above procedure (3) is the polypeptide Q19K-AN of the present invention (cf. amino acids 1–68 of SEQ. I.D. NO.:14 of the SEQUENCE LISTING).

Example 9

Production of polypeptide O19R/Y46E

A polypeptide, Q19R/Y46E, having an amino acid sequence derived from the aforementioned formula 1 amino acid sequence by substituting Arg for the 15 position Gln, as well as Glu for the 42 position Tyr, of the formula 1 sequence counting from its N-terminus was prepared in the following manner.

(1) Cloning of DNA fragment

A first PCR was carried out in accordance with the procedure described in Example 3 (1), making use of the aforementioned Gene Amp® PCR Reagent Kit and using the HindIII primer prepared in Example 3 (1) and the Q19R primer prepared in Example 4 (1) as sense and antisense primers and the plasmid pM594 prepared in Example 4 (1) as a template. A portion of the amplified product of the first PCR was applied to 1.5% agarose gel electrophoresis to confirm presence of a band of interest having a size of about 170 bp. The thus amplified product was extracted and purified by means of phenol treatment and ethanol precipitation, and the thus purified DNA fragment was dissolved in TE buffer. Thereafter, a second PCR was carried out in the same manner as the above first PCR using the thus dissolved DNA fragment as a sense primer and the aforementioned plasmid pm575B as a template. In this instance, the pBR BamHI primer prepared in Example 3 (1) was used as an antisense primer. A portion of the amplified product of the second PCR was applied to 1.5% agarose gel electrophoresis to confirm presence of a band of interest having a size of about 350 bp. The thus amplified product was then extracted and purified by means of phenol treatment and ethanol precipitation to obtain the DNA fragment of the present invention.

(2) Construction of expression vector

Figure 32:
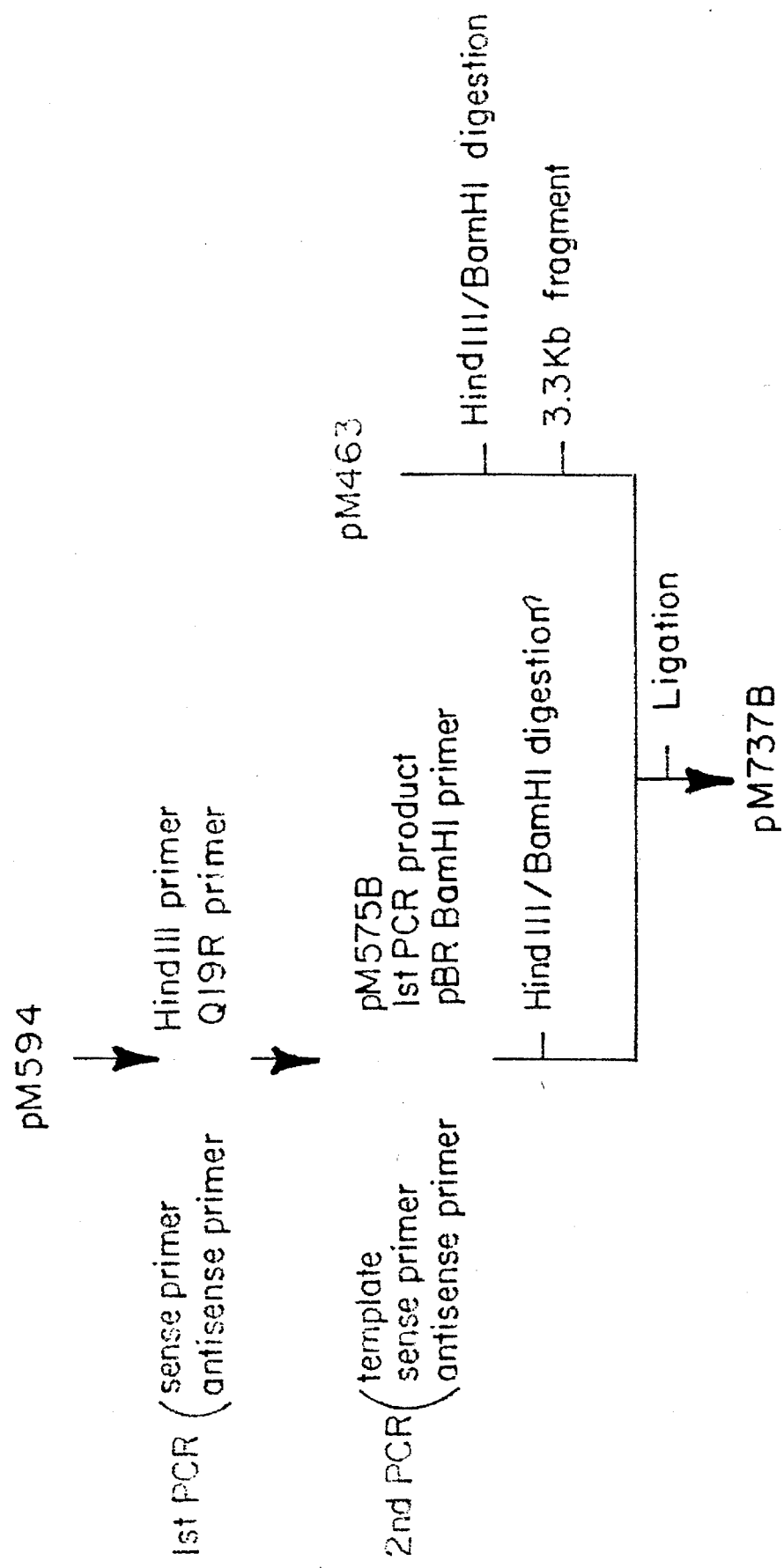
FIG. 32 is a schematic of a process for the construction of plasmid pM737B.

The DNA fragment of the present invention having a size of about 350 bp prepared in the above step (1) was inserted into plasmid pM463 in the same manner as in Example 3 (2) to obtain an expression plasmid pM737B (cf. FIG. 32). The thus obtained expression plasmid pM737B was double-digested with HindIII and BamHI, and a DNA fragment of interest having a size of about 300 bp was extracted and purified. The thus purified DNA fragment of interest was subjected to sequencing using the aforementioned DNA sequencer in the same manner as in Example 2 (2).

The thus confirmed nucleotide sequence of a region of plasmid pM737B from its HindIII site to its BamHI site containing the novel DNA fragment of the present invention and its corresponding amino acid sequence are shown in FIG. 33 (cf. SEQ. I.D. NO.:15 in the SEQUENCE LISTING).

(3) Preparation and culturing of transformant

A transformant, E. coli JE5505 (pM737B), was isolated by transforming E. coli JE5505 with the plasmid pM737B obtained in the above procedure (2), in accordance with Hanahan's method. The thus isolated transformant was subsequently cultured in the same manner as in Example 3 (3) to recover culture supernatant.

The culture supernatant thus prepared was diluted with 0 1% BSA/0.2M triethanolamine-HCl buffer (pH 7.8), and the diluted samples were used for the measurement of trypsin-inhibiting activity in accordance with the procedure described in Example 17 (1). In this instance, culture supernatant of a transformant, E. coli JE5505 (pM463C), obtained in Example 3 (3) was used as a control in the activity measurement. Markedly high trypsin-inhibiting activity was found in the culture supernatant of E. coli JE5505 (pM737B) in comparison with the control.

(4) Purification of the novel polypeptide of the present invention from culture supernatant of E. coli JE5505 (pM737B)

The polypeptide of the present invention was purified from the culture supernatant obtained in the above procedure (3) by means of ammonium sulfate precipitation, gel filtration, anion exchange chromatography and reverse phase chromatography in accordance with the procedure described in Example 2 (4). The thus purified polypeptide sample was used for the following SDS-PAGE (5), amino acid analysis (6) and activity measurement in Example 17.

(5) SDS-PAGE

The purified polypeptide sample obtained in the above procedure (4) was subjected to SDS-PAGE in accordance with the procedure described in Example 2 (5). After the electrophoresis, staining was carried out with the aforementioned commercial silver staining kit. The purified sample showed a single band by SDS-PAGE.

(6) Determination of amino acid sequence

The purified polypeptide sample obtained in the above procedure (4) was dissolved in 50% acetic acid solution and its amino acid sequence was determined in accordance with the procedure described in Example 2 (6).

As a result, it was confirmed that the purified polypeptide sample obtained in the above procedure (4) is the polypeptide Q19R/Y46E (cf. amino acids 1–68 of SEQ. I.D. NO.:16 of the SEQUENCE LISTING).

Example 10

Production of polypeptide Q19K/Y46D

A polypeptide, Q19K/Y46D, having an amino acid sequence derived from the aforementioned formula 1 amino acid sequence by substituting Lys for the 15 position Gln, as well as Asp for the 42 position Tyr, of the formula 1 sequence counting from its N-terminus was prepared in the following method.

(1) Construction of plasmid pM748

PCR was carried out twice in accordance with the procedure described in Example 3 (1) using a plasmid pM710 as a template. In this instance, the plasmid pM710 was prepared in the following method. That is, a DNA fragment represented by the nucleotide sequence of linker 710 (SEQ. I.D. NO.:61) shown in FIG. 34 was divided and designed into 5 small fragments, and each of the thus designed fragments was synthesized chemically in accordance with the procedure described in Example 1, making use of the aforementioned chemical synthesizer. Separately from this, the plasmid pM594 prepared in Example 4 (1) was double-digested with HindIII and ApaI to obtain a DNA fragment of about 3.2 kbp. The thus obtained DNA fragment was ligated with the chemically synthesized DNA fragment, making use of the aforementioned T4 DNA ligase, to obtain the expression plasmid pM710.

PCR was carried out in the following method. A first PCR was carried out using a chemically synthesized Y46D primer (FIG. 35, SEQ. I.D. NO.:62) as a sense primer and the pBR BamHI primer prepared in Example 3 (1) as an antisense primer. A portion of amplified product of the first PCR was applied to 1.5% agarose gel electrophoresis to confirm formation of a DNA fragment of interest having a size of about 120 bp. The thus amplified product was extracted and purified by means of phenol treatment and ethanol precipitation and then dissolved in TE buffer.

Thereafter, a second PCR was carried out using the thus dissolved DNA fragment as an antisense primer and the HindIII primer prepared in Example 3 (1) as a sense primer. Thereby a portion of amplified product of the second PCR was applied to 1.5% agarose gel electrophoresis to confirm formation of a DNA fragment of interest having a size of about 380 bp.

The thus obtained amplified product was then extracted and purified by means of phenol treatment and ethanol precipitation. Then, the DNA fragment was inserted into the aforementioned plasmid pM463 in accordance with the procedure described in Example 3 (2) to obtain the expression plasmid pM748.

(2) Construction of plasmid pM727

PCR was carried out in the same manner as in Example 3 (1) using the thus obtained plasmid pM748 as a template. A first PCR was carried out using the HindIII primer and the Q19K primer prepared in Example 3 (1) as a sense and antisense primers, respectively. A portion of the amplified product of the first PCR was applied to 1.5% agarose gel electrophoresis to confirm formation of a DNA fragment of interest having a size of about 210 bp. The thus amplified product was then extracted and purified by means of phenol treatment and ethanol precipitation and then dissolved in TE buffer. Thereafter, a second PCR was carried out using the thus dissolved DNA fragment as a sense primer and the pBRBamHI primer prepared in Example 3 (1) as an antisense primers. Thereby a portion of amplified produce of the second PCR was applied to 1.5% agarose gel electrophoresis to confirm formation of a DNA fragment of interest having a size of about 380 bp.

The thus amplified produce was then extracted and purified by means of phenol treatment and ethanol precipitation to obtain the DNA fragment of the present invention.

The thus obtained DNA fragment of interest having a size of about 380 bp was inserted into the aforementioned plasmid pM463 in accordance with the procedure described in Example 3 (2) to obtain the expression plasmid pM727. The thus constructed plasmid pM727 was double-digested with HindIII and BamHI, and a fragment of interest having a size of about 340 bp was extracted and purified. Thereafter, sequencing was carried out in the same manner as described in Example 2 (2) using the aforementioned DNA sequencer.

The confirmed nucleotide sequence of a region of plasmid pM727 from its HindIII site to its BamHI size containing the novel DNA fragment of the present invention and its corresponding amino acid sequence are shown in FIG. 36 (cf. SEQ. I.D. NO.:17 in the SEQUENCE LISTING).

(3) Preparation and culturing of transformant

A transformant, E. coli JE5505 (pM727), was isolated by transforming E. coli JE5505 with the plasmid pM727 obtained in the above procedure (2), in accordance with Hanahan's method. The thus isolated transformant was subsequently cultured in the same manner as in Example 3 (3). The resulting culture medium was concentrated using an ultrafiltration membrane, Benchmark GX membrane (Menbre Inc. pore size 0.2 μm), thereafter the thus concentrated sample was centrifuged at 10,000×g for 20 minutes at 4° C. to recover the cells.

(4) Solubilization and reduction

The cells obtained in the above procedure (2) were suspended in 0.5% Triton X-100/10 mM EDTA solution and homogenized using high pressure laboratory homogenizer (RANNI a/s.) with 800 bar. The thus treated suspension was centrifuged at 10,000×g for 20 minutes at 4° C. to recover the inclusion bodies.

The pellet was suspended by 0.5% Triton X-100/10 mM EDTA solution and then it was centrifuged again. After repeating centrifugation twice in the same procedure as above, the pellet was recovered. The thus obtained pellet was redissolved by an appropriate amount of a solubilization buffer (5M guanidine hydrochloride, 0.005% Tween 80, 50 mM Tris-HCl (pH 8.0), 5 mM EDTA, 2 mM glutathione in reduced form and 0.02 mM glutathione in oxidized form). And then 2-mercaptoethanol was added to the solution to final concentration 50 μM. The thus prepared solution was stirred overnight at 4° C. and thereafter concentrated by ultrafiltration using a membrane, YM-5 (Grace Japan) followed by filtration using a filter of 0.44 μm pore size.

The resulting filtrate was applied to a column (5 cmIIx95 cm) packed with Sephacryl S-100 HR (Pharmacia) which had been equilibrated with the aforementioned solubilization buffer. The loaded sample was then eluted using the same buffer at a flow rate of 3.5 ml/min and each 30 ml fraction was collected. During the elution, protein concentration was monitored at 280 nm. A portion of each collected fraction was subjected to SDS-PAGE. After staining with Coomassie Brilliant Blue, fractions with a desired molecular weight were pooled.

The pooled fraction was diluted with the aforementioned solubilization buffer to 0.5 mg/ml. The solution was used as a sample for the following refolding treatment.

(5) Refolding

Refolding was carried out by dialyzing the sample obtained in the above procedure (3) under the following conditions. That is, the sample was dialyzed against two changes of 10 to 15 volumes of solubilization buffer which lacked guanidine hydrochloride, followed by additional two changes of 10 to 15 volumes of distilled water. After the dialysis, the sample was adjusted to pH 2 with HCl and subjected to the following purification process.

(6) Purification
(a) Reverse phase chromatography

The sample obtained from the above procedure (5) was applied a PLRP-S column (25 mmIIx150 mm, Polymer Laboratories) which had been equilibrated with 0.1% TFA solution. Elution was carried out an a flow rate of 5 ml/min with a linear gradient of 0–70% acetonitrile/0.1% TFA/30 min, 70–100% acetonitrile/0.1% TFA/3 min. Protein concentration in the eluent was monitored at 280 nm and each 5 ml fraction was collected. A portion of each collected fraction was checked for its trypsin-inhibiting activity in accordance with the procedure of Example 17 (1). Fractions showing the trypsin-inhibiting activity were pooled, lyophilized and then dissolved in 70% formic acid to a final concentration of about 100 μM. The resulting solution was mixed with 2,000 times higher molar ratio of cyanogen bromide and then incubated in the dark for 24 hours at 25° C. The thus treated solution was diluted with 2 volumes of distilled water.

(b) Cation exchange chromatography

The sample obtained in the above step (a) was applied to a SP-Toyopearl column (30 mmIIx150 mm, Tosoh Corp.) which had been equilibrated with 10% formic acid solution. Using a FPLC system, elution was carried out at a flow rate of 8 ml/min with a linear gradient of NaCl (NaCl concentration 0–1.2M/10 min). Protein concentration in the eluent was monitored by measuring absorbance at 280 nm and 32 ml fractions were collected. A portion of each collected fraction was checked for its trypsin-inhibiting activity in accordance with the procedure described in Example 16 (1). A fraction showing the activity was used in the following reverse phase chromatography.

(c) Reverse phase chromatography

The active fraction obtained in the above step (b) was applied to the aforementioned PLRP-S column (25 mmIIx 150 mm) which had been equilibrated with 0.1% TFA solution. Elution was carried out at a flow rate of 10 ml/min with a linear gradient of 0–70% acetonitrile/0.1% TFA/15 min and 70–100% acetonitrile/0.1% TFA/5 min. Protein concentration in the eluent was monitored at 280 nm and each protein peak was collected.

A portion of each collected fraction was checked for its trypsin-inhibiting activity in accordance with the procedure of Example 17 (1). Fractions showing the trypsin-inhibiting activity were pooled and lyophilized to obtain a purified sample.

(7) SDS-PAGE

The purified polypeptide sample obtained in the above procedure (6) was subjected to SDS-PAGE in accordance with the procedure described in Example 2 (5). After the electrophoresis, staining was carried out with the aforementioned commercial silver staining kit. The purified sample showed a single band by SDS-PAGE.

(8) Determination of amino acid sequence

A portion of the purified polypeptide sample obtained in the above procedure (7) was dissolved in 50% acetic acid solution and its amino acid sequence was determined in accordance with the procedure described in Example 2 (6). As a result, it was confirmed that the purified sample is the polypeptide Q19K/Y46D of the present invention (cf. amino acids 34–101 to SEQ. I.D. NO.:18 and SEQ. I.D. NO.:35 of the SEQUENCE LISTING).

Example 11

Production of polypeptide O19R/Y46D

A polypeptide, Q19R/Y46D, having an amino acid sequence derived from the aforementioned formula 1 amino acid sequence by substituting Arg for the 15 position Gln, as well as Asp for the 42 position Tyr, of the formula 1 sequence counting from its N-terminus was prepared in the following method.

(1) Construction of plasmid pM744

PCR was carried out twice using the plasmid pM748 obtained in Example 10 (1) as a template, in accordance with the procedure described in Example 3 (1). In this incidence the first PCR was carried out using the Q19R primer prepared in Example 4 (1) as an antisense primer instead of the Q19K primer. A finally obtained amplified product of interest having a size of about 380 bp was extracted and purified by means of phenol treatment and ethanol precipitation to obtain the DNA fragment of the present invention.

The thus obtained DNA fragment was inserted into the aforementioned plasmid pM463 in accordance with the procedure described in Example 3 (2) to obtain the expression plasmid pM744. The thus concentrated plasmid pM744 was double-digested with HindIII and BamHI, and a DNA fragment of interest having a size of about 340 bp was extracted and purified. Thereafter, sequencing was carried out in the same manner as described in Example 2 (2) using the aforementioned DNA sequencer.

The confirmed nucleotide sequence of a region of plasmid pM744 from its HindIII site to its BamHI site containing the novel DNA fragment of the present invention and its corresponding amino acid sequence are shown in FIG. 37 (cf. SEQ I.D. NO.:19 in the SEQUENCE LISTING).

(2) Preparation and culturing of transformant

A transformant, *E. coli* JE5505 (pM744), was isolated by transforming *E. coli* JE5505 with the plasmid pM744 obtained in the above procedure (1), in accordance with Hanahan's method. The thus isolated transformant was subsequently cultured in the same manner as in Example 3 (3), to recover cultured medium. The resulting cultured medium was concentrated using the aforementioned ultrafiltration membrane, Benchmark GX membrane, thereafter the thus concentrated sample was centrifuged at 10.000×g for 20 minutes at 4° C. to recover the cells.

(3) Isolation and purification of Q19R/Y46D

Inclusion bodies were obtained in the above procedure (2) in the form of pellet which was subsequently subjected to solubilization and reduction treatments in the same manner as described in Example 10 (4). After the treatment, the sample was refolded in the same manner as described in Example 10 (5) and then purified in the same manner as in Example 10 (6). The finally obtained active fraction was lyophilized to obtain a purified sample.

(4) SDS-PAGE

A portion of the purified polypeptide sample obtained in the above procedure (3) was subjected to SDS-PAGE in accordance with the procedure described in Example 2 (5). After the electrophoresis, staining was carried out with the aforementioned commercial silver staining kit. The purified sample showed a single band by SDS-PAGE.

(5) Determination of amino acid sequence

The purified polypeptide sample obtained in the above procedure (3) was dissolved in 50% acetic acid solution and its amino acid sequence was determined in accordance with the procedure described in Example 2 (6). As a result, it was confirmed that the purified polypeptide sample obtained in the above procedure (3) is the polypeptide Q19R/Y46D of the present invention (cf. amino acids 34–101 of SEQ. I.D. NO.:20 and SEQ. I.D. NO.:36 of the SEQUENCE LISTING).

Example 12

Production of polypeptide R11O/O19K/Y46D

A polypeptide, R11Q/Q19K/Y46D, having an amino acid sequence derived from the aforementioned formula 1 amino acid sequence by substituting Gln for the 11 position Arg, Lys for the 15 position Gln, as well as Asp for the 42 position Tyr, of the formula 1 sequence counting from its N-terminus was prepared in the following method.

(1) Construction of plasmid pM741

PCR was carried out twice using the plasmid pM727 obtained in Example 10 (2) as a template, in accordance with the procedure described in Example 3 (1). In this instance the first PCR was carried out using a chemically synthesized primer R11Q (FIG. 38) as an antisense primer instead of the Q19K primer. A finally obtained amplified product of interest having a size of about 380 bp was extracted and purified by means of phenol treatment and ethanol precipitation to obtain the DNA fragment of the present invention.

The thus obtained DNA fragment was inserted into the aforementioned plasmid pM463 in accordance with the procedure described in Example 3 (2) to obtain the expression plasmid pM741. The thus constructed plasmid pM741 was double-digested with HindIII and BamHI, and a DNA fragment of interest having a size of about 340 bp was extracted and purified. Thereafter, sequencing was carried out in the same manner as described in Example 2 (2) using the aforementioned DNA sequencer.

The confirmed nucleotide sequence of a region of plasmid pM741 from its HindIII site to its BamHI site containing the novel DNA fragment of the present invention and corresponding amino acid sequence are shown in FIG. 39 (cf. SEQ. I.D. NO.:21 in the SEQUENCE LISTING).

(2) Preparation and culturing of transformant

A transformant, *E. coli* JE5505 (pM741), was isolated by transforming *E. coli* JE5505 with the plasmid pM741 obtained in the above procedure (1), in accordance with Hanahan's method. The thus isolated transformant was subsequently cultured in the same manner as in Example 3 (3) to recover cultured medium. A portion of the resulting cultured medium was centrifuged to obtain supernatant and to check its trypsin-inhibiting activity in accordance with the procedure of Example 17 (1) .

The trypsin-inhibiting activity in the obtained supernatant was 5 times higher than that of *E. coli* JE5505 (pM727). In consideration of the specific activity bovine trypsin-inhibition, it was confirmed that the substitution of the 7 position counting from N-terminus of the amino acid sequence of formula 1 provided for efficient secretion of this polypeptide from a transformant.

The rest of culture mixture was concentrated using the aforementioned ultrafiltration membrane, Benchmark GX membrane. Thereafter the concentrated sample was centrifuged at 10,000×g for 20 minutes at 4° C. to recover the cells.

(3) Isolation and purification of R11Q/Q19K/Y46D

Inclusion bodies were obtained in the above procedure (2) in the form of pellet which were subsequently subjected to solubilization and reduction treatments in the same manner as described in Example 10 (4) . After the treatment, the sample was refolded in the same manner as described in Example 10 (5) and then purified in the same manner as in Example 10 (6). Finally obtained active fraction was lyophilized to obtain a purified sample.

(4) SDS-PAGE

A pork ion of the purified polypeptide sample obtained in the above procedure (3) was subjected to SDS-PAGE in accordance with the procedure described in Example 2 (5). After the electrophoresis, staining was carried out with the aforementioned commercial silver staining kit. The purified sample showed a single band by SDS-PAGE.

(5) Determination of amino acid sequence

The purified polypeptide sample obtained in the above procedure (3) was dissolved in 50% acetic acid solution and its amino acid sequence was determined in accordance with the procedure described in Example 2 (6). As a result, it was confirmed that the purified polypeptide sample obtained in the above procedure (3) is the polypeptide R11Q/Q19K/Y46D of the present invention (cf. amino acids 34–101 of SEQ. I.D. NO.:22 and SEQ. I.D. NO.:37 of the SEQUENCE LISTING).

Example 13

Production of polypeptide R11D/O19K/Y46D

A polypeptide, R11D/Q19K/Y46D, having an amino acid sequence derived from the aforementioned formula 1 amino acid sequence by substituting Arg for the 11 position Asp, Lys for the 15 position Gln, as well as Asp for the 42 position Tyr, of the formula 1 sequence counting from its N-terminus side was prepared in the following method.

(1) Construction of plasmid pM742

PCR was carried out twice using the plasmid pM727 obtained in Example 10 (2) as a template, in accordance with the procedure described in Example 3 (1). In this instance the first PCR was carried out using a chemically synthesized primer R11D (FIG. 40) as an antisense primer instead of the Q19K primer. A finally obtained amplified product of interest having a size of about 380 bp was extracted and purified by means of phenol treatment and ethanol precipitation to obtain the DNA fragment of the present invention.

The thus obtained DNA fragment was inserted into the aforementioned plasmid pM463 in accordance with the procedure described in Example 3 (2) to obtain the expression plasmid pM742. The thus constructed plasmid pM742 was double-digested with HindIII and BamHI, and a DNA fragment of interest having a size of about 340 bp was extracted and purified. Thereafter, sequencing was carried out in the same manner as described in Example 2 (2) using the aforementioned DNA sequencer.

The confirmed nucleotide sequence of a region of plasmid pM742 from its HindIII site to its BamHI site containing the novel DNA fragment of the present invention and its corresponding amino acid sequence are shown in FIG. 41 (cf. SEQ. I.D. NO.:23 in the SEQUENCE LISTING).

(2) Preparation and culturing of transformant

A transformant, E. coli JE5505 (pM742), was isolated by transforming E. coli JE5505 with the plasmid pM742 obtained in the above procedure (1), in accordance with Hanahan's method. The thus isolated transformant was subsequently cultured in the same manner as in Example 3 (3) to recover cultured medium. A portion of the resulting cultured medium was centrifuged to obtain supernatant and to check its trypsin-inhibiting activity in accordance with the procedure of Example 17 (1).

The trypsin-inhibiting activity in the obtained supernatant was 2 times higher than that of E. coli JE5505 (pM727). In consideration of the specific activity in bovine trypsin inhibition of this polypeptide, it was confirmed that the substitution of the 7 position counting from N-terminus of the amino acid sequence of formula 1 provided for efficient secretion of this polypeptide from a transformant.

The rest of cultured medium was concentrated using the aforementioned ultrafiltration membrane, Benchmark GX membrane. Thereafter the concentrated sample was centrifuged at 10,000×g for 20 minutes at 4° C. to recover the cells.

(3) Isolation and purification of R11D/Q19K/Y46D

Inclusion bodies were obtained in the above procedure (2) in the form of a pellet which was subsequently subjected to solubilization and reduction treatments in the same manner as described in Example 10 (4). After the treatment, the sample was refolded in the same manner as described in Example 10 (5) and then purified in the same manner as in Example 10 (6). The finally obtained active fraction was lyophilized to obtain a purified sample.

(4) SDS-PAGE

A portion of the purified polypeptide sample obtained in the above procedure (3) was subjected to SDS-PAGE in accordance with the procedure described in Example 2 (5). After the electrophoresis, staining was carried out with the aforementioned commercial silver staining kit. The purified sample showed a single band by SDS-PAGE.

(5) Determination of amino acid sequence

The purified polypeptide sample obtained in the above procedure (3) was dissolved in 50% acetic acid solution and its amino acid sequence was determined in accordance with the procedure described in Example 2 (6). As a result, it was confirmed that the purified polypeptide sample obtained in the above procedure (3) is the polypeptide R11D/Q19K/Y46D of the present invention (cf. amino acids 34–101 of SEQ. I.D. NO.:24 and SEQ. I.D. NO.:38 of the SEQUENCE LISTING).

Example 14

Production of polypeptide R11L/O19K/Y46D

A polypeptide, R11L/Q19K/Y46D, having an amino acid sequence derived from the aforementioned formula 1 amino acid sequence by substituting Leu for the 11 position Arg, Lys for the 15 position Gln, as well as Asp for the 42 position Tyr, of the formula 1 sequence counting from its N-terminus side was prepared in the following method.

(1) Construction of plasmid pM743

PCR was carried out twice using the plasmid pM727 obtained in Example 10 (2) as a template, in accordance with the procedure described in Example 3 (1). In this instance the first PCR was carried out using a chemically synthesized primer R11L (FIG. 42) as an antisense primer instead of the Q19K primer. A finally obtained amplified product of interest having a size of about 380 bp was extracted and purified by means of phenol treatment and ethanol precipitation to obtain the DNA fragment of the present invention.

The thus obtained DNA fragment was inserted into the aforementioned plasmid pM463 in accordance with the procedure described in Example 3 (2) to obtain the expression plasmid pM743. The thus constructed plasmid pM743 was double-digested with HindIII and BamHI, and a DNA fragment of interest having a size of about 340 bp was extracted and purified. Thereafter, sequencing was carried out in the same manner as described in Example 2 (2) using the aforementioned DNA sequencer.

The confirmed nucleotide sequence of a region of plasmid pM743 from its HindIII site to its BamHI site containing the novel DNA fragment of the present invention and its corresponding amino acid sequence are shown in FIG. 43 (cf. SEQ. I.D. No.:25 in the SEQUENCE LISTING).

(2) Preparation and culturing of transformant

A transformant, E. coli JE5505 (pM743), was isolated by transforming E. coli JE5505 with the plasmid pM743 obtained in the above procedure (1), in accordance with Hanahan's method. The thus isolated transformant was subsequently cultured in the same manner as in Example 3 (3) to recover cultured medium.

The resulting cultured medium was concentrated using the aforementioned ultrafiltration membrane, Benchmark GX membrane. Thereafter the concentrated sample was centrifuged at 10,000×g for 20 minutes at 4° C. to recover the cells.

(3) Isolation and purification of R11L/Q19K/Y46D

Inclusion bodies were obtained in the above procedure (2) in the form of a pellet which was subsequently subjected to solubilization and reduction treatments in the same manner as described in Example 10 (4). After the treatment, the sample was refolded in the same manner as described in Example 10 (5), and then purified in the same manner as in Example 10 (6). The finally obtained active fraction was lyophilized to obtain a purified sample.

(4) SDS-PAGE

A portion of the purified polypeptide sample obtained in the above procedure (3) was subjected no SDS-PAGE in accordance with the procedure described in Example 2 (5). After the electrophoresis, staining was carried out with the aforementioned commercial silver staining kit. The purified sample showed a single band by SDS-PAGE.

(5) Determination of amino acid sequence

The purified polypeptide sample obtained in the above procedure (3) was dissolved in 50% acetic acid solution and its amino acid sequence was determined in accordance with the procedure described in Example 2 (6). As a result, it was confirmed that the purified polypeptide sample obtained in the above procedure (3) is the polypeptide R11L/Q19K/Y46D of the present invention (cf. amino acids 34–101 of SEQ. I.D. NO.:26 and SEQ. I.D. NO.:39 of the SEQUENCE LISTING).

Example 15

Production of polypeptide R11E/O19K/Y46E

A polypeptide, R11E/Q19K/Y46E, having an amino acid sequence derived from the aforementioned formula 1 amino acid sequence by substituting Glu for the position 11 Arg, Lys for the 15 position Gln, as well as Glu for the 42 position Tyr, of the formula 1 sequence counting from its N-terminus side was prepared in the following method.

(1) Construction of plasmid pM721

PCR was carried out twice in accordance with the procedure described in Example 3 (1) using a plasmid pM727 as a template. In this instance, the first PCR was carried out using the Y46E primer prepared in Example 2 (1) and the pBRBamHI primer prepared in Example 3 (1) as sense and antisense primers, respectively. An amplified DNA fragment obtained by the first PCR having a size of about 120 bp was then extracted and purified by means of phenol treatment and ethanol precipitation and then dissolved in TE buffer. Thereafter, a second PCR was carried out using the thus dissolved DNA fragment as an antisense primer and the HindIII primer prepared in Example 3 (1) as a sense primer. Thereby a finally obtained amplified product of interest having a size of about 380 bp was extracted and purified by means of phenol treatment and ethanol precipitation. Then, the DNA fragment was inserted into the aforementioned plasmid pM463 in accordance with the procedure described in Example 3 (2) to obtain the expression plasmid pM721.

(2) Construction of plasmid pM738

PCR was carried out twice using the thus obtained plasmid pM721, in accordance with the procedure described in Example 3 (1). In this instance, the first PCR was carried out using the R11E primer prepared in Example 6 (1) as an antisense primer instead of the Q19K primer. A finally obtained amplified product of interest having a size of about 380 bp was extracted and purified by means of phenol treatment and ethanol precipitation to obtain the DNA fragment of the present invention.

Thus obtained DNA fragment was inserted into the aforementioned plasmid pM463 in accordance with the procedure described in Example 3 (2) to obtain the expression plasmid pM738. The thus constructed plasmid pM738 was double-digested with HindIII and BamHI, and a DNA fragment of interest having a size of about 340 bp was extracted and purified. Thereafter, sequencing was carried out in the same manner as described in Example 2 (2) using the aforementioned DNA sequencer.

The confirmed nucleotide sequence of a region of plasmid pM738 from its HindIII site to its BamHI site containing the novel DNA fragment of the present invention and its corresponding amino acid sequence are shown in FIG. 44 (SEQ. I.D. NO.:27 of the SEQUENCE LISTING).

(3) Preparation and culturing of transformant

A transformant, E. coli JE5505 (pM738), was isolated by transforming E. coli JE5505 with the plasmid pM738 obtained in the above procedure (2), in accordance with Hanahan's method. The thus isolated transformant was subsequently cultured in the same manner as in Example 3 (3) to recover cultured medium. A portion of the resulting cultured medium was centrifuged to obtain supernatant and to check its trypsin-inhibiting activity in accordance with the procedure of Example 17 (1).

The trypsin-inhibiting activity in the obtained supernatant was about 5 times higher than that of E. coli JE5505 (pM721) which was transformed by the plasmid pM721 obtained in above (1). In consideration of the specific activity of this polypeptide in bovine trypsin inhibition, it was confirmed that the substitution of the 7 position counting from N-terminus of the amino acid sequence formula 1 provides for efficient secretion of this polypeptide from a transformant.

The rest of cultured medium was concentrated using the aforementioned ultrafiltration membrane, Benchmark GX membrane. Thereafter the concentrated sample was centrifuged at 10,000×g for 20 minutes at 4° C. to recover the cells.

(4) Isolation and purification of R11E/Q19K/Y46E

Inclusion bodies were obtained in the above procedure (3) in the form of a pellet which was subsequently subjected to solubilization and reduction treatments in the same manner as described in Example 10 (4). After the treatment, the sample was refolded in the same manner as described in Example 10 (5) and then purified in the same manner as in Example 10 (6). The finally obtained active fraction was lyophilized to obtain a purified sample.

(5) SDS-PAGE

A portion of the purified polypeptide sample obtained in the above procedure (3) was subjected to SDS-PAGE in accordance with the procedure described in Example 2 (5). After the electrophoresis, staining was carried out with the aforementioned commercial silver staining kit. The purified sample showed a single band by SDS-PAGE.

(6) Determination of amino acid sequence

The purified polypeptide sample obtained in the above procedure (4) was dissolved in 50% acetic acid solution and its amino acid sequence was determined in accordance with the procedure described in Example 2 (6). As a result, it was confirmed that the purified polypeptide sample obtained in the above procedure (3) is the aimed polypeptide R1E/Q19K/Y46E of the present invention (cf. amino acids 34–101 of SEQ. I.D. NO.:28 and SEQ. I.D. NO.:39 of the SEQUENCE LISTING).

Example 16

Production of polypeptide R11N/O19K/Y46D, R11S/O19K/Y46D and R11A/O19K/Y46D

Polypeptides R11N/Q19K/Y46D, R11S/Q19K/Y46D and R11A/Q19K/Y46D having an amino acid sequence derived from the aforementioned formula 1 amino acid sequence by substituting Asn, Ser and Ala for the 7 position Arg, respectively, in addition to substituting Lys for the 15 position Gln and Asp for the 42 position Tyr of the formula 1 sequence counting from its N-terminus side were prepared by the following method.

That is, DNA fragments which have a nucleotide sequence coding the amino acid sequence of polypeptides R11N/Q19K/Y46D, R11S/Q19K/Y46D, R11A/Q19K/Y46D (cf. SEQ. I.D. NO.:41, 42, and 43 respectively, were prepared by the site-directed mutagenesis, the method of Landt et. al. The thus obtained DNA fragments were inserted into the aforementioned plasmid pM463 in accordance with the procedure described in Example 3 (2) to obtain the expression plasmid pM764, pM765, pM767 and sequencing was carried out in the same manner as described in Example 2 (2).

The confirmed nucleotide sequences of each region of plasmid pM764, pM765 and pM767 from their HindIII sites to their BamHI sites containing novel DNA fragments of the present invention and those corresponding amino acid sequences are shown in Sequence I.D. Nos. 29, 31 and 33 in the SEQUENCE LISTING. *E. coli* JE5505 were transformed with the plasmid pM764, pM765 and pM767 respectively, in accordance with Hanahan's method. And then transformants, *E. coli* JE5505 (pM764), *E. coli* JE5505 (pM765), *E. coli* JE5505 (pM767) were isolated and cultured in the same manner as described in Example 3 (3). A portion of the cultured medium of each transformant was centrifuged to obtain supernatant and to check its trypsin-inhibiting activity in accordance with the procedure of Example 17 (1).

All of the obtained supernatant showed about 4 times higher trypsin-inhibiting activity in comparison with that of *E. coli* JE5505 (pM727). In consideration of the specific activity of these polypeptides in bovine trypsin inhibition, it was confirmed that these substitutions of 7 position counting from N-terminus of the amino acid sequence formula 1 provides for efficient secretion of this polypeptide from a transformant.

Example 17

Measurement of enzyme-inhibiting activities

Trypsin-, FXa- and elastase-inhibiting activities of the novel polypeptide of the present invention were measured in the following manner, using polypeptide samples Y46E, Q19K, Q19R, Q19K/Y46E, R11E/Y46E, Y46E-AN, Q19K-AN, Q19R/Y46E, Q19K/Y46D, Q19R/Y46D, R11Q/Q19K/Y46D, R11D/Q19K/Y46D, R11L/Q19K/Y46D, R11E/Q19K/Y46E, R11N/Q19K/Y46D, R11S/Q19K/Y46D and R11A/Q19K/Y46D obtained in Example 2 4), Example 3 (4), Example 4 (4), Example 5 (4), Example 6 (4), Example 7 (3), Example 8 (3), Example 9 (4), Example 10 (6), Example 11 (3), Example 12 (3), Example 13 (3), Example 14 (3), Example 15 (4) and Example 16, respectively.

(1) Trypsin-inhibiting activity

The purified polypeptide of the present invention was dissolved in 100 μl of distilled water, and the solution was serially diluted with a 0.1% BSA/0.2M triethanolamine-HCl buffer (pH 7.8) for use in the activity measurement. Measurement of the trypsin-inhibiting activity in the thus prepared test sample was carried out in accordance with Kassel's method (Kassel, B et al., *Methods in Enzymology*, vol. 19, pp. 844–852, 1970) using a synthetic substrate S-2444 (Daiichi Pure Chemicals Co., Ltd.).

Bovine trypsin (Type XIII, Sigma Chemical Co.) was dissolved in 0.001M HCl to a final concentration of 13,600 BAEEU/ml and the solution was further diluted with the 0.1% BSA/0.2M triethanolamine-HCl buffer (pH 7.8) to prepare 1.2 BAEEU/ml of trypsin Solution. Separately from this, a 2 mM solution of the synthetic substrate S-2444 was prepared by dissolving it in distilled water. Next, 100 μl of the test sample was mixed with 100 μl of the trypsin solution. After incubating statically at 37° C. for 10 minutes, 50 μl of the S-2444 solution was added to start the reaction. The reaction was carried out at 37° C. for 15 minutes and then stopped by adding 50 μl of 50% acetic acid solution to the reaction mixture. Thereafter, absorbance at a wavelength of 405 nm was measured using a spectrophotometer. In this instance, in order to eliminate absorbancy of various contents in the reaction mixture other than the reaction product, a blank solution was prepared by mixing 100 μl of the bovine trypsin solution with 50 μl of 50% acetic acid and then with 100 μl of each test sample and 50 μl of the S-2444 solution. Thus, it was confirmed that each of these polypeptides Q19K, Q19R, Q19K/Y46E, R11E/Y46E, Y46E-AN, Q19K-AN, Q19R/Y46E, Q19K/Y46D, Q19R/Y46D, R11Q/Q19K/Y46D, R11D/Q19K/Y46D, R11L/Q19K/Y46D, R11E/Q19K/Y46E, R11N/Q19K/Y46D, R11S/Q19K/Y46D and R11A/Q19K/Y46D can inhibit bovine trypsin in a concentration-dependent manner.

(2) Human trypsin-inhibiting activity

The purified polypeptide of the present invention was dissolved in 100 μl of distilled water. The concentration of polypeptide in the thus prepared solution was determined based on its bovine trypsin-inhibiting activity measured in accordance with the above procedure (1) using UTI (Mochida Pharmaceutical Co., Ltd.; cf. H. Ohnishi et al., *Nippon Yakurigaku Zasshi*, vol. 85, pp. 1–6, 1985) as a standard. The polypeptide solution was then diluted to various concentration levels with 0.03% BSA/0.2M triethanolamine-HCl buffer (pH 7.8) for use in the activity measurement. Separately from this, human trypsin (Calbiochem) was dissolved in 1 mM HCl to a concentration of 1,000 SU/ml and the solution was further diluted with the 0.03% BSA/0.2M triethanolamine-HCl buffer (pH 7.8) to prepare a 1.25 SU/ml solution of human trypsin. Thereafter, human trypsin-inhibiting activity was measured in the same manner as described in the above procedure (1) using the aforementioned synthetic substrate S-2444. Thus, it was confirmed that each of these polypeptides Q19K, Q19R, Q19K/Y46E, R11E/Y46E, Y46E-AN, Q19K-AN, Q19R/Y46E, Q19K/Y46D, Q19R/Y46D R11Q/Q19K/Y46D, R11D/Q19K/Y46D, R11L/Q19K/Y46D, R11E/Q19K/Y46E, R11N/Q19K/Y46D, R11S/Q19K/Y46D and R11A/Q19K/Y46D can inhibit human trypsin in a concentration-dependent manner.

(3) FXa-inhibiting activity

The purified polypeptide of the present invention was dissolved in 100 μl of distilled water. Polypeptide concentration of this solution was determined based on its bovine trypsin-inhibiting activity measured in accordance with the above procedure (1) using the aforementioned UTI as a standard. The thus prepared solution was then diluted to various concentration levels with 0.1% BSA/150 mM NaCl/5 mM CaCl$_2$/50 mM Tris-HCl buffer (pH 8.3) for use in the activity measurement. Separately from this, a polypeptide TN70 (cf. Japanese Patent Application No. 3-325220) and polypeptide AN68 were purified respectively in accordance with the procedure of Example 2 (4) from a culture supernatant of *E. coil* JE5505 (pM552) (accession No., FERM BP-3561) and *E. coli* JE5505 (pM594) that was obtained by transforming *E. coil* JE5505 with the aforementioned plasmid pM594 from in Example 4, respectively (1).

The thus purified polypeptide TN70 and AN68 were diluted to various concentration levels to be used as control solutions.

The amino acid sequence of polypeptide TN70 was represented in Formula 3, and amino acid sequence of polypeptide AN68 is represented below, in Formula 5.

Using a synthetic compound S-2222 (Daiichi Pure Chemicals Co., Ltd.) as a substrate, FXa-inhibiting activities in the thus prepared test sample solution and control solutions were measured in accordance with the method of Ohno et al. (Ohno H. et al., *Thromb. Res.*, vol. 19, pp. 579–588, 1980) as follows. First, human FXa (American Diagnostica Inc.) was dissolved in distilled water to a final concentration of 10 PEU/ml and the solution was further diluted with the aforementioned 0.1% BSA/150 mM NaCl/5 mM CACl$_2$/50 mM Tris-HCl buffer (pH 8.3) to prepare 0.1 PEU/ml of FXa solution. Separately from this, a 4 mM solution of S-2222 was prepared by dissolving it in distilled water and the solution was further diluted with the 0.1% BSA/150 mM NaCl/5 mM CACl$_2$/50 mM Tris-HCl buffer (pH 8.3) to obtain a 2 mM solution of S-2222.

Next, 25 µl of the test sample or a control solution was mixed with 100 µl of the 0.1% BSA/150 mM NaCl/5 mM CACl$_2$/50 mM Tris-HCl buffer (pH 8.3) and 25 µl of the FXa solution. After incubating statically at 37° C. for 10 minutes, 100 µl of the S-2222 solution was added no start the reaction. The reaction was carried out at 37° C. for 30 minutes and then stopped by adding 50 µl of 50% acetic acid solution to the reaction mixture. Thereafter, absorbance at a wavelength of 405 nm was measured using a spectrophotometer. In this instance, in order to eliminate absorbancy of various contents in the reaction mixture other than the reaction product, a blank solution was prepared by mixing 25 µl of the FXa solution with 50 µl of 50% acetic acid and then with 25 µl of each test sample or the control solution, 100 µl of the 0.1% BSA/150 mM NaCl/5 mM CACl$_2$/50 mM Tris-HCl buffer (pH 8.3) and with 100 µl of the S-2222 solution.

| Formula 5 (SEQ. I.D. NO.: 76) | | | | | | | | | |
| --- | --- | --- | --- | --- | --- | --- | --- | --- | --- |
| Ala | Ala | Cys | Asn | Leu | Pro | Ile | Val | Arg | Gly |
| Pro | Cys | Arg | Ala | Phe | Ile | Gln | Leu | Trp | Ala |
| Phe | Asp | Ala | Val | Lys | Gly | Lys | Cys | Val | Leu |
| Phe | Pro | Tyr | Gly | Gly | Cys | Gln | Gly | Asn | Gly |
| Asn | Lys | Phe | Tyr | Ser | Glu | Lys | Glu | Cys | Arg |
| Glu | Tyr | Cys | Gly | Val | Pro | Gly | Asp | Gly | Asp |
| Glu | Glu | Leu | Leu | Arg | Phe | Ser | Asn | | |

The results are shown in FIG. 45 to FIG. 53. In these figures, polypeptide concentration in the reaction solution was expressed as its bovine trypsin-inhibiting activity. Also, residual human FXa activity was expressed by percentage based on the absorbance of a control reaction mixture in which 25 µl of the 0.1% BSA/150 mM NaCl/5 mM CACl$_2$/50 mM Tris-HCl buffer (pH 8.3) was used instead of the test sample.

Figure 45:
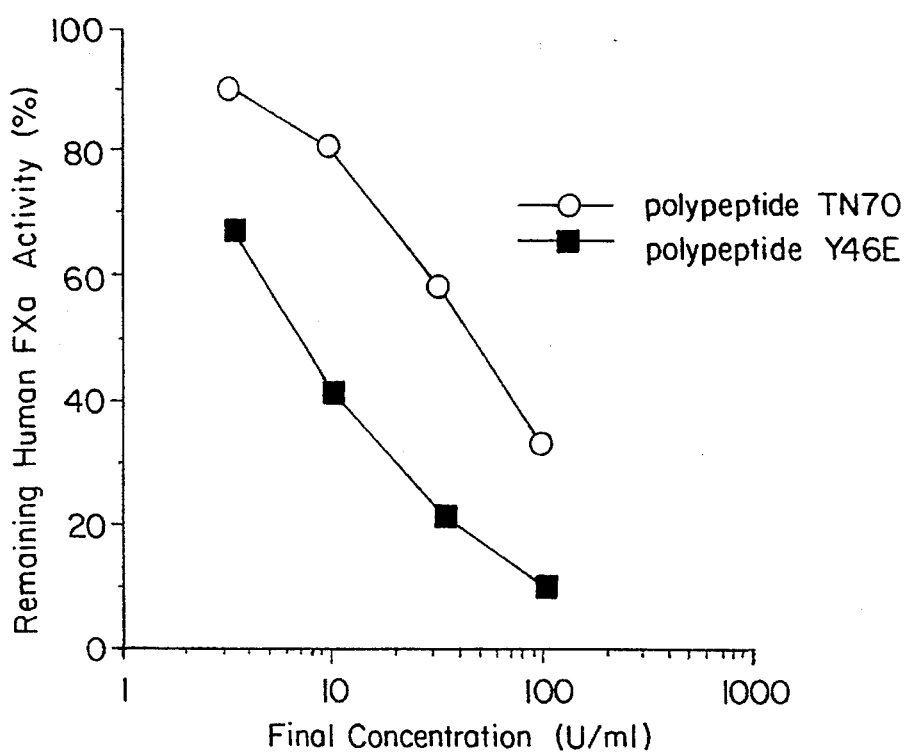
FIG. 45 is a graph showing FXa-inhibiting activity of polypeptide Y46E of the present invention.

FIG. 45 shows the novel polypeptide Y46E of the present invention has significantly high FXa-inhibiting activity in comparison with the polypeptide TN70 used as a control. In other words, it has an FXa-inhibiting activity which is about seven times higher than that of the polypeptide TN70.

Figure 46:
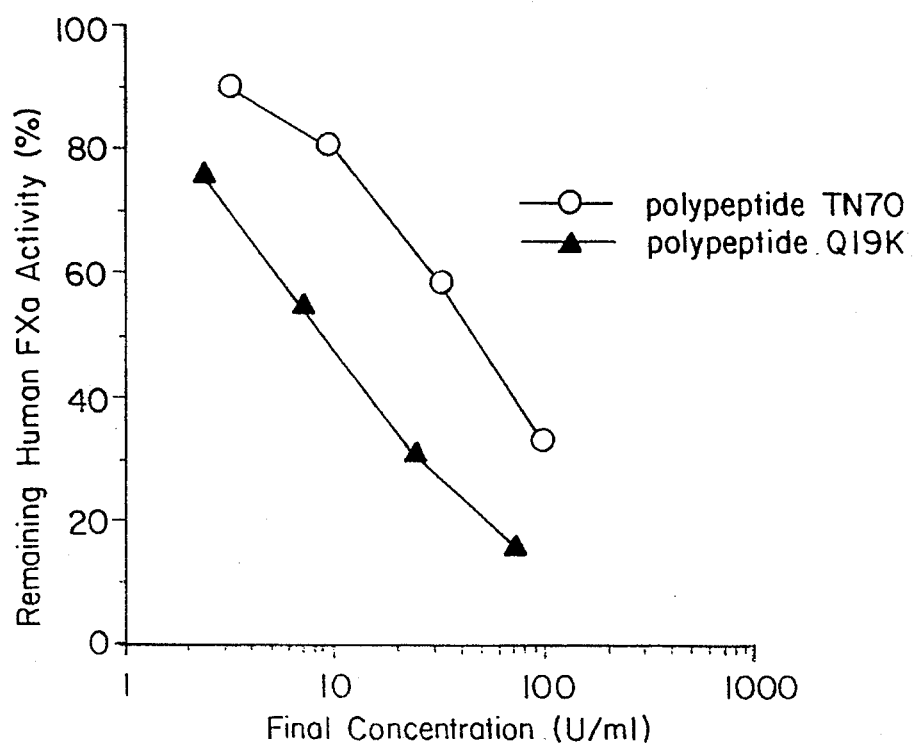
FIG. 46 is a graph showing FXa-inhibiting activity of polypeptide Q19K of the present invention.

FIG. 46 shows the novel polypeptide Q19K of the present invention has significantly high FXa-inhibiting activity in comparison with the polypeptide TN70 used as a control. In other words, it has an FXa-inhibiting activity which is about five times higher than that of the polypeptide TN70.

Figure 47:
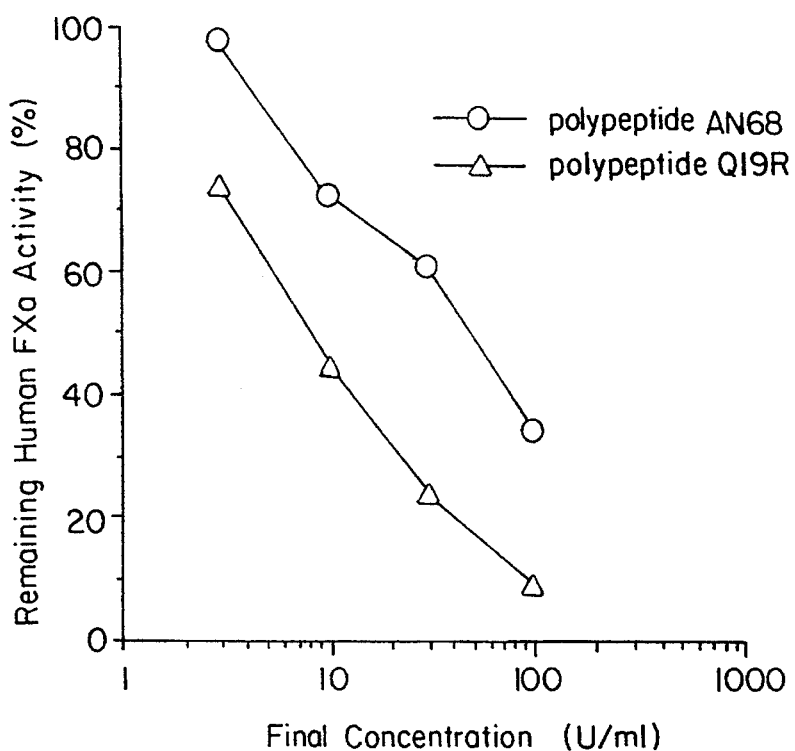
FIG. 47 is a graph showing FXa-inhibiting activity of polypeptide Q19R of the present invention.

FIG. 47 shows the novel polypeptide Q19R of the present invention has significantly high FXa-inhibiting activity in comparison with the polypeptide AN68 used as a control. In other words, it has an FXa-inhibiting activity which is about six times higher than that of the polypeptide AN68.

Figure 48:
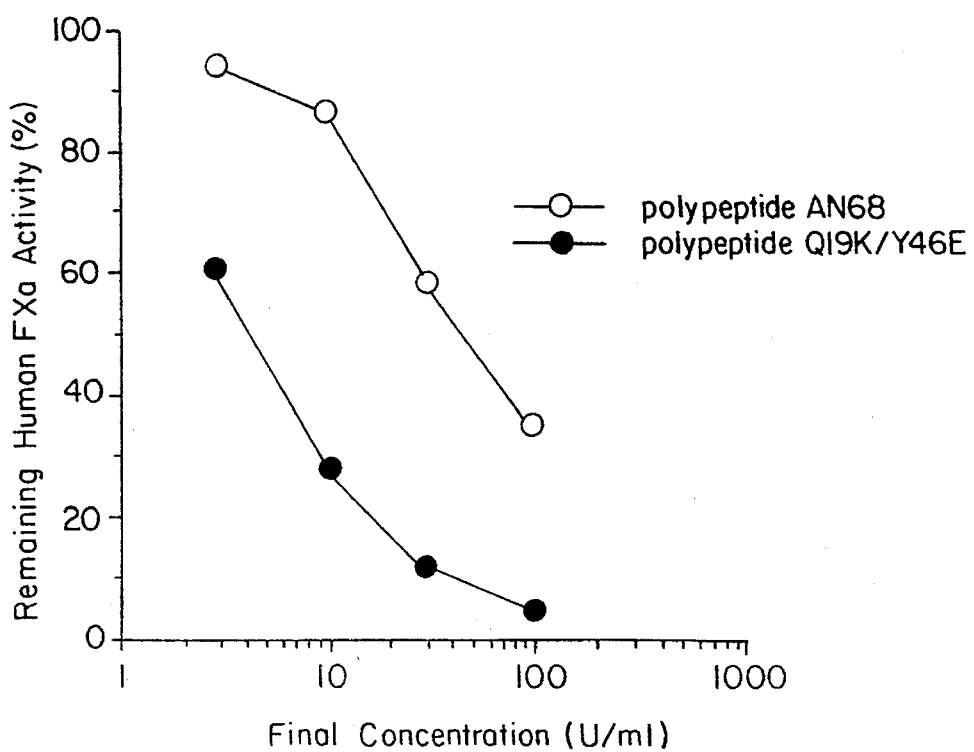
FIG. 48 is a graph showing FXa-inhibiting activity of polypeptide Q19K/Y46E of the present invention.

FIG. 48 shows the novel polypeptide Q19K/Y46E of the present invention has significantly high FXa-inhibiting activity in comparison with the polypeptide AN68 used as a control. In other words, it has an FXa-inhibiting activity which is about ten times higher than that of the polypeptide AN68.

Figure 49:
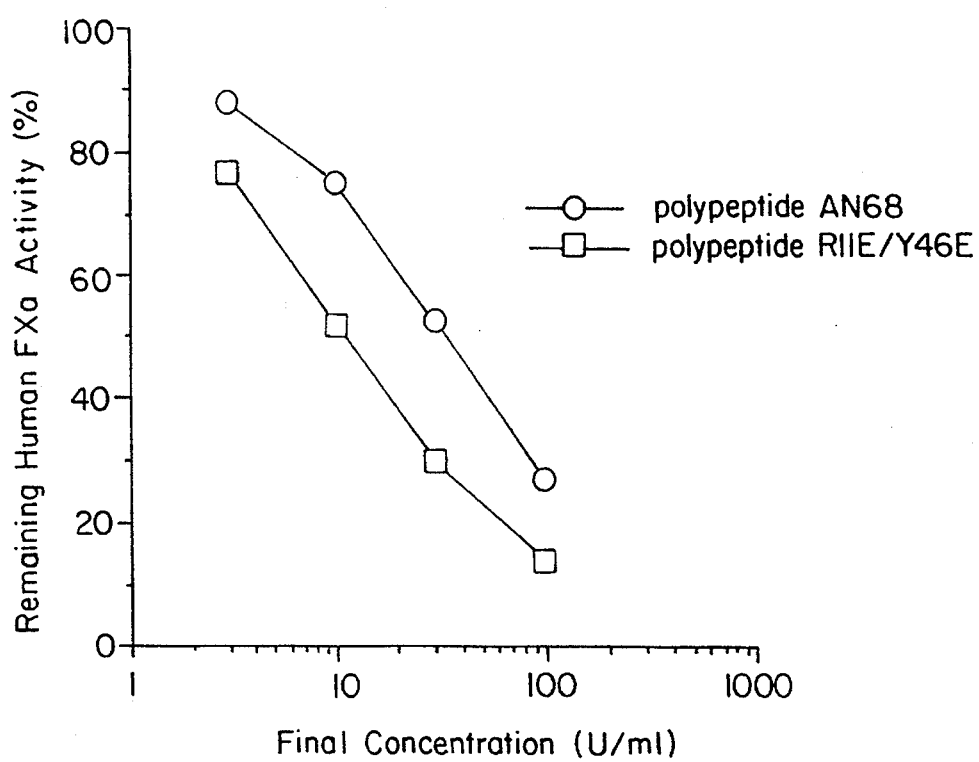
FIG. 49 is a graph showing FXa-inhibiting activity of polypeptide R11E/Y46E of the present invention.

FIG. 49 shows the novel polypeptide R11E/Y46E of the present invention has significantly high FXa-inhibiting activity in comparison with the polypeptide AN68 used as a control. In other words, it has an FXa-inhibiting activity which is about three times higher than that of the polypeptide AN68.

Figure 50:
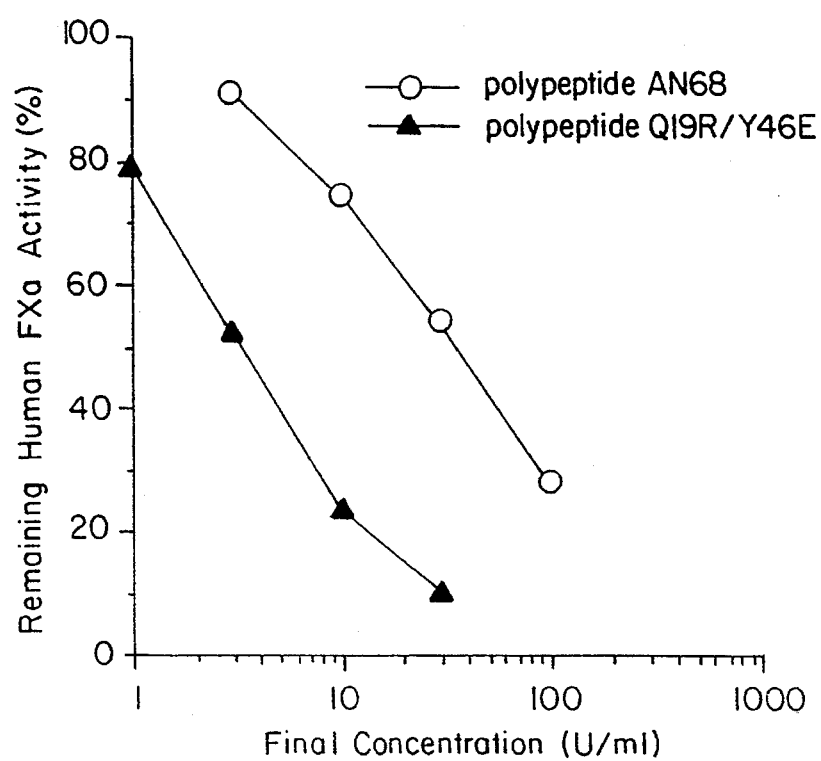
FIG. 50 is a graph showing FXa-inhibiting activity of polypeptide Q19R/Y46E of the present invention.

FIG. 50 shows the novel polypeptide Q19R/Y46E of the present invention has an FXa-inhibiting activity which is about ten times higher than that of the polypeptide AN68.

Figure 51:
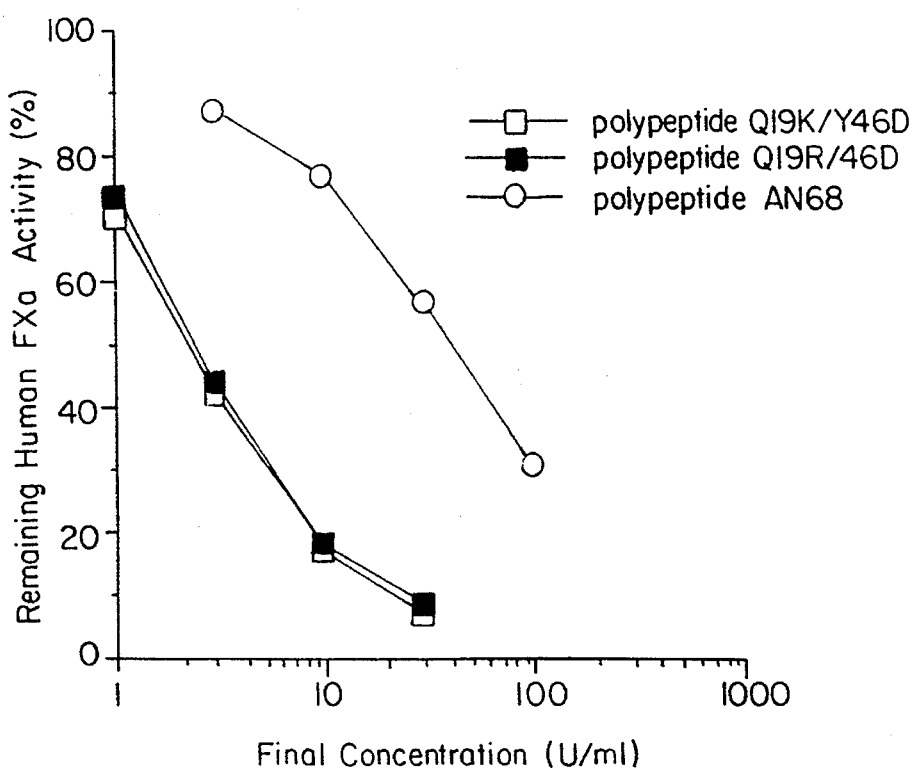
FIG. 51 is a graph showing FXa-inhibiting activity of polypeptides Q19K/Y46D and Q19R/Y46D of the present invention.

FIG. 51 shows the novel polypeptides Q19K/Y46D and Q19R/Y46D of the present invention have significantly high FXa-inhibiting activity in comparison with the polypeptide AN68 used as a control. In other words, polypeptide Q19K/Y46D has an FXa-inhibiting activity which is about twenty times higher than that of the polypeptide AN68. And polypeptide Q19R/Y46D has an FXa-inhibiting activity which is about 18 times higher than that of the polypeptide AN68.

Figure 52:
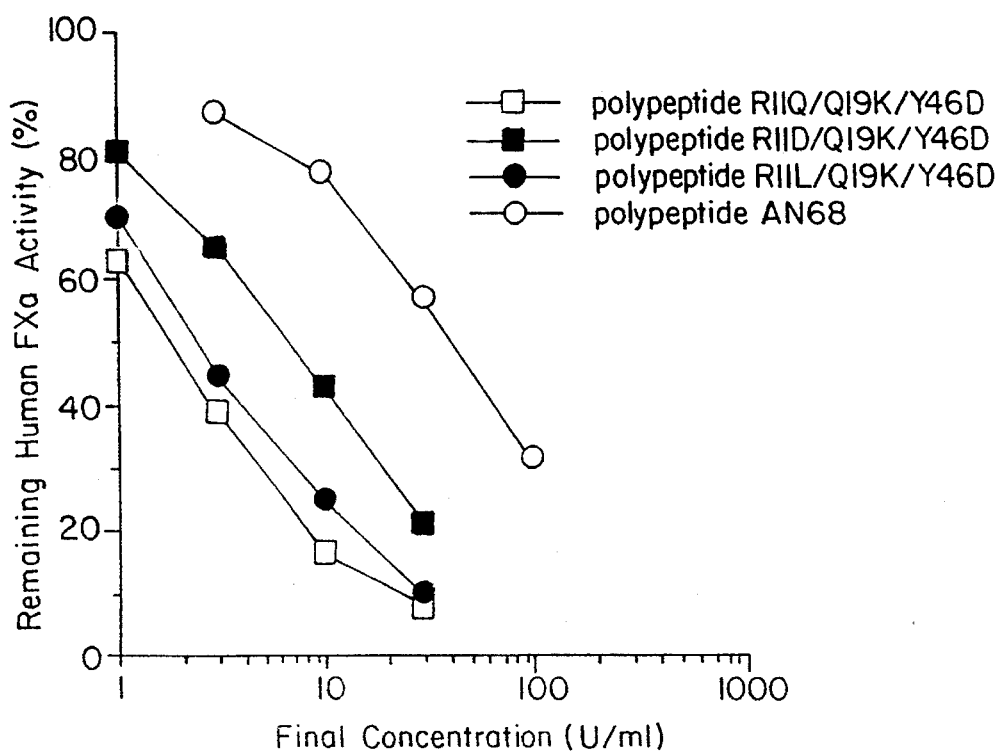
FIG. 52 is a graph showing FXa-inhibiting activity of polypeptides R11Q/Q19K/Y46D, R11D/Q19K/Y46D and R11L/Q19K/Y46D of the present invention.

FIG. 52 shows the novel polypeptides R11Q/Q19K/Y46D, R11L/Q19K/Y46D, R11D/Q19K/Y46D of the present invention have significantly high FXa-inhibiting activity in comparison with the polypeptide AN68 used as a control. In other words, polypeptide R11Q/Q19K/Y46D of the present invention has an FXa-inhibiting activity which is about twenty times higher than that of the polypeptide AN68. The polypeptide R11D/Q19K/Y46D has an FXa-inhibiting activity which is about 5 times higher than that of the polypeptide AN68. The polypeptide R11L/Q19K/Y46D has an FXa-inhibiting activity which is about 16 times higher than that of the polypeptide AN68.

Figure 53:
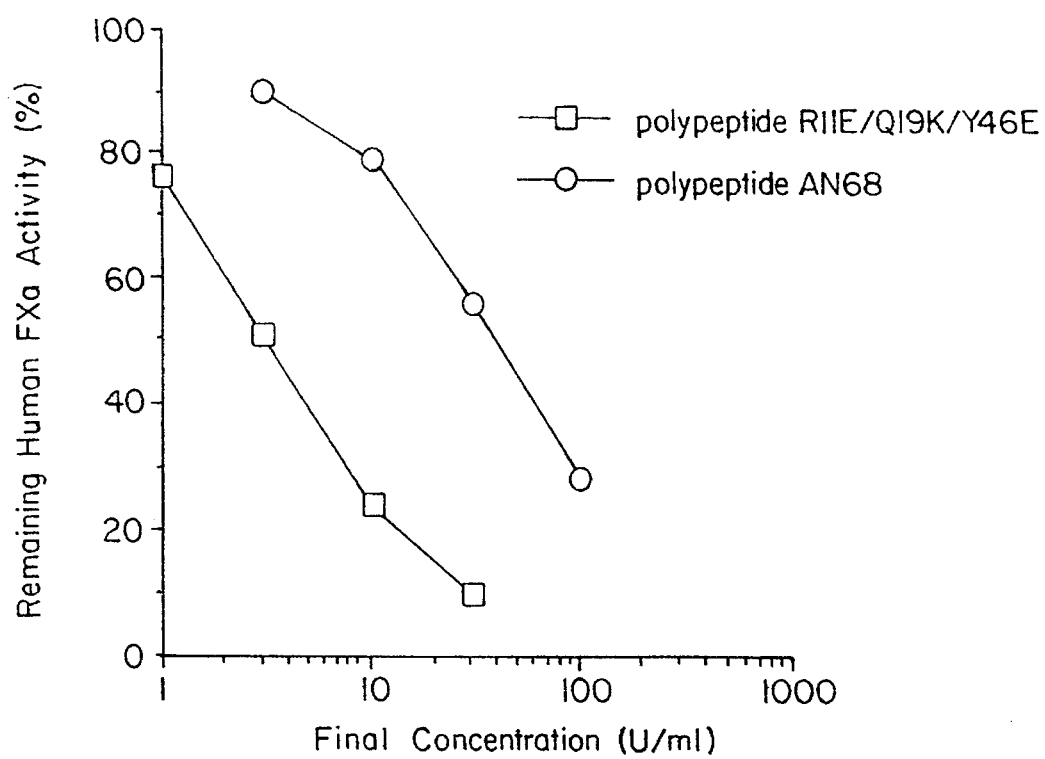
FIG. 53 is a graph showing FXa-inhibiting activity of polypeptide R11E/Q19K/Y46E of the present invention.

FIG. 53 shows the novel polypeptide R11E/Q19K/Y46E of the present invention has significantly high FXa-inhibiting activity in comparison with the polypeptide AN68 used as a control. In other words, it has an FXa-inhibiting activity which is about 13 times higher than that of the polypeptide AN68.

(4) Human elastase-inhibiting activity

The purified polypeptide of the present invention was dissolved in 100 µl of distilled water. Concentration of this solution was determined based on its bovine trypsin-inhibiting activity using the UTI as a standard. The solution was then diluted to various concentration levels with 0.1% BSA/27 mM CACl$_2$/133 mM Tris-HCl buffer (pH 7.5) for use in the activity measurement. The aforementioned AN68 was also diluted in the same manner for use as a control. Human elastase-inhibiting activities in the test samples and the positive control were measured in accordance with the method of Ogawa et al. (Ogawa,M. et al., *Res. Commun. Chem. Pathol. Pharmacol.*, vol. 55, pp. 271–274, 1987) using a synthetic compound STANA (Peptide Institute Inc.) as a substrate.

Human neutrophil elastase (CALBIOCHEM) was dissolved in 27 mM CACl$_2$/133 mM Tris-HCl buffer (pH 7.5) to a concentration of 6U/ml and the solution was further diluted with 0.1% BSA/27 mM CACl$_2$/133 mM Tris-HCl buffer (pH 7.5) to prepare 0.24U/ml of elastase solution. 100 mM STANA solution was prepared by dissolving it in N-methyl-2-pyrrolidone and the solution was further diluted with 0.1% BSA/27 mM CaCl$_2$/133 mM Tris-HCl buffer (pH 7.5) to prepare 20 mM STANA solution.

Next, 50 μl of the test sample or positive control was mixed with 50 μl of the elastase solution and 50 μl of 0.1% BSA/27 mM CACl$_2$/133 mM Tris-HCl buffer (pH 7.5). After incubation at 37° C. for 10 minutes, 50 μl of the STANA solution was added to the mixture to start the reaction. The reaction was carried out at 37° C. for 20 minutes and then stopped by adding 50 μl of 50% acetic acid solution to the reaction mixture. Thereafter, absorbance at a wave length of 405 nm was measured using a spectrophotometer.

In this instance, in order to eliminate absorbance of various solutions in the reaction product, a blank solution was prepared by mixing 50 μl of the elastase solution with 50μl of 50% acetic acid and then with 50 μl of each test sample or the positive control, 50 μl of 0.1% BSA/27 mM CACl$_2$/133 mM Tris-HCl buffer (pH 7.5) and with 50 μl of the STANA solution.

Figure 54:
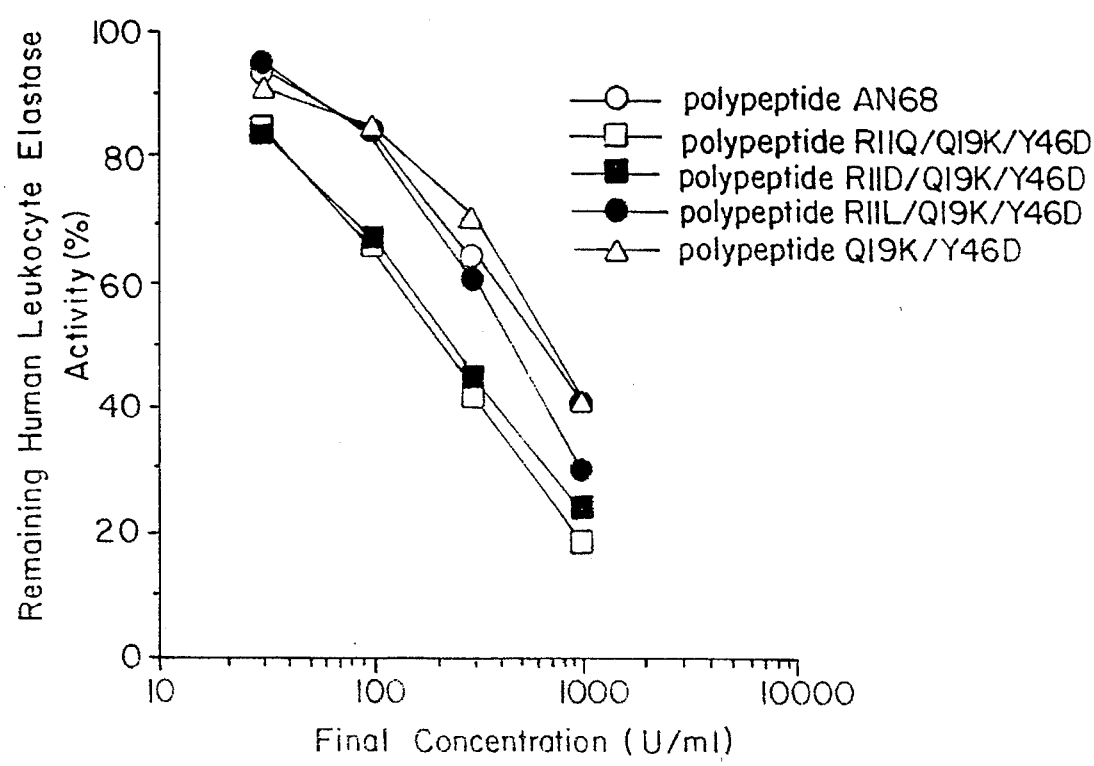
FIG. 54 is a graph showing elastase-inhibiting activity of polypeptide R11Q/Q19K/Y46D, R11D/Q19K/Y46D and R11L/Q19K/Y46D of the present invention.
Figure 55:
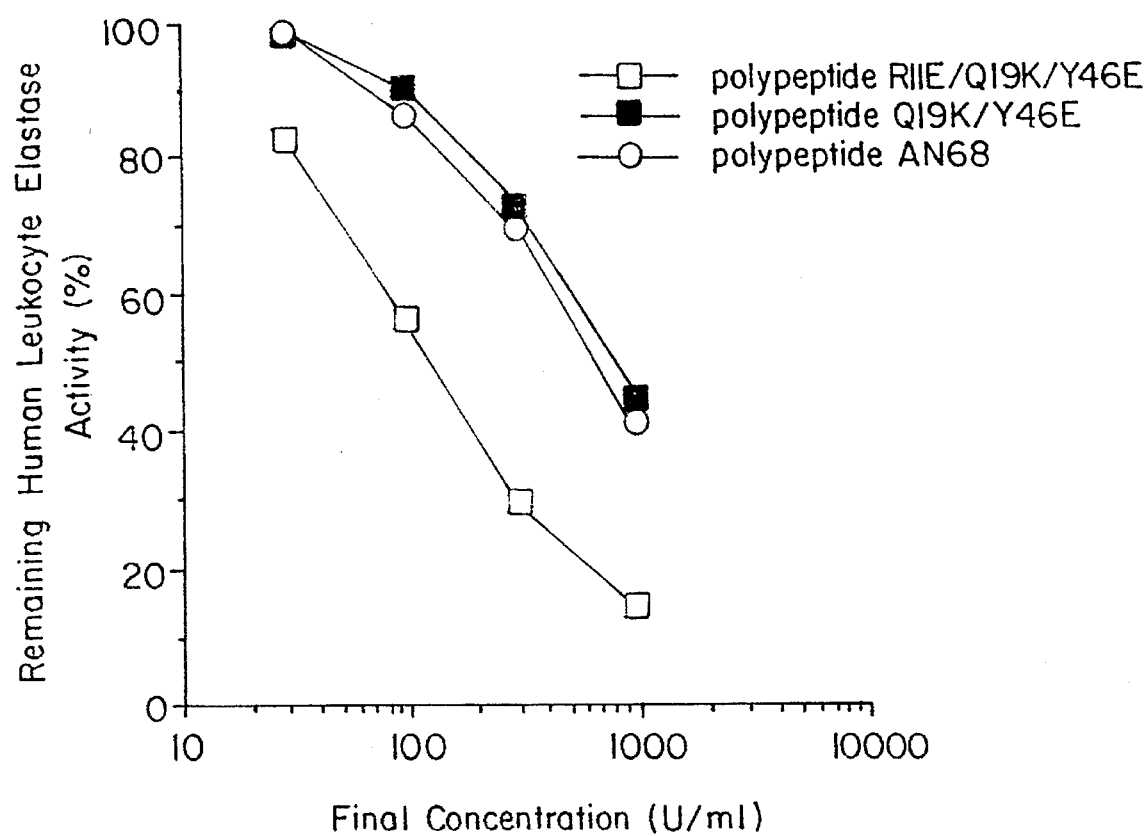
FIG. 55 is a graph showing elastase-inhibiting activity of polypeptide R11E/Q19K/Y46E of the present invention.

The results are shown in FIG. 54 and 55. In these figures, polypeptide concentration in the reaction solution was expressed as its bovine trypsin-inhibiting activity. Also, remaining human elastase activity was expressed by percentage based on the absorbance of a control reaction mixture in which 50 μl of the 0.1% BSA/27 mM CaCl$_2$/133mM Tris-HCl buffer (pH 7.5) was used instead of the test sample or the control.

FIG. 54 shows the novel polypeptides R11Q/Q19K/Y4D, R11D/Q19K/Y46D and R11L/Q19K/Y46D of the present invention have significantly high elastase-inhibiting activity in comparison with the polypeptide AN68 used as a control and the polypeptide Q19K/Y46D which was obtained Example 10 (6). In other words, the polypeptide R11Q/Q19K/Y46D has an Elastase-inhibiting activity which is about 3 times higher than that of the polypeptide AN68 and the polypeptide Q19K/Y46D. The polypeptide R11D/Q19K/Y46D has an Elastase-inhibiting activity which is about 3 times higher than that of the polypeptide AN68 and the polypeptide Q19K/Y46D. And the polypeptide R11L/Q19K/Y46D has an Elastase-inhibiting activity which is about 2 times higher than that of the polypeptide AN68 and the polypeptide Q19K/Y46D.

FIG. 55 shows the novel polypeptide R11E/Q19K/Y46E of the present invention has significantly high Elastase-inhibiting activity in comparison with the polypeptide AN68 used as a control and the polypeptide Q19K/Y46E which was purified from the cultured medium of E. coli JE5505 (pM721) transformed by plasmid pM721 obtained Example 15 (1). In other words, it has an Elastase-inhibiting activity which is about 5 times higher than that of the polypeptide AN68 and 6 times higher than that of the polypeptide Q19K/Y46E.

Example 18

Safety

Safety of the novel polypeptide of the present invention was confirmed by the following procedures (1) and (2).

(1) Polypeptide Y46E, Q19K, Q19R, Q19K/Y46E, R11E/Y46E, Y46E-AN, Q19K-AN and Q19R/Y46E were prepared from the cultured medium of transformants in accordance with the procedure in Example 2 (4).

Each of the thus prepared ten purified polypeptide samples was dissolved in physiological saline and the resulting solution was applied to PIROZALTO UNIT (molecular weight cutoff of 20,000, Saltorius) in order to remove lipopolysaccharide (to be referred to as "LPS" hereinafter).

Wistar Rats were prepared for one week in advance and then divided into administration groups and control groups, each test group including 10 males or females. Each of the polypeptide solutions prepared above was administered to rats of each administration group by intravenous injection with a dose of 100 mg/kg/day, and appearance of symptoms and changes in their body weights were observed for one week. In this instance, physiological saline was administered to the control group.

No, significant side effect was found in any of the polypeptide-administered groups, and survival rates and body weight changes in the administration groups were the same as those in the control groups.

(2) Polypeptide Q19K/Y46D, Q19R/Y46D, R11Q/Q19K/Y46D, R11D/Q19K/Y46D, R11L/Q19K/Y46D, R11E/Q19K/Y46E, R11N/Q19K/Y46D, R11S/Q19K/Y46D and R11A/Q19K/Y46D were prepared by purification from the cultured medium of transformants in accordance with the procedure in Example 10 (6).

Each of purified polypeptide was dissolved in physiological saline and applied to OMEGACEL (molecular weight cutoff of 100,000, Filtoron) in order to remove LPS.

Wistar Rats were prepared for one week in advance and then divided into administration groups and control groups, each group including A10 males or females. Each of the polypeptide solutions prepared above was administered to rats of each administration group by intravenous injection with a dose of 10 mg/kg/day. Physiological saline was administered to rats of each control group. An appearance of symptoms and changes in their body weights were observed for a week. No significant side effect was found in any of the polypeptide-administered groups, and survival rates and body weight changes in the administration groups were the same as those in the control groups.

Example 19 pharmaceutical preparations

Polypeptides Y46E, Q19K, Q19R, Q19K/Y46E, R11E/Y46E, Y46E-AN, Q19K-AN and Q19R/Y46E were prepared from the cultured medium of transformants in accordance with the procedure in Example 2 (4).

Each of the thus prepared ten purified polypeptide samples was dissolved in physiological saline and the resulting solution was applied to a PIROZALTO unit in order to remove LPS.

Polypeptides Q19K/Y46D, Q19R/Y46D, R11Q/Q19K/Y46D, R11D/Q19K/Y46D, R11E/Q19K/Y46E, R11N/Q19K/Y46D, R11S/Q19K/Y46D and R11A/Q19K/Y46D were prepared by purification from the cultured medium of transformants in accordance with the procedure in Example 2 (4) or Example 10 (6).

Each of purified polypeptides were dissolved in distilled water and then applied to an aforementioned membrane, OMEGACEL in order to remove LPS. Thereafter, each of the thus prepared polypeptide solutions was dried under a reduced pressure and then made into pharmaceutical preparations in accordance with the following procedures (1) and (2).

(1) Each of the thus prepared polypeptide samples was dissolved, to a final concentration of 2 mg/ml, in 1/15M phosphate buffer (pH 7.4) containing 0.1% w/v) of pyrogen-free gelatin which has been prepared using distilled water for injection use. To the resulting solution of each polypeptide sample were added sodium chloride to a final concentration of 75 mM and mannitol to a final concentration of 2% (w/v). The thus prepared sample solution was sterilized by filtration through an aseptic membrane filter having a pore size of 0.22 μm (Disposable Sterile Filter System, Corning) and dispensed in 5 ml aliquots into glass vessels.

(2) Each of the thus prepared polypeptide samples was dissolved, to a final concentration of 2 mg/ml, in 0.01M phosphate buffer (pH 7.4) containing 0.14M sodium chloride which has been prepared using distilled water for injection use. To the resulting solution of each polypeptide sample was added human serum albumin to a final concentration of 1% (w/v). The thus prepared sample solution was sterilized by filtration through the aforementioned aseptic membrane filter having a pore size of 0.22 μm (Disposable Sterile Filter System) and dispensed in 5 ml aliquots into glass vessels. Thereafter, the thus dispensed samples were freeze-dried and sealed.

Thus, it is apparent that there have been provided, in accordance with the present invention, novel polypeptides and processes for the production thereof. The present invention also provides DNA fragments which encode the novel polypeptides, vectors containing the DNA fragments and transformants transformed with the DNA fragments or the vectors. This invention also provides drug compositions which contain the novel polypeptides as the active ingredient, as well as enzyme inhibition processes in which the novel polypeptides are used.

The polypeptide of this invention can be used not only as an active ingredient of a drug composition but also for the purpose of preventing blood coagulation on the surface of medical instruments such as artificial blood vessels, artificial organs, catheters and the like, by binding or adsorbing the polypeptide to the surface of instruments making use of a cross-linking agent and the like. In consequence, this invention opens a new way for preventing and treating various diseases including protease-related diseases such as infestation, multiple-organ failure, shock, pancreatitis, disseminated intravascular coagulation syndrome, ischemic heart disease, nephritis, hepatic cirrhosis, re-obstruction at the time of blood circulation reconstructive operation, edema caused by increased vascular permeability, adult respiratory distress syndrome, rheumatoid arthritis, arthritis and allergic diseases.

Although some preferred embodiments have been described, many modifications and variations may be made thereto in the light of the above teachings. It is therefore to be understood that within the scope of the appended claims, the invention may be practiced otherwise than as specifically described.

What is claimed is:

1. An isolated DNA molecule which comprises a nucleotide sequence encoding a polypeptide consisting of a polypeptide having an amino acid sequence as recited in SEQ. I.D. NO. 67, wherein the amino acid sequence as recited in SEQ. I.D. NO. 67 is substituted by at least one substitution selected from the substitutions (i) to (iii);

(i) substitution of Arg at residue 7, counting from the amino-terminus by an amino acid selected from the group consisting of Ala, Asp, Asn, Gln, Leu, Glu and Ser, (ii) substitution of Gln at residue 15, counting from the amino-terminus by an amino acid selected from the group consisting of Arg and Lys, and (iii) substitution of Tyr at residue 42, counting from the amino-terminus by an amino acid selected from the group consisting of Asp, and Glu;

wherein said polypeptide optionally has an amino-terminal peptide having an amino acid sequence selected from the group consisting of;

Asp-Asp-Ala-Ala-, Thr-Val-Ala-Ala-, Val-Ala-Ala-, Ala-Ala-, and Ala-; and wherein said polypeptide optionally has a carboxy-terminal peptide having an amino acid sequence selected from the group consisting of;

Gly-Val-Pro-Gly-Asp-Gly-Asp-Glu-Glu-Leu-Leu-Arg-Phe-Ser-Asn,

Gly-Val-Pro-Gly-Asp-Gly-Asp-Glu-Glu-Leu-Leu-Arg-Phe-Ser-,

Gly-Val-Pro-Gly-Asp-Gly-Asp-Glu-Glu-Leu-Leu-Arg-Phe-,

Gly-Val-Pro-Gly-Asp-Gly-Asp-Glu-Glu-Leu-Leu-Arg-,

Gly-Val-Pro-Gly-Asp-Gly-Asp-Glu-Glu-Leu-Leu-,

Gly-Val-Pro-Gly-Asp-Gly-Asp-Glu-Glu-,

Gly-Val-Pro-Gly-Asp-Gly-Asp-Glu-Glu-,

Gly-Val-Pro-Gly-Asp-Gly-Asp-Glu-,

Gly-Val-Pro-Gly-Asp-Gly-Asp-,

Gly-Val-Pro-Gly-Asp-Gly-, Gly-Val-Pro-Gly-Asp-,

Gly-Val-Pro-Gly-, Gly-Val-Pro-, Gly-Val-, and Gly-.

2. The DNA molecule according to claim 1, wherein said molecule comprises a nucleotide sequence resulting from substitution of a nucleotide for at least one nucleotide in SEQ. I.D. NO. 66.

3. The DNA molecule according to claim 2 wherein said nucleotide substitution in the nucleotide sequence of SEQ. I.D. NO. 66 is at least one substitution selected from the following substitutions (i) to (iii);

(i) substitution of at least one nucleotide among the CAG residues 43 to 45, counting from the 5' end, (ii) substitution of at least one nucleotide among the TAC residues 124 to 126, counting from the 5' end, and (iii) substitution of at least one nucleotide among the CGG residues 19 to 21, counting from the 5' end.

4. The DNA fragment according to claim 2 wherein said nucleotide substitution in the nucleotide sequence of SEQ. I.D. NO. 66 is at least one substitution selected from the following substitutions (1) to (11);

(1) substitution of the 43 to 45 position nucleotide sequence CAG counting from the 5' end by another nucleotide sequence coding for Lys, (2) substitution of the 43 to 45 position nucleotide sequence CAG counting from the 5' end by another nucleotide sequence coding for Arg, (3) substitution of the 124 to 126 position nucleotide sequence TAC counting from the 5' end by another nucleotide sequence coding for Glu, (4) substitution of the 124 to 126 position nucleotide sequence TAC counting from the 5' end by another nucleotide sequence coding for Asp, (5) substitution of the 19 to 21 position nucleotide sequence CGG counting from the 5' end by another nucleotide sequence coding for Glu, (6) substitution of the 19 to 21 position nucleotide sequence CGG counting from the 5' end by another nucleotide sequence coding for Gln, (7) substitution of the 19 to 21 position nucleotide sequence CGG counting from the 5' end by another nucleotide sequence coding for Asp, (8) substitution of the 19 to 21 position nucleotide sequence CGG counting from the 5' end by another nucleotide sequence coding for Leu, (9) substitution of the 19 to 21 position nucleotide sequence CGG counting from the 5' end by another nucleotide sequence coding for Asn,

(10) substitution of the 19 to 21 position nucleotide sequence CGG counting from the 5' end by another nucleotide sequence coding for Ser, and

(11) substitution of the 19 to 21 position sequence CGG counting from the 5' end by another nucleotide sequence coding for Ala.

5. The DNA molecule according to claim 2 wherein said nucleotide substitution in the nucleotide sequence of SEQ. I.D. NO. 66 is at least one substitution selected from the following substitutions (1) to (11);

(1) substitution of AAG for the 43 to 45 position nucleotide sequence CAG counting from the 5' end, (2) substitution of CGT for the 43 to 45 position nucleotide sequence CAG counting from the 5' end, (3) substitution of GAA for the 124 to 126 position nucleotide sequence TAC counting from the 5' end, (4) substitution of GAC for the 124 to 126 position nucleotide sequence TAC counting from the 5' end, (5) substitution of GAA for the 19 to 21 position nucleotide sequence CGG counting from the 5' end, (6) substitution of CAG for the 19 to 21 position nucleotide sequence CGG counting from the 5' end, (7) substitution of GAT for the 19 to 21 position nucleotide sequence CGG counting from the 5' end, (8) substitution of CTG for the 19 to 21 nucleotide sequence CGG counting from the 5' end, (9) substitution of AAC for the 19 to 21 position nucleotide sequence CGG counting from the 5' end,

(10) substitution of AGC for the 19 to 21 position nucleotide sequence CGG counting from the 5' end, and

(11) substitution of GCG for the 19 to 21 position nucleotide sequence CGG counting from the 5' end.

6. An isolated DNA molecule comprising a first DNA molecule according to claim 2 and a second DNA molecule consisting of a nucleotide sequence selected from the following nucleotide sequences (1) to (5)

(1) GAC GAC GCC GCC, (2) ACC GTC GCC GCC, (3) GTC GCC GCC, (4) GCC GCC, and (5) GCC, wherein the 3' end of said second DNA molecule is attached to the 5' end of said first DNA molecule.

7. An isolated DNA molecule comprising a first DNA molecule according to claim 2 and a second DNA molecule consisting of a nucleotide sequence selected from the following nucleotide sequences (1) to (15)
(1) GGT GTC CCT GGT GAT GGT GAT GAG GAG CTG CTG CGC TTC TCC AAC,
(2) GGT GTC CCT GGT GAT GGT GAT GAG GAG CTG CTG CGC TTC TCC,
(3) GGT GTC CCT GGT GAT GGT GAT GAG GAG CTG CTG CGC TTC,
(4) GGT GTC CCT GGT GAT GGT GAT GAG GAG CTG CTG CGC,
(5) GGT GTC CCT GGT GAT GGT GAT GAG GAG CTG CTG,
(6) GGT GTC CCT GGT GAT GGT GAT GAG GAG CTG,
(7) GGT GTC CCT GGT GAT GGT GAT GAG GAG,
(8) GGT GTC CCT GGT GAT GGT GAT GAG,
(9) GGT GTC CCT GGT GAT GGT GAT,
(10) GGT GTC CCT GGT GAT GGT,,
(11) GGT GTC CCT GGT GAT,
(12) GGT GTC CCT GGT,
(13) GGT GTC CCT,
(14) GGT GTC, and
(15) GGT,
wherein the 3' end of said first DNA molecule is attached to the 5' end of said second DNA molecule.

8. An isolated DNA molecule comprising a first DNA molecule according to claim 2, a second DNA molecule consisting of a nucleotide sequence selected from the following nucleotide sequences (1) to (5)
(1) GAC GAC GCC GCC,
(2) ACC GTC GCC GCC,
(3) GTC GCC GCC,
(4) GCC GCC, and
(5) GCC,
and a third DNA molecule consisting of a nucleotide sequence selected the following nucleotide sequences (1) to (15):
(1) GGT GTC CCT GGT GAT GGT GAT GAG GAG CTG CTG CGC TTC TCC AAC,
(2) GGT GTC CCT GGT GAT GGT GAT GAG GAG CTG CTG CGC TTC TCC,
(3) GGT GTC CCT GGT GAT GGT GAT GAG GAG CTG CTG CGC TTC,
(4) GGT GTC CCT GGT GAT GGT GAT GAG GAG CTG CTG CGC,
(5) GGT GTC CCT GGT GAT GGT GAT GAG GAG CTG CTG,
(6) GGT GTC CCT GGT GAT GGT GAT GAG GAG CTG,
(7) GGT GTC CCT GGT GAT GGT GAT GAG GAG,
(8) GGT GTC CCT GGT GAT GGT GAT GAG,
(9) GGT GTC CCT GGT GAT GGT GAT,
(10) GGT GTC CCT GGT GAT GGT,,
(11) GGT GTC CCT GGT GAT,
(12) GGT GTC CCT GGT,
(13) GGT GTC CCT,
(14) GGT GTC, and
(15) GGT,
wherein the 3' end of said second DNA molecule is attached to the 5' end of said first DNA molecule and wherein the 3' end of said first DNA molecule is attached to the 5' end of said third DNA molecule.

9. A vector which contains the DNA molecule of any one of the claims 1 to 7 and 8.

10. A cell transformed with the DNA molecule of any one of the claims 1 to 7 and 8.

11. A cell transformed with the vector of claim 9.

12. A process for producing polypeptide consisting of a polypeptide having an amino acid sequence as recited in SEQ. I.D. NO. 67, wherein the amino acid sequence as recited in SEQ. I.D. NO. 67 is substituted by at least one substitution selected from the substitutions (i) to (iii);
(i) substitution of Arg at residue 7, counting from the amino-terminus by an amino acid selected from the group consisting of Ala, Asp, Asn, Gln, Leu, Glu and Ser,
(ii) substitution of Gln at residue 15, counting from the amino-terminus by an amino acid selected from the group consisting of Arg and Lys, and
(iii) substitution of Tyr at residue 42, counting from the amino-terminus by an amino acid selected from the group consisting of Asp, and Glu;
wherein said polypeptide optionally has an amino-terminal peptide having an amino acid sequence selected from the group consisting of;
Asp-Asp-Ala-Ala-, Thr-Val-Ala-Ala-, Val-Ala-Ala-, Ala-Ala-, and Ala-; and
wherein said polypeptide optionally has a carboxy-terminal peptide having an amino acid sequence selected from the group consisting of;
Gly-Val-Pro-Gly-Asp-Gly-Asp-Glu-Glu-Leu-Leu-Arg-Phe-Ser-Asn,
Gly-Val-Pro-Gly-Asp-Gly-Asp-Glu-Glu-Leu-Leu-Arg-Phe-Ser-,
Gly-Val-Pro-Gly-Asp-Gly-Asp-Glu-Glu-Leu-Leu-Arg-Phe-,
Gly-Val-Pro-Gly-Asp-Gly-Asp-Glu-Glu-Leu-Leu-Arg-,
Gly-Val-Pro-Gly-Asp-Gly-Asp-Glu-Glu-Leu-Leu-,
Gly-Val-Pro-Gly-Asp-Gly-Asp-Glu-Glu-Leu-,
Gly-Val-Pro-Gly-Asp-Gly-Asp-Glu-Glu-,
Gly-Val-Pro-Gly-Asp-Gly-Asp-Glu-,
Gly-Val-Pro-Gly-Asp-Gly-Asp-,
Gly-Val-Pro-Gly-Asp-Gly-,Gly-Val-Pro-Gly-Asp-,
Gly-Val-Pro-Gly-, Gly-Val-Pro-, Gly-Val, and Gly-,
which comprises the steps of:
a) preparing a DNA fragment containing a nucleotide sequence which encodes said polypeptide,
b) preparing a transformant by transforming a host cell with the DNA fragment obtained in the above step a), and
c) culturing the transformant obtained in the above step b) to allow the transformant to produce said polypeptide and subsequently recovering said polypeptide from the culture medium.

13. A process for producing a polypeptide consisting of a polypeptide having an amino acid sequence as recited in SEQ. I.D. NO. 67, wherein the amino acid sequence as recited in SEQ. I.D. NO. 67 is substituted by at least one substitution selected from the substitutions (i) to (iii);
(i) substitution of Arg at residue 7, counting from the amino-terminus by an amino acid selected from the group consisting of Ala, Asp, Asn, Gln, Leu, Glu and Ser,
(ii) substitution of Gln at residue 15, counting from the amino-terminus by an amino acid selected from the group consisting of Arg and Lys, and
(iii) substitution of Tyr at residue 42, counting from the amino-terminus by an amino acid selected from the group consisting of Asp, and Glu
wherein said polypeptide optionally has an amino-terminal peptide having an amino acid sequence selected from the group consisting of;

Asp-Asp-Ala-Ala-, Thr-Val-Ala-Ala-, Val-Ala-Ala-, Ala-Ala-, and Ala-; and wherein said polypeptide optionally has a carboxy-terminal peptide having an amino acid sequence selected from the group consisting of;

Gly-Val-Pro-Gly-Asp-Gly-Asp-Glu-Glu-Leu-Leu-Arg-Phe-Ser-Asn,

Gly-Val-Pro-Gly-Asp-Gly-Asp-Glu-Glu-Leu-Leu-Arg-Phe-Ser-,

Gly-Val-Pro-Gly-Asp-Gly-Asp-Glu-Glu-Leu-Leu-Arg-Phe-,

Gly-Val-Pro-Gly-Asp-Gly-Asp-Glu-Glu-Leu-Leu-Arg-,

Gly-Val-Pro-Gly-Asp-Gly-Asp-Glu-Glu-Leu-Leu-,

Gly-Val-Pro-Gly-Asp-Gly-Asp-Glu-Glu-Leu-,

Gly-Val-Pro-Gly-Asp-Gly-Asp-Glu-Glu-,

Gly-Val-Pro-Gly-Asp-Gly-Asp-Glu-,

Gly-Val-Pro-Gly-Asp-Gly-Asp-,

Gly-Val-Pro-Gly-Asp-Gly-, Gly-Val-Pro-Gly-Asp-,

Gly-Val-Pro-Gly-, Gly-Val-Pro-, Gly-Val, and Gly-, which comprises the steps of:

a) preparing a DNA fragment containing a nucleotide sequence which encodes said polypeptide, b) preparing a vector which contains the DNA fragment obtained in the above step a), c) preparing a transformant by transforming a host cell with the vector obtained in the above step b), and d) culturing the transformant obtained in the above step c) to allow the transformant to produce said polypeptide and subsequently recovering said polypeptide from the culture medium.

* * * * *

SEQUENCE LISTING ( 1 ) GENERAL INFORMATION:

( i i i ) NUMBER OF SEQUENCES: 76

( 2 ) INFORMATION FOR SEQ ID NO:1:

( i ) SEQUENCE CHARACTERISTICS:
        ( A ) LENGTH: 313 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Eschericia coli
        ( B ) STRAIN: JE5505 (pM575B)

( i x ) FEATURE:
        ( A ) NAME/KEY: sig_peptide
        ( B ) LOCATION: 27..89
        ( D ) OTHER INFORMATION: /standard_name= "pho A signal peptide"

( i x ) FEATURE:
        ( A ) NAME/KEY: mat_peptide
        ( B ) LOCATION: 90..299
        ( D ) OTHER INFORMATION: /product="polypeptide Y46E"

( i x ) FEATURE:
        ( A ) NAME/KEY: CDS
        ( B ) LOCATION: 27..299

( i x ) FEATURE:
        ( A ) NAME/KEY: -
        ( B ) LOCATION: 1..313
        ( D ) OTHER INFORMATION: /label=sequence
        / note= "as in Figure 9"

( x i ) SEQUENCE DESCRIPTION: SEQ ID NO:1:

```
AAGCTTAAAA  AAGGGTATAA  AATAAA ATG AAA CAA AGT ACT ATT GCA CTG GCA        53
                              Met Lys Gln Ser Thr Ile Ala Leu Ala
                              -21 -20                          -15
```

| | | | | | | | | | | | | | | | | |
|---|---|---|---|---|---|---|---|---|---|---|---|---|---|---|---|---|
| CTC | TTA | CCG | TTA | CTG | TTT | ACC | CCT | GTG | ACA | AAG | GCC | ACC | GTC | GCC | GCC | 101 |
| Leu | Leu | Pro | Leu | Leu | Phe | Thr | Pro | Val | Thr | Lys | Ala | Thr | Val | Ala | Ala | |
| | | -10 | | | | | -5 | | | | | | 1 | | | |
| TGC | AAT | CTC | CCC | ATA | GTC | CGG | GGC | CCC | TGC | CGA | GCC | TTC | ATC | CAG | CTC | 149 |
| Cys | Asn | Leu | Pro | Ile | Val | Arg | Gly | Pro | Cys | Arg | Ala | Phe | Ile | Gln | Leu | |
| 5 | | | | | 10 | | | | | 15 | | | | | 20 | |
| TGG | GCA | TTT | GAT | GCT | GTC | AAG | GGG | AAG | TGC | GTC | CTC | TTC | CCC | TAC | GGG | 197 |
| Trp | Ala | Phe | Asp | Ala | Val | Lys | Gly | Lys | Cys | Val | Leu | Phe | Pro | Tyr | Gly | |
| | | | | 25 | | | | | 30 | | | | | 35 | | |
| GGC | TGC | CAG | GGC | AAC | GGG | AAC | AAG | TTC | GAA | TCA | GAG | AAG | GAG | TGC | AGA | 245 |
| Gly | Cys | Gln | Gly | Asn | Gly | Asn | Lys | Phe | Glu | Ser | Glu | Lys | Glu | Cys | Arg | |
| | | | 40 | | | | | 45 | | | | | 50 | | | |
| GAG | TAC | TGC | GGT | GTC | CCT | GGT | GAT | GGT | GAT | GAG | GAG | CTG | CTG | CGC | TTC | 293 |
| Glu | Tyr | Cys | Gly | Val | Pro | Gly | Asp | Gly | Asp | Glu | Glu | Leu | Leu | Arg | Phe | |
| | | 55 | | | | | 60 | | | | | 65 | | | | |
| TCC | AAC | TGACAACTGG | ATCC | | | | | | | | | | | | | 313 |
| Ser | Asn | | | | | | | | | | | | | | | |
| | 70 | | | | | | | | | | | | | | | |

( 2 ) INFORMATION FOR SEQ ID NO:2:

( i ) SEQUENCE CHARACTERISTICS:
        ( A ) LENGTH: 91 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | |
|---|---|---|---|---|---|---|---|---|---|---|---|---|---|
| Met | Lys | Gln | Ser | Thr | Ile | Ala | Leu | Ala | Leu | Leu | Pro | Leu | Leu | Phe | Thr |
| -21 | -20 | | | | | -15 | | | | | -10 | | | | |
| Pro | Val | Thr | Lys | Ala | Thr | Val | Ala | Ala | Cys | Asn | Leu | Pro | Ile | Val | Arg |
| -5 | | | | | 1 | | | | 5 | | | | | 10 | |
| Gly | Pro | Cys | Arg | Ala | Phe | Ile | Gln | Leu | Trp | Ala | Phe | Asp | Ala | Val | Lys |
| | | | 15 | | | | | 20 | | | | | 25 | | |
| Gly | Lys | Cys | Val | Leu | Phe | Pro | Tyr | Gly | Gly | Cys | Gln | Gly | Asn | Gly | Asn |
| | | 30 | | | | | 35 | | | | | 40 | | | |
| Lys | Phe | Glu | Ser | Glu | Lys | Glu | Cys | Arg | Glu | Tyr | Cys | Gly | Val | Pro | Gly |
| | 45 | | | | 50 | | | | | | 55 | | | | |
| Asp | Gly | Asp | Glu | Glu | Leu | Leu | Arg | Phe | Ser | Asn | | | | | |
| 60 | | | | | 65 | | | | | 70 | | | | | |

( 2 ) INFORMATION FOR SEQ ID NO:3:

( i ) SEQUENCE CHARACTERISTICS:
        ( A ) LENGTH: 349 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Eschericia coli
        ( B ) STRAIN: JE5505 (pM576)

( i x ) FEATURE:
        ( A ) NAME/KEY: -
        ( B ) LOCATION: 1..349
        ( D ) OTHER INFORMATION: /label=sequence
            / note= "as in figure 16"

( i x ) FEATURE:
        ( A ) NAME/KEY: sig_peptide
        ( B ) LOCATION: 44..106

( D ) OTHER INFORMATION: /standard_name= "pho A signal peptide"

( i x ) FEATURE:
  ( A ) NAME/KEY: mat_peptide
  ( B ) LOCATION: 107..316
  ( D ) OTHER INFORMATION: /product="polypeptide Q19K"

( i x ) FEATURE:
  ( A ) NAME/KEY: CDS
  ( B ) LOCATION: 44..316

( x i ) SEQUENCE DESCRIPTION: SEQ ID NO:3:

| | | | | |
|---|---|---|---|---|
| ACGCAAGTTC ACGTAAAAAG CTTAAAAAAG GGTATAAAAT AAA ATG AAA CAA AGT<br>                                                    Met Lys Gln Ser<br>                                                    -21  -20 | | | | 55 |
| ACT ATT GCA CTG GCA CTC TTA CCG TTA CTG TTT ACC CCT GTG ACA AAG<br>Thr Ile Ala Leu Ala Leu Leu Pro Leu Leu Phe Thr Pro Val Thr Lys<br>        -15                 -10                  -5 | | | | 103 |
| GCC GAC GAC GCC GCC TGC AAT CTC CCC ATA GTC CGG GGC CCC TGC CGA<br>Ala Asp Asp Ala Ala Cys Asn Leu Pro Ile Val Arg Gly Pro Cys Arg<br>         1            5                  10                 15 | | | | 151 |
| GCC TTC ATC AAG CTC TGG GCA TTT GAT GCT GTC AAG GGG AAG TGC GTC<br>Ala Phe Ile Lys Leu Trp Ala Phe Asp Ala Val Lys Gly Lys Cys Val<br>                 20                 25                 30 | | | | 199 |
| CTC TTC CCC TAC GGG GGC TGC CAG GGC AAC GGG AAC AAG TTC TAC TCA<br>Leu Phe Pro Tyr Gly Gly Cys Gln Gly Asn Gly Asn Lys Phe Tyr Ser<br>             35                 40                 45 | | | | 247 |
| GAG AAG GAG TGC AGA GAG TAC TGC GGT GTC CCT GGT GAT GGT GAT GAG<br>Glu Lys Glu Cys Arg Glu Tyr Cys Gly Val Pro Gly Asp Gly Asp Glu<br>         50                 55                 60 | | | | 295 |
| GAG CTG CTG CGC TTC TCC AAC TGACAACTGG ATCCTCTACG CCGGAACGAT<br>Glu Leu Leu Arg Phe Ser Asn<br>     65                 70 | | | | 346 |
| CGT | | | | 349 |

( 2 ) INFORMATION FOR SEQ ID NO:4:

( i ) SEQUENCE CHARACTERISTICS:
    ( A ) LENGTH: 91 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

Met Lys Gln Ser Thr Ile Ala Leu Ala Leu Leu Pro Leu Leu Phe Thr
-21  -20              -15                 -10

Pro Val Thr Lys Ala Asp Asp Ala Ala Cys Asn Leu Pro Ile Val Arg
 -5            1                  5                 10

Gly Pro Cys Arg Ala Phe Ile Lys Leu Trp Ala Phe Asp Ala Val Lys
         15                 20                 25

Gly Lys Cys Val Leu Phe Pro Tyr Gly Gly Cys Gln Gly Asn Gly Asn
         30                 35                 40

Lys Phe Tyr Ser Glu Lys Glu Cys Arg Glu Tyr Cys Gly Val Pro Gly
         45                 50                 55

Asp Gly Asp Glu Glu Leu Leu Arg Phe Ser Asn
 60             65                 70

( 2 ) INFORMATION FOR SEQ ID NO:5:

( i ) SEQUENCE CHARACTERISTICS:
    ( A ) LENGTH: 343 base pairs
    ( B ) TYPE: nucleic acid (C) STRANDEDNESS: double
(D) TOPOLOGY: linear (ii) MOLECULE TYPE: DNA (genomic)

(iii) HYPOTHETICAL: NO (vi) ORIGINAL SOURCE:
(A) ORGANISM: Eschericia coli
(B) STRAIN: JE5505 (pM735)

(ix) FEATURE:
(A) NAME/KEY: -
(B) LOCATION: 1..343
(D) OTHER INFORMATION: /label=sequence
/ note= "as in Figure 22"

(ix) FEATURE:
(A) NAME/KEY: sig_peptide
(B) LOCATION: 43..105
(D) OTHER INFORMATION: /standard_name= "pho A signal peptide"

(ix) FEATURE:
(A) NAME/KEY: mat_peptide
(B) LOCATION: 106..309
(D) OTHER INFORMATION: /product="polypeptide Q19R"

(ix) FEATURE:
(A) NAME/KEY: CDS
(B) LOCATION: 43..309

(xi) SEQUENCE DESCRIPTION: SEQ ID NO:5:

```
ACGCAAGTTC ACGTAAAAGC TTAAAAAAGG GTATAAAATA AA ATG AAA CAA AGT           54
                                                Met Lys Gln Ser
                                                -21     -20

ACT ATT GCA CTG GCA CTC TTA CCG TTA CTG TTT ACC CCT GTG ACA AAG          102
Thr Ile Ala Leu Ala Leu Leu Pro Leu Leu Phe Thr Pro Val Thr Lys
        -15             -10                     -5

GCC GCG GCC TGT AAT CTA CCA ATA GTC CGG GGC CCC TGC CGA GCC TTC          150
Ala Ala Ala Cys Asn Leu Pro Ile Val Arg Gly Pro Cys Arg Ala Phe
        1           5                   10                  15

ATC CGT CTC TGG GCA TTT GAT GCT GTC AAG GGG AAG TGC GTC CTC TTC          198
Ile Arg Leu Trp Ala Phe Asp Ala Val Lys Gly Lys Cys Val Leu Phe
                20              25                      30

CCC TAC GGG GGC TGC CAG GGC AAC GGG AAC AAG TTC TAC TCA GAG AAG          246
Pro Tyr Gly Gly Cys Gln Gly Asn Gly Asn Lys Phe Tyr Ser Glu Lys
            35              40                      45

GAG TGC AGA GAG TAC TGC GGT GTC CCT GGT GAT GGT GAT GAG GAG CTG          294
Glu Cys Arg Glu Tyr Cys Gly Val Pro Gly Asp Gly Asp Glu Glu Leu
        50              55                      60

CTG CGC TTC TCC AAC TGACAACTGG ATCCTCTACG CCGGAACGCA TCGT                343
Leu Arg Phe Ser Asn
        65
```

(2) INFORMATION FOR SEQ ID NO:6:

(i) SEQUENCE CHARACTERISTICS:
(A) LENGTH: 89 amino acids
(B) TYPE: amino acid
(D) TOPOLOGY: linear (ii) MOLECULE TYPE: protein (xi) SEQUENCE DESCRIPTION: SEQ ID NO:6:

```
Met Lys Gln Ser Thr Ile Ala Leu Ala Leu Leu Pro Leu Leu Phe Thr
-21     -20                 -15                 -10

Pro Val Thr Lys Ala Ala Ala Cys Asn Leu Pro Ile Val Arg Gly Pro
    -5              1           5                   10
```

```
Cys Arg Ala Phe Ile Arg Leu Trp Ala Phe Asp Ala Val Lys Gly Lys
         15              20                  25

Cys Val Leu Phe Pro Tyr Gly Gly Cys Gln Gly Asn Gly Asn Lys Phe
         30              35              40

Tyr Ser Glu Lys Glu Cys Arg Glu Tyr Cys Gly Val Pro Gly Asp Gly
     45              50                  55

Asp Glu Glu Leu Leu Arg Phe Ser Asn
 60                  65
```

( 2 ) INFORMATION FOR SEQ ID NO:7:

( i ) SEQUENCE CHARACTERISTICS:
        ( A ) LENGTH: 344 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Eshericia coli
        ( B ) STRAIN: JE5505 (pM736)

( i x ) FEATURE:
        ( A ) NAME/KEY: -
        ( B ) LOCATION: 1..344
        ( D ) OTHER INFORMATION: /label=sequence
                / note= "as in Figure 24"

( i x ) FEATURE:
        ( A ) NAME/KEY: sig_peptide
        ( B ) LOCATION: 44..106
        ( D ) OTHER INFORMATION: /standard_name= "pho A signal
                sequence"

( i x ) FEATURE:
        ( A ) NAME/KEY: mat_peptide
        ( B ) LOCATION: 107..310
        ( D ) OTHER INFORMATION: /standard_name= "polypeptide
                Q19K/Y46E"

( i x ) FEATURE:
        ( A ) NAME/KEY: CDS
        ( B ) LOCATION: 44..310

( x i ) SEQUENCE DESCRIPTION: SEQ ID NO:7:

```
ACGCAAGTTC  ACGTAAAAAG  CTTAAAAAAG  GGTATAAAAT  AAA ATG AAA CAA AGT        55
                                                    Met Lys Gln Ser
                                                    -21 -20

ACT ATT GCA CTG GCA CTC TTA CCG TTA CTG TTT ACC CCT GTG ACA AAG           103
Thr Ile Ala Leu Ala Leu Leu Pro Leu Leu Phe Thr Pro Val Thr Lys
        -15             -10                     -5

GCC GCG GCC TGT AAT CTA CCA ATA GTC CGG GGC CCC TGC CGA GCC TTC           151
Ala Ala Ala Cys Asn Leu Pro Ile Val Arg Gly Pro Cys Arg Ala Phe
         1           5                  10                  15

ATC AAG CTC TGG GCA TTT GAT GCT GTC AAG GGG AAG TGC GTC CTC TTC           199
Ile Lys Leu Trp Ala Phe Asp Ala Val Lys Gly Lys Cys Val Leu Phe
             20                  25                  30

CCC TAC GGG GGC TGC CAG GGC AAC GGG AAC AAG TTC GAA TCA GAG AAG           247
Pro Tyr Gly Gly Cys Gln Gly Asn Gly Asn Lys Phe Glu Ser Glu Lys
             35                  40                  45

GAG TGC AGA GAG TAC TGC GGT GTC CCT GGT GAT GGT GAT GAG GAG CTG           295
Glu Cys Arg Glu Tyr Cys Gly Val Pro Gly Asp Gly Asp Glu Glu Leu
             50                  55                  60

CTG CGC TTC TCC AAC TGACAACTGG ATCCTCTACG CCGGAACGCA TCGT                 344
Leu Arg Phe Ser Asn
     65
```

5,589,360

( 2 ) INFORMATION FOR SEQ ID NO:8:

( i ) SEQUENCE CHARACTERISTICS:
        ( A ) LENGTH: 89 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met  Lys  Gln  Ser  Thr  Ile  Ala  Leu  Ala  Leu  Leu  Pro  Leu  Leu  Phe  Thr
-21  -20                      -15                      -10

Pro  Val  Thr  Lys  Ala  Ala  Ala  Cys  Asn  Leu  Pro  Ile  Val  Arg  Gly  Pro
 -5                            1              5                        10

Cys  Arg  Ala  Phe  Ile  Lys  Leu  Trp  Ala  Phe  Asp  Ala  Val  Lys  Gly  Lys
               15                    20                        25

Cys  Val  Leu  Phe  Pro  Tyr  Gly  Gly  Cys  Gln  Gly  Asn  Gly  Asn  Lys  Phe
          30                        35                        40

Glu  Ser  Glu  Lys  Glu  Cys  Arg  Glu  Tyr  Cys  Gly  Val  Pro  Gly  Asp  Gly
          45                   50                        55

Asp  Glu  Glu  Leu  Leu  Arg  Phe  Ser  Asn
 60                      65
```

( 2 ) INFORMATION FOR SEQ ID NO:9:

( i ) SEQUENCE CHARACTERISTICS:
        ( A ) LENGTH: 344 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Eschericia coli
        ( B ) STRAIN: JE5505 (pM726B)

( i x ) FEATURE:
        ( A ) NAME/KEY: -
        ( B ) LOCATION: 1..344
        ( D ) OTHER INFORMATION: /label=sequence
            / note= "as in Figure 27"

( i x ) FEATURE:
        ( A ) NAME/KEY: sig_peptide
        ( B ) LOCATION: 44..106
        ( D ) OTHER INFORMATION: /standard_name= "pho A signal
            peptide"

( i x ) FEATURE:
        ( A ) NAME/KEY: mat_peptide
        ( B ) LOCATION: 107..310
        ( D ) OTHER INFORMATION: /product="polypeptide R11E/Y46E"

( i x ) FEATURE:
        ( A ) NAME/KEY: CDS
        ( B ) LOCATION: 44..310

( x i ) SEQUENCE DESCRIPTION: SEQ ID NO:9:

```
ACGCAAGTTC  ACGTAAAAAG  CTTAAAAAAG  GGTATAAAAT  AAA ATG AAA CAA AGT        55
                                                   Met Lys Gln Ser
                                                   -21 -20

ACT ATT GCA CTG GCA CTC TTA CCG TTA CTG TTT ACC CCT GTG ACA AAG          103
Thr Ile Ala Leu Ala Leu Leu Pro Leu Leu Phe Thr Pro Val Thr Lys
    -15                      -10                    -5

GCC GCG GCC TGT AAT CTA CCA ATA GTC GAA GGC CCC TGC CGA GCC TTC          151
```

| Ala | Ala | Ala | Cys | Asn | Leu | Pro | Ile | Val | Glu | Gly | Pro | Cys | Arg | Ala | Phe |
|-----|-----|-----|-----|-----|-----|-----|-----|-----|-----|-----|-----|-----|-----|-----|-----|
| | 1 | | | 5 | | | | | 10 | | | | | | 15 |

| ATC | CAG | CTC | TGG | GCA | TTT | GAT | GCT | GTC | AAG | GGG | AAG | TGC | GTC | CTC | TTC | 199 |
|-----|-----|-----|-----|-----|-----|-----|-----|-----|-----|-----|-----|-----|-----|-----|-----|-----|
| Ile | Gln | Leu | Trp | Ala | Phe | Asp | Ala | Val | Lys | Gly | Lys | Cys | Val | Leu | Phe | |
| | | | | 20 | | | | 25 | | | | | | 30 | | |

| CCC | TAC | GGG | GGC | TGC | CAG | GGC | AAC | GGG | AAC | AAG | TTC | GAA | TCA | GAG | AAG | 247 |
|-----|-----|-----|-----|-----|-----|-----|-----|-----|-----|-----|-----|-----|-----|-----|-----|-----|
| Pro | Tyr | Gly | Gly | Cys | Gln | Gly | Asn | Gly | Asn | Lys | Phe | Glu | Ser | Glu | Lys | |
| | | | 35 | | | | | 40 | | | | | 45 | | | |

| GAG | TGC | AGA | GAG | TAC | TGC | GGT | GTC | CCT | GGT | GAT | GGT | GAT | GAG | GAG | CTG | 295 |
|-----|-----|-----|-----|-----|-----|-----|-----|-----|-----|-----|-----|-----|-----|-----|-----|-----|
| Glu | Cys | Arg | Glu | Tyr | Cys | Gly | Val | Pro | Gly | Asp | Gly | Asp | Glu | Glu | Leu | |
| | | 50 | | | | | 55 | | | | | 60 | | | | |

| CTG | CGC | TTC | TCC | AAC | TGACAACTGG | ATCCTCTACG | CCGGAACGCA | TCGT | 344 |
|-----|-----|-----|-----|-----|------------|------------|------------|------|-----|
| Leu | Arg | Phe | Ser | Asn | | | | | |
| | 65 | | | | | | | | |

( 2 ) INFORMATION FOR SEQ ID NO:10:

( i ) SEQUENCE CHARACTERISTICS:
        ( A ) LENGTH: 89 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| Met | Lys | Gln | Ser | Thr | Ile | Ala | Leu | Ala | Leu | Leu | Pro | Leu | Leu | Phe | Thr |
|-----|-----|-----|-----|-----|-----|-----|-----|-----|-----|-----|-----|-----|-----|-----|-----|
| -21 | -20 | | | | | | | -15 | | | | -10 | | | |

| Pro | Val | Thr | Lys | Ala | Ala | Ala | Cys | Asn | Leu | Pro | Ile | Val | Glu | Gly | Pro |
|-----|-----|-----|-----|-----|-----|-----|-----|-----|-----|-----|-----|-----|-----|-----|-----|
| -5  | | | | | 1 | | | | 5 | | | | | 10 | |

| Cys | Arg | Ala | Phe | Ile | Gln | Leu | Trp | Ala | Phe | Asp | Ala | Val | Lys | Gly | Lys |
|-----|-----|-----|-----|-----|-----|-----|-----|-----|-----|-----|-----|-----|-----|-----|-----|
| | | | 15 | | | | | 20 | | | | | 25 | | |

| Cys | Val | Leu | Phe | Pro | Tyr | Gly | Gly | Cys | Gln | Gly | Asn | Gly | Asn | Lys | Phe |
|-----|-----|-----|-----|-----|-----|-----|-----|-----|-----|-----|-----|-----|-----|-----|-----|
| | | 30 | | | | | 35 | | | | | 40 | | | |

| Glu | Ser | Glu | Lys | Glu | Cys | Arg | Glu | Tyr | Cys | Gly | Val | Pro | Gly | Asp | Gly |
|-----|-----|-----|-----|-----|-----|-----|-----|-----|-----|-----|-----|-----|-----|-----|-----|
| | 45 | | | | | 50 | | | | | 55 | | | | |

| Asp | Glu | Glu | Leu | Leu | Arg | Phe | Ser | Asn |
|-----|-----|-----|-----|-----|-----|-----|-----|-----|
| 60 | | | | | 65 | | | |

( 2 ) INFORMATION FOR SEQ ID NO:11:

( i ) SEQUENCE CHARACTERISTICS:
        ( A ) LENGTH: 344 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Eshericia coli
        ( B ) STRAIN: JE5505 (pM575C)

( i x ) FEATURE:
        ( A ) NAME/KEY: -
        ( B ) LOCATION: 1..344
        ( D ) OTHER INFORMATION: /label=sequence
            / note= "as in Figure 29"

( i x ) FEATURE:
        ( A ) NAME/KEY: sig_peptide
        ( B ) LOCATION: 44..106
        ( D ) OTHER INFORMATION: /standard_name= "pho A signal
            sequence"

( i x ) FEATURE:
        ( A ) NAME/KEY: mat_peptide ( B ) LOCATION: 107..310
( D ) OTHER INFORMATION: /standard_name= "polypeptide Y46E-AN"

( i x ) FEATURE:
( A ) NAME/KEY: CDS
( B ) LOCATION: 44..106

( x i ) SEQUENCE DESCRIPTION: SEQ ID NO:11:

```
ACGCAAGTTC ACGTAAAAAG CTTAAAAAAG GGTATAAAAT AAA ATG AAA CAA AGT        55
                                                Met Lys Gln Ser
                                                 1

ACT ATT GCA CTG GCA CTC TTA CCG TTA CTG TTT ACC CCT GTG ACA AAG        103
Thr Ile Ala Leu Ala Leu Leu Pro Leu Leu Phe Thr Pro Val Thr Lys
 5                   10                  15                  20

GCC GCGGCCTGTA ATCTACCAAT AGTCCGGGGC CCCTGCCGAG CCTTCATCCA             156
Ala

GCTCTGGGCA TTTGATGCTG TCAAGGGGAA GTGCGTCCTC TTCCCCTACG GGGGCTGCCA      216

GGGCAACGGG AACAAGTTCG AATCAGAGAA GGAGTGCAGA GAGTACTGCG GTGTCCCTGG      276

TGATGGTGAT GAGGAGCTGC TGCGCTTCTC CAACTGACAA CTGGATCCTC TACGCCGGAA      336

CGCATCGT                                                               344
```

( 2 ) INFORMATION FOR SEQ ID NO:12:

( i ) SEQUENCE CHARACTERISTICS:
( A ) LENGTH: 21 amino acids
( B ) TYPE: amino acid
( D ) TOPOLOGY: linear ( i i ) MOLECULE TYPE: protein ( x i ) SEQUENCE DESCRIPTION: SEQ ID NO:12:

```
Met Lys Gln Ser Thr Ile Ala Leu Ala Leu Leu Pro Leu Leu Phe Thr
 1               5                  10                  15

Pro Val Thr Lys Ala
                 20
```

( 2 ) INFORMATION FOR SEQ ID NO:13:

( i ) SEQUENCE CHARACTERISTICS:
( A ) LENGTH: 344 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( v i ) ORIGINAL SOURCE:
( A ) ORGANISM: Eschericia coli
( B ) STRAIN: JE5055 (pM576B)

( i x ) FEATURE:
( A ) NAME/KEY: -
( B ) LOCATION: 1..344
( D ) OTHER INFORMATION: /label=sequence
/ note= "as in Figure 31"

( i x ) FEATURE:
( A ) NAME/KEY: sig_peptide
( B ) LOCATION: 44..106
( D ) OTHER INFORMATION: /standard_name= "pho A signal sequence"

( i x ) FEATURE:
( A ) NAME/KEY: mat_peptide
( B ) LOCATION: 107..310
( D ) OTHER INFORMATION: /standard_name= "polypeptide

Q19K-AN"

(ix) FEATURE:
    (A) NAME/KEY: CDS
    (B) LOCATION: 44..310

(xi) SEQUENCE DESCRIPTION: SEQ ID NO:13:

| ACGCAAGTTC | ACGTAAAAAG | CTTAAAAAAG | GGTATAAAAT | AAA | ATG<br>Met<br>-21 | AAA<br>Lys<br>-20 | CAA<br>Gln | AGT<br>Ser | 55 |

| ACT | ATT | GCA | CTG | GCA | CTC | TTA | CCG | TTA | CTG | TTT | ACC | CCT | GTG | ACA | AAG | 103 |
| Thr | Ile | Ala | Leu | Ala | Leu | Leu | Pro | Leu | Leu | Phe | Thr | Pro | Val | Thr | Lys | |
| | | -15 | | | | | -10 | | | | | -5 | | | | |

| GCC | GCG | GCC | TGT | AAT | CTA | CCA | ATA | GTC | CGG | GGC | CCC | TGC | CGA | GCC | TTC | 151 |
| Ala | Ala | Ala | Cys | Asn | Leu | Pro | Ile | Val | Arg | Gly | Pro | Cys | Arg | Ala | Phe | |
| | | 1 | | | 5 | | | | | 10 | | | | | 15 | |

| ATC | AAG | CTC | TGG | GCA | TTT | GAT | GCT | GTC | AAG | GGG | AAG | TGC | GTC | CTC | TTC | 199 |
| Ile | Lys | Leu | Trp | Ala | Phe | Asp | Ala | Val | Lys | Gly | Lys | Cys | Val | Leu | Phe | |
| | | | | 20 | | | | | 25 | | | | | 30 | | |

| CCC | TAC | GGG | GGC | TGC | CAG | GGC | AAC | GGG | AAC | AAG | TTC | TAC | TCA | GAG | AAG | 247 |
| Pro | Tyr | Gly | Gly | Cys | Gln | Gly | Asn | Gly | Asn | Lys | Phe | Tyr | Ser | Glu | Lys | |
| | | | 35 | | | | | 40 | | | | | 45 | | | |

| GAG | TGC | AGA | GAG | TAC | TGC | GGT | GTC | CCT | GGT | GAT | GGT | GAT | GAG | GAG | CTG | 295 |
| Glu | Cys | Arg | Glu | Tyr | Cys | Gly | Val | Pro | Gly | Asp | Gly | Asp | Glu | Glu | Leu | |
| | | 50 | | | | | 55 | | | | | 60 | | | | |

| CTG | CGC | TTC | TCC | AAC | TGACAACTGG | ATCCTCTACG | CCGGAACGCA | TCGT | 344 |
| Leu | Arg | Phe | Ser | Asn | | | | | |
| 65 | | | | | | | | | |

(2) INFORMATION FOR SEQ ID NO:14:

(i) SEQUENCE CHARACTERISTICS:
        (A) LENGTH: 89 amino acids
        (B) TYPE: amino acid
        (D) TOPOLOGY: linear (ii) MOLECULE TYPE: protein (xi) SEQUENCE DESCRIPTION: SEQ ID NO:14:

| Met | Lys | Gln | Ser | Thr | Ile | Ala | Leu | Ala | Leu | Leu | Pro | Leu | Leu | Phe | Thr |
| -21 | -20 | | | | -15 | | | | | -10 | | | | | |

| Pro | Val | Thr | Lys | Ala | Ala | Ala | Cys | Asn | Leu | Pro | Ile | Val | Arg | Gly | Pro |
| -5 | | | | 1 | | | | 5 | | | | | | 10 | |

| Cys | Arg | Ala | Phe | Ile | Lys | Leu | Trp | Ala | Phe | Asp | Ala | Val | Lys | Gly | Lys |
| | | | 15 | | | | 20 | | | | | 25 | | | |

| Cys | Val | Leu | Phe | Pro | Tyr | Gly | Gly | Cys | Gln | Gly | Asn | Gly | Asn | Lys | Phe |
| | | 30 | | | | | 35 | | | | | 40 | | | |

| Tyr | Ser | Glu | Lys | Glu | Cys | Arg | Glu | Tyr | Cys | Gly | Val | Pro | Gly | Asp | Gly |
| | 45 | | | | | 50 | | | | | 55 | | | | |

| Asp | Glu | Glu | Leu | Leu | Arg | Phe | Ser | Asn |
| 60 | | | | | 65 | | | |

(2) INFORMATION FOR SEQ ID NO:15:

(i) SEQUENCE CHARACTERISTICS:
        (A) LENGTH: 344 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:

(A) ORGANISM: Eschericia coli
(B) STRAIN: JE5505 (pM737B)

(ix) FEATURE:
  (A) NAME/KEY: -
  (B) LOCATION: 1..344
  (D) OTHER INFORMATION: /label=sequence
      / note= "as in Figure 33"

(ix) FEATURE:
  (A) NAME/KEY: sig_peptide
  (B) LOCATION: 44..106
  (D) OTHER INFORMATION: /standard_name= "pho A signal peptide"

(ix) FEATURE:
  (A) NAME/KEY: mat_peptide
  (B) LOCATION: 107..310
  (D) OTHER INFORMATION: /standard_name= "polypeptide Q19R/Y46E"

(ix) FEATURE:
  (A) NAME/KEY: CDS
  (B) LOCATION: 44..310

(xi) SEQUENCE DESCRIPTION: SEQ ID NO:15:

```
ACGCAAGTTC ACGTAAAAAG CTTAAAAAAG GGTATAAAAT AAA ATG AAA CAA AGT        55
                                              Met Lys Gln Ser
                                              -21     -20

ACT ATT GCA CTG GCA CTC TTA CCG TTA CTG TTT ACC CCT GTG ACA AAG       103
Thr Ile Ala Leu Ala Leu Leu Pro Leu Leu Phe Thr Pro Val Thr Lys
        -15             -10                         -5

GCC GCG GCC TGT AAT CTA CCA ATA GTC CGG GGC CCC TGC CGA GCC TTC       151
Ala Ala Ala Cys Asn Leu Pro Ile Val Arg Gly Pro Cys Arg Ala Phe
         1            5                  10                 15

ATC CGT CTC TGG GCA TTT GAT GCT GTC AAG GGG AAG TGC GTC CTC TTC       199
Ile Arg Leu Trp Ala Phe Asp Ala Val Lys Gly Lys Cys Val Leu Phe
              20              25                     30

CCC TAC GGG GGC TGC CAG GGC AAC GGG AAC AAG TTC GAA TCA GAG AAG       247
Pro Tyr Gly Gly Cys Gln Gly Asn Gly Asn Lys Phe Glu Ser Glu Lys
            35              40                     45

GAG TGC AGA GAG TAC TGC GGT GTC CCT GGT GAT GGT GAT GAG GAG CTG       295
Glu Cys Arg Glu Tyr Cys Gly Val Pro Gly Asp Gly Asp Glu Glu Leu
        50              55                  60

CTG CGC TTC TCC AAC TGACAACTGG ATCCTCTACG CCGGAACGCA TCGT             344
Leu Arg Phe Ser Asn
        65
```

(2) INFORMATION FOR SEQ ID NO:16:

(i) SEQUENCE CHARACTERISTICS:
    (A) LENGTH: 89 amino acids
    (B) TYPE: amino acid
    (D) TOPOLOGY: linear (ii) MOLECULE TYPE: protein (xi) SEQUENCE DESCRIPTION: SEQ ID NO:16:

```
Met Lys Gln Ser Thr Ile Ala Leu Ala Leu Leu Pro Leu Leu Phe Thr
-21     -20             -15             -10

Pro Val Thr Lys Ala Ala Ala Cys Asn Leu Pro Ile Val Arg Gly Pro
    -5               1           5                      10

Cys Arg Ala Phe Ile Arg Leu Trp Ala Phe Asp Ala Val Lys Gly Lys
            15              20                     25

Cys Val Leu Phe Pro Tyr Gly Gly Cys Gln Gly Asn Gly Asn Lys Phe
            30              35                     40

Glu Ser Glu Lys Glu Cys Arg Glu Tyr Cys Gly Val Pro Gly Asp Gly
```

```
                              45                    50                      55
Asp Glu Glu Leu Leu Arg Phe Ser Asn
 60                   65
```

( 2 ) INFORMATION FOR SEQ ID NO:17:

( i ) SEQUENCE CHARACTERISTICS:
        ( A ) LENGTH: 379 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Eschericia coli
        ( B ) STRAIN: JE5505 (pM727)

( i x ) FEATURE:
        ( A ) NAME/KEY: -
        ( B ) LOCATION: 1..379
        ( D ) OTHER INFORMATION: /label=sequence
            / note= "as in Figure 36"

( i x ) FEATURE:
        ( A ) NAME/KEY: mat_peptide
        ( B ) LOCATION: 143..346
        ( D ) OTHER INFORMATION: /standard_name= "Q19K/Y46D peptide"

( i x ) FEATURE:
        ( A ) NAME/KEY: CDS
        ( B ) LOCATION: 44..346

( x i ) SEQUENCE DESCRIPTION: SEQ ID NO:17:

```
ACGCAAGTTC ACGTAAAAAG CTTAAAAAAG GGTATAAAAT AAA ATG AAA CAA AGT          55
                                               Met Lys Gln Ser
                                               -33           -30

ACT ATT GCA CTG GCA CTC TTA CCG TTA CTG TTT ACC CCT GTG ACA AAG         103
Thr Ile Ala Leu Ala Leu Leu Pro Leu Leu Phe Thr Pro Val Thr Lys
            -25                 -20                     -15

GCC GCT GTG CTA CCG CAA GAA GAA GAA GGC TCG GGT ATG GCC GCC TGT         151
Ala Ala Val Leu Pro Gln Glu Glu Glu Gly Ser Gly Met Ala Ala Cys
            -10                  -5                  1

AAT CTA CCA ATA GTC CGG GGC CCC TGC CGA GCC TTC ATC AAG CTC TGG         199
Asn Leu Pro Ile Val Arg Gly Pro Cys Arg Ala Phe Ile Lys Leu Trp
         5              10                  15

GCA TTT GAT GCT GTC AAG GGG AAG TGC GTC CTC TTC CCC TAC GGG GGC         247
Ala Phe Asp Ala Val Lys Gly Lys Cys Val Leu Phe Pro Tyr Gly Gly
 20              25                  30                      35

TGC CAG GGC AAC GGG AAC AAG TTC GAC TCA GAG AAG GAG TGC AGA GAG         295
Cys Gln Gly Asn Gly Asn Lys Phe Asp Ser Glu Lys Glu Cys Arg Glu
                 40                  45                  50

TAC TGC GGT GTC CCT GGT GAT GGT GAT GAG GAG CTG CTG CGC TTC TCC         343
Tyr Cys Gly Val Pro Gly Asp Gly Asp Glu Glu Leu Leu Arg Phe Ser
             55                  60                  65

AAC TGACAACTGG ATCCTCTACG CCGGACGCAT CGT                                379
Asn
```

( 2 ) INFORMATION FOR SEQ ID NO:18:

( i ) SEQUENCE CHARACTERISTICS:
        ( A ) LENGTH: 101 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

| Met | Lys | Gln | Ser | Thr | Ile | Ala | Leu | Ala | Leu | Leu | Pro | Leu | Leu | Phe | Thr |
|-----|-----|-----|-----|-----|-----|-----|-----|-----|-----|-----|-----|-----|-----|-----|-----|
| -33 |     |     | -30 |     |     |     |     | -25 |     |     |     |     | -20 |     |     |

| Pro | Val | Thr | Lys | Ala | Ala | Val | Leu | Pro | Gln | Glu | Glu | Glu | Gly | Ser | Gly |
|     |     | -15 |     |     |     |     | -10 |     |     |     |     | -5  |     |     |     |

| Met | Ala | Ala | Cys | Asn | Leu | Pro | Ile | Val | Arg | Gly | Pro | Cys | Arg | Ala | Phe |
| 1   |     |     |     |     | 5   |     |     |     |     | 10  |     |     |     |     | 15  |

| Ile | Lys | Leu | Trp | Ala | Phe | Asp | Ala | Val | Lys | Gly | Lys | Cys | Val | Leu | Phe |
|     |     |     |     | 20  |     |     |     |     | 25  |     |     |     |     | 30  |     |

| Pro | Tyr | Gly | Gly | Cys | Gln | Gly | Asn | Gly | Asn | Lys | Phe | Asp | Ser | Glu | Lys |
|     |     |     | 35  |     |     |     |     | 40  |     |     |     |     | 45  |     |     |

| Glu | Cys | Arg | Glu | Tyr | Cys | Gly | Val | Pro | Gly | Asp | Gly | Asp | Glu | Glu | Leu |
|     |     | 50  |     |     |     |     | 55  |     |     |     |     | 60  |     |     |     |

| Leu | Arg | Phe | Ser | Asn |
|     | 65  |     |     |     |

( 2 ) INFORMATION FOR SEQ ID NO:19:

( i ) SEQUENCE CHARACTERISTICS:
        ( A ) LENGTH: 379 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Eshericia coli
        ( B ) STRAIN: JE5505 (pM744)

( i x ) FEATURE:
        ( A ) NAME/KEY: -
        ( B ) LOCATION: 1..379
        ( D ) OTHER INFORMATION: /label=sequence
            / note= "as in Figure 37"

( i x ) FEATURE:
        ( A ) NAME/KEY: mat_peptide
        ( B ) LOCATION: 143..346
        ( D ) OTHER INFORMATION: /standard_name= "Q19R/Y46D
            polypeptide"

( i x ) FEATURE:
        ( A ) NAME/KEY: CDS
        ( B ) LOCATION: 44..346

( x i ) SEQUENCE DESCRIPTION: SEQ ID NO:19:

```
ACGCAAGTTC  ACGTAAAAAG  CTTAAAAAAG  GGTATAAAAT  AAA ATG AAA CAA AGT        55
                                                    Met Lys Gln Ser
                                                    -33         -30

ACT ATT GCA CTG GCA CTC TTA CCG TTA CTG TTT ACC CCT GTG ACA AAG           103
Thr Ile Ala Leu Ala Leu Leu Pro Leu Leu Phe Thr Pro Val Thr Lys
            -25             -20                         -15

GCC GCT GTG CTA CCG CAA GAA GAA GAA GGC TCG GGT ATG GCC GCC TGT           151
Ala Ala Val Leu Pro Gln Glu Glu Glu Gly Ser Gly Met Ala Ala Cys
            -10             -5                       1

AAT CTA CCA ATA GTC CGG GGC CCC TGC CGA GCC TTC ATC CGT CTC TGG           199
Asn Leu Pro Ile Val Arg Gly Pro Cys Arg Ala Phe Ile Arg Leu Trp
        5               10              15

GCA TTT GAT GCT GTC AAG GGG AAG TGC GTC CTC TTC CCC TAC GGG GGC           247
Ala Phe Asp Ala Val Lys Gly Lys Cys Val Leu Phe Pro Tyr Gly Gly
 20              25              30              35

TGC CAG GGC AAC GGG AAC AAG TTC GAC TCA GAG AAG GAG TGC AGA GAG           295
Cys Gln Gly Asn Gly Asn Lys Phe Asp Ser Glu Lys Glu Cys Arg Glu
```

```
                         40                         45                           50
TAC  TGC  GGT  GTC  CCT  GGT  GAT  GGT  GAT  GAG  GAG  CTG  CTG  CGC  TTC  TCC         343
Tyr  Cys  Gly  Val  Pro  Gly  Asp  Gly  Asp  Glu  Glu  Leu  Leu  Arg  Phe  Ser
               55                         60                         65

AAC  TGACAACTGG  ATCCTCTACG  CCGGACGCAT  CGT                                            379
Asn
```

( 2 ) INFORMATION FOR SEQ ID NO:20:

( i ) SEQUENCE CHARACTERISTICS:
        ( A ) LENGTH: 101 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

```
Met  Lys  Gln  Ser  Thr  Ile  Ala  Leu  Ala  Leu  Leu  Pro  Leu  Leu  Phe  Thr
-33            -30                      -25                      -20

Pro  Val  Thr  Lys  Ala  Ala  Val  Leu  Pro  Gln  Glu  Glu  Glu  Gly  Ser  Gly
          -15                      -10                      -5

Met  Ala  Ala  Cys  Asn  Leu  Pro  Ile  Val  Arg  Gly  Pro  Cys  Arg  Ala  Phe
 1                  5                        10                           15

Ile  Arg  Leu  Trp  Ala  Phe  Asp  Ala  Val  Lys  Gly  Lys  Cys  Val  Leu  Phe
               20                       25                            30

Pro  Tyr  Gly  Gly  Cys  Gln  Gly  Asn  Gly  Asn  Lys  Phe  Asp  Ser  Glu  Lys
               35                       40                       45

Glu  Cys  Arg  Glu  Tyr  Cys  Gly  Val  Pro  Gly  Asp  Gly  Asp  Glu  Glu  Leu
          50                       55                       60

Leu  Arg  Phe  Ser  Asn
          65
```

( 2 ) INFORMATION FOR SEQ ID NO:21:

( i ) SEQUENCE CHARACTERISTICS:
        ( A ) LENGTH: 380 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Eschericia coli
        ( B ) STRAIN: JE5505 (pM741)

( i x ) FEATURE:
        ( A ) NAME/KEY: -
        ( B ) LOCATION: 1..380
        ( D ) OTHER INFORMATION: /label=sequence
            / note= "as in Figure 39"

( i x ) FEATURE:
        ( A ) NAME/KEY: mat_peptide
        ( B ) LOCATION: 145..347
        ( D ) OTHER INFORMATION: /standard_name= "polypeptide
            R11Q/Q19K/Y46D"

( i x ) FEATURE:
        ( A ) NAME/KEY: CDS
        ( B ) LOCATION: 45..347

( x i ) SEQUENCE DESCRIPTION: SEQ ID NO:21:

```
ACGCAAGTTC  ACGTAAAAAA  GCTTAAAAAA  GGGTATAAAA  TAAA ATG  AAA  CAA  AGT     56
                                                     Met  Lys  Gln  Ser
                                                     -33            -30
```

```
ACT ATT GCA CTG GCA CTC TTA CCG TTA CTG TTT ACC CCT GTG ACA AAG      104
Thr Ile Ala Leu Ala Leu Leu Pro Leu Leu Phe Thr Pro Val Thr Lys
            -25                 -20                     -15

GCC GCT GTG CTA CCG CAA GAA GAA GAA GGC TCG GGT ATG GCC GCC TGT      152
Ala Ala Val Leu Pro Gln Glu Glu Glu Gly Ser Gly Met Ala Ala Cys
            -10                  -5                      1

AAT CTA CCA ATA GTC CAG GGC CCC TGC CGA GCC TTC ATC AAG CTC TGG      200
Asn Leu Pro Ile Val Gln Gly Pro Cys Arg Ala Phe Ile Lys Leu Trp
     5               10                      15

GCA TTT GAT GCT GTC AAG GGG AAG TGC GTC CTC TTC CCC TAC GGG GGC      248
Ala Phe Asp Ala Val Lys Gly Lys Cys Val Leu Phe Pro Tyr Gly Gly
 20              25                  30                      35

TGC CAG GGC AAC GGG AAC AAG TTC GAC TCA GAG AAG GAG TGC AGA GAG      296
Cys Gln Gly Asn Gly Asn Lys Phe Asp Ser Glu Lys Glu Cys Arg Glu
             40              45                      50

TAC TGC GGT GTC CCT GGT GAT GGT GAT GAG GAG CTG CTG CGC TTC TCC      344
Tyr Cys Gly Val Pro Gly Asp Gly Asp Glu Glu Leu Leu Arg Phe Ser
             55              60                      65

AAC TGACAACTGG ATCCTCTACG CCGGACGCAT CGT                              380
Asn
```

( 2 ) INFORMATION FOR SEQ ID NO:22:

( i ) SEQUENCE CHARACTERISTICS:
        ( A ) LENGTH: 101 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

```
Met Lys Gln Ser Thr Ile Ala Leu Ala Leu Leu Pro Leu Leu Phe Thr
-33          -30                 -25                 -20

Pro Val Thr Lys Ala Ala Val Leu Pro Gln Glu Glu Glu Gly Ser Gly
         -15                 -10                  -5

Met Ala Ala Cys Asn Leu Pro Ile Val Gln Gly Pro Cys Arg Ala Phe
      1              5               10                      15

Ile Lys Leu Trp Ala Phe Asp Ala Val Lys Gly Lys Cys Val Leu Phe
             20                  25                      30

Pro Tyr Gly Gly Cys Gln Gly Asn Gly Asn Lys Phe Asp Ser Glu Lys
             35              40                      45

Glu Cys Arg Glu Tyr Cys Gly Val Pro Gly Asp Gly Asp Glu Glu Leu
             50              55                      60

Leu Arg Phe Ser Asn
 65
```

( 2 ) INFORMATION FOR SEQ ID NO:23:

( i ) SEQUENCE CHARACTERISTICS:
        ( A ) LENGTH: 379 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Eschericia coli
        ( B ) STRAIN: JE5505 (pM742)

( i x ) FEATURE:
        ( A ) NAME/KEY: -

(B) LOCATION: 1..379
(D) OTHER INFORMATION: /label=sequence
            / note= "as in Figure 41"

(ix) FEATURE:
       (A) NAME/KEY: mat_peptide
       (B) LOCATION: 143..346
       (D) OTHER INFORMATION: /standard_name= "polypeptide
            R11D/Q19K/Y46D"

(ix) FEATURE:
       (A) NAME/KEY: CDS
       (B) LOCATION: 44..346

(xi) SEQUENCE DESCRIPTION: SEQ ID NO:23:

| | | | | | | | | | | | | | | | |
|---|---|---|---|---|---|---|---|---|---|---|---|---|---|---|---|
| ACGCAAGTTC | ACGTAAAAAG | CTTAAAAAAG | GGTATAAAAT | AAA | ATG<br>Met<br>-33 | AAA<br>Lys | CAA<br>Gln | AGT<br>Ser<br>-30 | | | | | | | 55 |
| ACT<br>Thr | ATT<br>Ile | GCA<br>Ala | CTG<br>Leu<br>-25 | GCA<br>Ala | CTC<br>Leu | TTA<br>Leu | CCG<br>Pro | TTA<br>Leu | CTG<br>Leu<br>-20 | TTT<br>Phe | ACC<br>Thr | CCT<br>Pro | GTG<br>Val | ACA AAG<br>Thr Lys<br>-15 | 103 |
| GCC<br>Ala | GCT<br>Ala | GTG<br>Val | CTA<br>Leu<br>-10 | CCG<br>Pro | CAA<br>Gln | GAA<br>Glu | GAA<br>Glu | GAA<br>Glu | GGC<br>Gly<br>-5 | TCG<br>Ser | GGT<br>Gly | ATG<br>Met | GCC<br>Ala<br>1 | GCC TGT<br>Ala Cys | 151 |
| AAT<br>Asn | CTA<br>Leu<br>5 | CCA<br>Pro | ATA<br>Ile | GTC<br>Val | GAT<br>Asp | GGC<br>Gly<br>10 | CCC<br>Pro | TGC<br>Cys | CGA<br>Arg | GCC<br>Ala | TTC<br>Phe<br>15 | ATC<br>Ile | AAG<br>Lys | CTC TGG<br>Leu Trp | 199 |
| GCA<br>Ala<br>20 | TTT<br>Phe | GAT<br>Asp | GCT<br>Ala | GTC<br>Val | AAG<br>Lys<br>25 | GGG<br>Gly | AAG<br>Lys | TGC<br>Cys | GTC<br>Val | CTC<br>Leu<br>30 | TTC<br>Phe | CCC<br>Pro | TAC<br>Tyr | GGG GGC<br>Gly Gly<br>35 | 247 |
| TGC<br>Cys | CAG<br>Gln | GGC<br>Gly | AAC<br>Asn | GGG<br>Gly<br>40 | AAC<br>Asn | AAG<br>Lys | TTC<br>Phe | GAC<br>Asp | TCA<br>Ser<br>45 | GAG<br>Glu | AAG<br>Lys | GAG<br>Glu | TGC<br>Cys | AGA GAG<br>Arg Glu<br>50 | 295 |
| TAC<br>Tyr | TGC<br>Cys | GGT<br>Gly | GTC<br>Val<br>55 | CCT<br>Pro | GGT<br>Gly | GAT<br>Asp | GGT<br>Gly | GAT<br>Asp<br>60 | GAG<br>Glu | GAG<br>Glu | CTG<br>Leu | CTG<br>Leu | CGC<br>Arg<br>65 | TTC TCC<br>Phe Ser | 343 |
| AAC<br>Asn | TGACAACTGG | ATCCTCTACG | CCGGACGCAT | CGT | | | | | | | | | | | 379 |

(2) INFORMATION FOR SEQ ID NO:24:

(i) SEQUENCE CHARACTERISTICS:
       (A) LENGTH: 101 amino acids
       (B) TYPE: amino acid
       (D) TOPOLOGY: linear (ii) MOLECULE TYPE: protein (xi) SEQUENCE DESCRIPTION: SEQ ID NO:24:

Met Lys Gln Ser Thr Ile Ala Leu Ala Leu Leu Pro Leu Leu Phe Thr
-33              -30                  -25                  -20

Pro Val Thr Lys Ala Ala Val Leu Pro Gln Glu Glu Glu Gly Ser Gly
         -15                  -10                  -5

Met Ala Ala Cys Asn Leu Pro Ile Val Asp Gly Pro Cys Arg Ala Phe
     1                   5                   10                  15

Ile Lys Leu Trp Ala Phe Asp Ala Val Lys Gly Lys Cys Val Leu Phe
                    20                  25                  30

Pro Tyr Gly Gly Cys Gln Gly Asn Gly Asn Lys Phe Asp Ser Glu Lys
             35                  40                  45

Glu Cys Arg Glu Tyr Cys Gly Val Pro Gly Asp Gly Asp Glu Glu Leu
         50                  55                  60

Leu Arg Phe Ser Asn
     65

(2) INFORMATION FOR SEQ ID NO:25:

(i) SEQUENCE CHARACTERISTICS:
        (A) LENGTH: 379 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (A) ORGANISM: Eschericia coli
        (B) STRAIN: JE5505 (pM743)

(ix) FEATURE:
        (A) NAME/KEY: -
        (B) LOCATION: 1..379
        (D) OTHER INFORMATION: /label=sequence
            / note= "as in Figure 43"

(ix) FEATURE:
        (A) NAME/KEY: mat_peptide
        (B) LOCATION: 143..346
        (D) OTHER INFORMATION: /standard_name= "polypeptide
            R11L/Q19K/Y46D"

(ix) FEATURE:
        (A) NAME/KEY: CDS
        (B) LOCATION: 44..346

(xi) SEQUENCE DESCRIPTION: SEQ ID NO:25:

```
ACGCAAGTTC  ACGTAAAAAG  CTTAAAAAAG  GGTATAAAAT  AAA  ATG  AAA  CAA  AGT         55
                                                     Met  Lys  Gln  Ser
                                                     -33            -30

ACT  ATT  GCA  CTG  GCA  CTC  TTA  CCG  TTA  CTG  TTT  ACC  CCT  GTG  ACA  AAG    103
Thr  Ile  Ala  Leu  Ala  Leu  Leu  Pro  Leu  Leu  Phe  Thr  Pro  Val  Thr  Lys
               -25                     -20                          -15

GCC  GCT  GTG  CTA  CCG  CAA  GAA  GAA  GAA  GGC  TCG  GGT  ATG  GCC  GCC  TGT    151
Ala  Ala  Val  Leu  Pro  Gln  Glu  Glu  Glu  Gly  Ser  Gly  Met  Ala  Ala  Cys
               -10                      -5                     1

AAT  CTA  CCA  ATA  GTC  CTG  GGC  CCC  TGC  CGA  GCC  TTC  ATC  AAG  CTC  TGG    199
Asn  Leu  Pro  Ile  Val  Leu  Gly  Pro  Cys  Arg  Ala  Phe  Ile  Lys  Leu  Trp
          5                        10                      15

GCA  TTT  GAT  GCT  GTC  AAG  GGG  AAG  TGC  GTC  CTC  TTC  CCC  TAC  GGG  GGC    247
Ala  Phe  Asp  Ala  Val  Lys  Gly  Lys  Cys  Val  Leu  Phe  Pro  Tyr  Gly  Gly
20                       25                       30                       35

TGC  CAG  GGC  AAC  GGG  AAC  AAG  TTC  GAC  TCA  GAG  AAG  GAG  TGC  AGA  GAG    295
Cys  Gln  Gly  Asn  Gly  Asn  Lys  Phe  Asp  Ser  Glu  Lys  Glu  Cys  Arg  Glu
                    40                      45                      50

TAC  TGC  GGT  GTC  CCT  GGT  GAT  GGT  GAT  GAG  GAG  CTG  CTG  CGC  TTC  TCC    343
Tyr  Cys  Gly  Val  Pro  Gly  Asp  Gly  Asp  Glu  Glu  Leu  Leu  Arg  Phe  Ser
               55                       60                           65

AAC  TGACAACTGG  ATCCTCTACG  CCGGACGCAT  CGT                                      379
Asn
```

(2) INFORMATION FOR SEQ ID NO:26:

(i) SEQUENCE CHARACTERISTICS:
        (A) LENGTH: 101 amino acids
        (B) TYPE: amino acid
        (D) TOPOLOGY: linear (ii) MOLECULE TYPE: protein (xi) SEQUENCE DESCRIPTION: SEQ ID NO:26:

```
Met  Lys  Gln  Ser  Thr  Ile  Ala  Leu  Ala  Leu  Leu  Pro  Leu  Leu  Phe  Thr
-33            -30                      -25                          -20
```

```
Pro  Val  Thr  Lys  Ala  Ala  Val  Leu  Pro  Gln  Glu  Glu  Glu  Gly  Ser  Gly
          -15                      -10                      -5

Met  Ala  Ala  Cys  Asn  Leu  Pro  Ile  Val  Leu  Gly  Pro  Cys  Arg  Ala  Phe
     1              5                        10                            15

Ile  Lys  Leu  Trp  Ala  Phe  Asp  Ala  Val  Lys  Gly  Lys  Cys  Val  Leu  Phe
                    20                       25                      30

Pro  Tyr  Gly  Gly  Cys  Gln  Gly  Asn  Gly  Asn  Lys  Phe  Asp  Ser  Glu  Lys
               35                      40                           45

Glu  Cys  Arg  Glu  Tyr  Cys  Gly  Val  Pro  Gly  Asp  Gly  Asp  Glu  Glu  Leu
          50                       55                      60

Leu  Arg  Phe  Ser  Asn
     65
```

( 2 ) INFORMATION FOR SEQ ID NO:27:

( i ) SEQUENCE CHARACTERISTICS:
    ( A ) LENGTH: 379 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( v i ) ORIGINAL SOURCE:
    ( A ) ORGANISM: Eschericia coli
    ( B ) STRAIN: JE5505 (pM738)

( i x ) FEATURE:
    ( A ) NAME/KEY: -
    ( B ) LOCATION: 1..379
    ( D ) OTHER INFORMATION: /label=sequence
      / note= "as in Figure 44"

( i x ) FEATURE:
    ( A ) NAME/KEY: mat_peptide
    ( B ) LOCATION: 143..346
    ( D ) OTHER INFORMATION: /standard_name= "polypeptide
      R11E/Q19K/Y46E"

( i x ) FEATURE:
    ( A ) NAME/KEY: CDS
    ( B ) LOCATION: 44..346

( x i ) SEQUENCE DESCRIPTION: SEQ ID NO:27:

```
ACGCAAGTTC  ACGTAAAAAG  CTTAAAAAAG  GGTATAAAAT  AAA  ATG  AAA  CAA  AGT        55
                                                    Met  Lys  Gln  Ser
                                                    -33            -30

ACT  ATT  GCA  CTG  GCA  CTC  TTA  CCG  TTA  CTG  TTT  ACC  CCT  GTG  ACA  AAG  103
Thr  Ile  Ala  Leu  Ala  Leu  Leu  Pro  Leu  Leu  Phe  Thr  Pro  Val  Thr  Lys
               -25                      -20                           -15

GCC  GCT  GTG  CTA  CCG  CAA  GAA  GAA  GAA  GGC  TCG  GGT  ATG  GCC  GCC  TGT  151
Ala  Ala  Val  Leu  Pro  Gln  Glu  Glu  Glu  Gly  Ser  Gly  Met  Ala  Ala  Cys
               -10                      -5                        1

AAT  CTA  CCA  ATA  GTC  GAA  GGC  CCC  TGC  CGA  GCC  TTC  ATC  AAG  CTC  TGG  199
Asn  Leu  Pro  Ile  Val  Glu  Gly  Pro  Cys  Arg  Ala  Phe  Ile  Lys  Leu  Trp
          5                   10                           15

GCA  TTT  GAT  GCT  GTC  AAG  GGG  AAG  TGC  GTC  CTC  TTC  CCC  TAC  GGG  GGC  247
Ala  Phe  Asp  Ala  Val  Lys  Gly  Lys  Cys  Val  Leu  Phe  Pro  Tyr  Gly  Gly
20                  25                      30                           35

TGC  CAG  GGC  AAC  GGG  AAC  AAG  TTC  GAA  TCA  GAG  AAG  GAG  TGC  AGA  GAG  295
Cys  Gln  Gly  Asn  Gly  Asn  Lys  Phe  Glu  Ser  Glu  Lys  Glu  Cys  Arg  Glu
               40                      45                           50

TAC  TGC  GGT  GTC  CCT  GGT  GAT  GGT  GAT  GAG  GAG  CTG  CTG  CGC  TTC  TCC  343
Tyr  Cys  Gly  Val  Pro  Gly  Asp  Gly  Asp  Glu  Glu  Leu  Leu  Arg  Phe  Ser
```

```
                         55                        60                         65
AAC  TGACAACTGG  ATCCTCTACG  CCGGACGCAT  CGT                                              379
Asn
```

( 2 ) INFORMATION FOR SEQ ID NO:28:

( i ) SEQUENCE CHARACTERISTICS:
        ( A ) LENGTH: 101 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

```
Met  Lys  Gln  Ser  Thr  Ile  Ala  Leu  Ala  Leu  Leu  Pro  Leu  Leu  Phe  Thr
-33            -30                      -25                      -20

Pro  Val  Thr  Lys  Ala  Ala  Val  Leu  Pro  Gln  Glu  Glu  Glu  Gly  Ser  Gly
          -15                      -10                      -5

Met  Ala  Ala  Cys  Asn  Leu  Pro  Ile  Val  Glu  Gly  Pro  Cys  Arg  Ala  Phe
  1                      5                      10                           15

Ile  Lys  Leu  Trp  Ala  Phe  Asp  Ala  Val  Lys  Gly  Lys  Cys  Val  Leu  Phe
               20                      25                           30

Pro  Tyr  Gly  Gly  Cys  Gln  Gly  Asn  Gly  Asn  Lys  Phe  Glu  Ser  Glu  Lys
          35                      40                           45

Glu  Cys  Arg  Glu  Tyr  Cys  Gly  Val  Pro  Gly  Asp  Gly  Asp  Glu  Glu  Leu
          50                      55                           60

Leu  Arg  Phe  Ser  Asn
          65
```

( 2 ) INFORMATION FOR SEQ ID NO:29:

( i ) SEQUENCE CHARACTERISTICS:
        ( A ) LENGTH: 343 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Eschericia coli
        ( B ) STRAIN: JE5505 (pM764)

( i x ) FEATURE:
        ( A ) NAME/KEY: mat_peptide
        ( B ) LOCATION: 126..329

( i x ) FEATURE:
        ( A ) NAME/KEY: CDS
        ( B ) LOCATION: 27..329

( x i ) SEQUENCE DESCRIPTION: SEQ ID NO:29:

```
AAGCTTAAAA  AAGGGTATAA  AATAAA  ATG  AAA  CAA  AGT  ACT  ATT  GCA  CTG  GCA       53
                                Met  Lys  Gln  Ser  Thr  Ile  Ala  Leu  Ala
                                -33            -30                      -25

CTC  TTA  CCG  TTA  CTG  TTT  ACC  CCT  GTG  ACA  AAG  GCC  GCT  GTG  CTA  CCG   101
Leu  Leu  Pro  Leu  Leu  Phe  Thr  Pro  Val  Thr  Lys  Ala  Ala  Val  Leu  Pro
          -20                           -15                           -10

CAA  GAA  GAA  GAA  GGC  TCG  GGT  ATG  GCC  GCC  TGT  AAT  CTA  CCA  ATA  GTC   149
Gln  Glu  Glu  Glu  Gly  Ser  Gly  Met  Ala  Ala  Cys  Asn  Leu  Pro  Ile  Val
               -5                        1                      5

AAC  GGC  CCC  TGC  CGA  GCC  TTC  ATC  AAG  CTC  TGG  GCA  TTT  GAT  GCT  GTC   197
Asn  Gly  Pro  Cys  Arg  Ala  Phe  Ile  Lys  Leu  Trp  Ala  Phe  Asp  Ala  Val
          10                      15                      20
```

| | | | | | | | | | | | | | | | |
|---|---|---|---|---|---|---|---|---|---|---|---|---|---|---|---|
| AAG | GGG | AAG | TGC | GTC | CTC | TTC | CCC | TAC | GGG | GGC | TGC | CAG | GGC | AAC | GGG | 245 |
| Lys | Gly | Lys | Cys | Val | Leu | Phe | Pro | Tyr | Gly | Gly | Cys | Gln | Gly | Asn | Gly |
| 25 | | | | 30 | | | | | 35 | | | | | 40 |

| AAC | AAG | TTC | GAC | TCA | GAG | AAG | GAG | TGC | AGA | GAG | TAC | TGC | GGT | GTC | CCT | 293 |
|---|---|---|---|---|---|---|---|---|---|---|---|---|---|---|---|
| Asn | Lys | Phe | Asp | Ser | Glu | Lys | Glu | Cys | Arg | Glu | Tyr | Cys | Gly | Val | Pro |
| | | | | 45 | | | | 50 | | | | | | 55 |

| GGT | GAT | GGT | GAT | GAG | GAG | CTG | CTG | CGC | TTC | TCC | AAC | TGACAACTGG | 339 |
|---|---|---|---|---|---|---|---|---|---|---|---|---|---|
| Gly | Asp | Gly | Asp | Glu | Glu | Leu | Leu | Arg | Phe | Ser | Asn |
| | | | 60 | | | | | 65 |

ATCC 343

( 2 ) INFORMATION FOR SEQ ID NO:30:

( i ) SEQUENCE CHARACTERISTICS:
        ( A ) LENGTH: 101 amino acids
        ( B ) TYPE: amino acid
        ( D ) TOPOLOGY: linear ( i i ) MOLECULE TYPE: protein ( x i ) SEQUENCE DESCRIPTION: SEQ ID NO:30:

| Met | Lys | Gln | Ser | Thr | Ile | Ala | Leu | Ala | Leu | Leu | Pro | Leu | Leu | Phe | Thr |
|---|---|---|---|---|---|---|---|---|---|---|---|---|---|---|---|
| -33 | | | -30 | | | | | -25 | | | | | -20 | | |

| Pro | Val | Thr | Lys | Ala | Ala | Val | Leu | Pro | Gln | Glu | Glu | Glu | Gly | Ser | Gly |
|---|---|---|---|---|---|---|---|---|---|---|---|---|---|---|---|
| | | -15 | | | | | -10 | | | | | -5 | | | |

| Met | Ala | Ala | Cys | Asn | Leu | Pro | Ile | Val | Asn | Gly | Pro | Cys | Arg | Ala | Phe |
|---|---|---|---|---|---|---|---|---|---|---|---|---|---|---|---|
| | 1 | | | | 5 | | | | | 10 | | | | | 15 |

| Ile | Lys | Leu | Trp | Ala | Phe | Asp | Ala | Val | Lys | Gly | Lys | Cys | Val | Leu | Phe |
|---|---|---|---|---|---|---|---|---|---|---|---|---|---|---|---|
| | | | | 20 | | | | | 25 | | | | | 30 | |

| Pro | Tyr | Gly | Gly | Cys | Gln | Gly | Asn | Gly | Asn | Lys | Phe | Asp | Ser | Glu | Lys |
|---|---|---|---|---|---|---|---|---|---|---|---|---|---|---|---|
| | | | 35 | | | | | 40 | | | | | 45 | | |

| Glu | Cys | Arg | Glu | Tyr | Cys | Gly | Val | Pro | Gly | Asp | Gly | Asp | Glu | Glu | Leu |
|---|---|---|---|---|---|---|---|---|---|---|---|---|---|---|---|
| | | 50 | | | | | 55 | | | | | 60 | | | |

| Leu | Arg | Phe | Ser | Asn |
|---|---|---|---|---|
| | 65 | | | |

( 2 ) INFORMATION FOR SEQ ID NO:31:

( i ) SEQUENCE CHARACTERISTICS:
        ( A ) LENGTH: 343 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Eshericia coli
        ( B ) STRAIN: JE5505 (pM763)

( i x ) FEATURE:
        ( A ) NAME/KEY: sig_peptide
        ( B ) LOCATION: 27..89

( i x ) FEATURE:
        ( A ) NAME/KEY: mat_peptide
        ( B ) LOCATION: 90..329

( i x ) FEATURE:
        ( A ) NAME/KEY: CDS
        ( B ) LOCATION: 27..329

( x i ) SEQUENCE DESCRIPTION: SEQ ID NO:31:

AAGCTTAAAA AAGGGTATAA AATAAA ATG AAA CAA AGT ACT ATT GCA CTG GCA     53

|     |     |     |     |     |     | Met | Lys | Gln | Ser | Thr | Ile | Ala | Leu | Ala |     |
|-----|-----|-----|-----|-----|-----|-----|-----|-----|-----|-----|-----|-----|-----|-----|-----|
|     |     |     |     |     |     | -21 | -20 |     |     |     | -15 |     |     |     |     |

| CTC | TTA | CCG | TTA | CTG | TTT | ACC | CCT | GTG | ACA | AAG | GCC | GCT | GTG | CTA | CCG | 101 |
|-----|-----|-----|-----|-----|-----|-----|-----|-----|-----|-----|-----|-----|-----|-----|-----|-----|
| Leu | Leu | Pro | Leu | Leu | Phe | Thr | Pro | Val | Thr | Lys | Ala | Ala | Val | Leu | Pro |     |
|     |     | -10 |     |     |     |     | -5  |     |     |     |     | 1   |     |     |     |     |
| CAA | GAA | GAA | GAA | GGC | TCG | GGT | ATG | GCC | GCC | TGT | AAT | CTA | CCA | ATA | GTC | 149 |
| Gln | Glu | Glu | Glu | Gly | Ser | Gly | Met | Ala | Ala | Cys | Asn | Leu | Pro | Ile | Val |     |
| 5   |     |     |     |     |     | 10  |     |     |     | 15  |     |     |     |     | 20  |     |
| AGC | GGC | CCC | TGC | CGA | GCC | TTC | ATC | AAG | CTC | TGG | GCA | TTT | GAT | GCT | GTC | 197 |
| Ser | Gly | Pro | Cys | Arg | Ala | Phe | Ile | Lys | Leu | Trp | Ala | Phe | Asp | Ala | Val |     |
|     |     |     |     | 25  |     |     |     |     | 30  |     |     |     |     | 35  |     |     |
| AAG | GGG | AAG | TGC | GTC | CTC | TTC | CCC | TAC | GGG | GGC | TGC | CAG | GGC | AAC | GGG | 245 |
| Lys | Gly | Lys | Cys | Val | Leu | Phe | Pro | Tyr | Gly | Gly | Cys | Gln | Gly | Asn | Gly |     |
|     |     |     | 40  |     |     |     |     | 45  |     |     |     |     | 50  |     |     |     |
| AAC | AAG | TTC | GAC | TCA | GAG | AAG | GAG | TGC | AGA | GAG | TAC | TGC | GGT | GTC | CCT | 293 |
| Asn | Lys | Phe | Asp | Ser | Glu | Lys | Glu | Cys | Arg | Glu | Tyr | Cys | Gly | Val | Pro |     |
|     |     | 55  |     |     |     |     | 60  |     |     |     |     | 65  |     |     |     |     |
| GGT | GAT | GGT | GAT | GAG | GAG | CTG | CTG | CGC | TTC | TCC | AAC | TGACAACTGG  |||| 339 |
| Gly | Asp | Gly | Asp | Glu | Glu | Leu | Leu | Arg | Phe | Ser | Asn |     |     |     |     |     |
|     | 70  |     |     |     |     | 75  |     |     |     |     | 80  |     |     |     |     |     |

ATCC        343

( 2 ) INFORMATION FOR SEQ ID NO:32:

( i ) SEQUENCE CHARACTERISTICS:
        ( A ) LENGTH: 101 amino acids
        ( B ) TYPE: amino acid
        ( D ) TOPOLOGY: linear ( i i ) MOLECULE TYPE: protein ( x i ) SEQUENCE DESCRIPTION: SEQ ID NO:32:

| Met | Lys | Gln | Ser | Thr | Ile | Ala | Leu | Ala | Leu | Leu | Pro | Leu | Leu | Phe | Thr |
|-----|-----|-----|-----|-----|-----|-----|-----|-----|-----|-----|-----|-----|-----|-----|-----|
| -21 | -20 |     |     |     | -15 |     |     |     |     | -10 |     |     |     |     |     |
| Pro | Val | Thr | Lys | Ala | Ala | Val | Leu | Pro | Gln | Glu | Glu | Glu | Gly | Ser | Gly |
| -5  |     |     |     |     | 1   |     |     |     | 5   |     |     |     |     | 10  |     |
| Met | Ala | Ala | Cys | Asn | Leu | Pro | Ile | Val | Ser | Gly | Pro | Cys | Arg | Ala | Phe |
|     |     |     | 15  |     |     |     |     | 20  |     |     |     |     | 25  |     |     |
| Ile | Lys | Leu | Trp | Ala | Phe | Asp | Ala | Val | Lys | Gly | Lys | Cys | Val | Leu | Phe |
|     |     | 30  |     |     |     |     | 35  |     |     |     |     | 40  |     |     |     |
| Pro | Tyr | Gly | Gly | Cys | Gln | Gly | Asn | Gly | Asn | Lys | Phe | Asp | Ser | Glu | Lys |
|     | 45  |     |     |     |     | 50  |     |     |     |     | 55  |     |     |     |     |
| Glu | Cys | Arg | Glu | Tyr | Cys | Gly | Val | Pro | Gly | Asp | Gly | Asp | Glu | Glu | Leu |
| 60  |     |     |     |     | 65  |     |     |     |     | 70  |     |     |     |     | 75  |
| Leu | Arg | Phe | Ser | Asn |
|-----|-----|-----|-----|-----|
|     |     |     |     | 80  |

( 2 ) INFORMATION FOR SEQ ID NO:33:

( i ) SEQUENCE CHARACTERISTICS:
        ( A ) LENGTH: 343 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Eschericia coli
        ( B ) STRAIN: JE5505 (pM765)

( i x ) FEATURE:

( A ) NAME/KEY: sig_peptide
( B ) LOCATION: 27..89

( i x ) FEATURE:
( A ) NAME/KEY: mat_peptide
( B ) LOCATION: 90..329

( i x ) FEATURE:
( A ) NAME/KEY: CDS
( B ) LOCATION: 27..329

( x i ) SEQUENCE DESCRIPTION: SEQ ID NO:33:

| | | | | | | | | | | | | | | | | |
|---|---|---|---|---|---|---|---|---|---|---|---|---|---|---|---|---|
| AAGCTTAAAA | AAGGGTATAA | AATAAA | ATG | AAA | CAA | AGT | ACT | ATT | GCA | CTG | GCA | | | | | 53 |
| | | | Met | Lys | Gln | Ser | Thr | Ile | Ala | Leu | Ala | | | | | |
| | | | -21 | -20 | | | | | | -15 | | | | | | |
| CTC | TTA | CCG | TTA | CTG | TTT | ACC | CCT | GTG | ACA | AAG | GCC | GCT | GTG | CTA | CCG | 101 |
| Leu | Leu | Pro | Leu | Leu | Phe | Thr | Pro | Val | Thr | Lys | Ala | Ala | Val | Leu | Pro | |
| | | -10 | | | | | -5 | | | | | 1 | | | | |
| CAA | GAA | GAA | GAA | GGC | TCG | GGT | ATG | GCC | GCC | TGT | AAT | CTA | CCA | ATA | GTC | 149 |
| Gln | Glu | Glu | Glu | Gly | Ser | Gly | Met | Ala | Ala | Cys | Asn | Leu | Pro | Ile | Val | |
| 5 | | | | | 10 | | | | | 15 | | | | | 20 | |
| GCG | GGC | CCC | TGC | CGA | GCC | TTC | ATC | AAG | CTC | TGG | GCA | TTT | GAT | GCT | GTC | 197 |
| Ala | Gly | Pro | Cys | Arg | Ala | Phe | Ile | Lys | Leu | Trp | Ala | Phe | Asp | Ala | Val | |
| | | | | 25 | | | | | 30 | | | | | 35 | | |
| AAG | GGG | AAG | TGC | GTC | CTC | TTC | CCC | TAC | GGG | GGC | TGC | CAG | GGC | AAC | GGG | 245 |
| Lys | Gly | Lys | Cys | Val | Leu | Phe | Pro | Tyr | Gly | Gly | Cys | Gln | Gly | Asn | Gly | |
| | | | 40 | | | | | 45 | | | | | 50 | | | |
| AAC | AAG | TTC | GAC | TCA | GAG | AAG | GAG | TGC | AGA | GAG | TAC | TGC | GGT | GTC | CCT | 293 |
| Asn | Lys | Phe | Asp | Ser | Glu | Lys | Glu | Cys | Arg | Glu | Tyr | Cys | Gly | Val | Pro | |
| | | 55 | | | | | 60 | | | | | 65 | | | | |
| GGT | GAT | GGT | GAT | GAG | GAG | CTG | CTG | CGC | TTC | TCC | AAC | TGACAACTGG | | | | 339 |
| Gly | Asp | Gly | Asp | Glu | Glu | Leu | Leu | Arg | Phe | Ser | Asn | | | | | |
| | 70 | | | | | 75 | | | | | 80 | | | | | |
| ATCC | | | | | | | | | | | | | | | | 343 |

( 2 ) INFORMATION FOR SEQ ID NO:34:

( i ) SEQUENCE CHARACTERISTICS:
( A ) LENGTH: 101 amino acids
( B ) TYPE: amino acid
( D ) TOPOLOGY: linear ( i i ) MOLECULE TYPE: protein ( x i ) SEQUENCE DESCRIPTION: SEQ ID NO:34:

| | | | | | | | | | | | | | |
|---|---|---|---|---|---|---|---|---|---|---|---|---|---|
| Met | Lys | Gln | Ser | Thr | Ile | Ala | Leu | Ala | Leu | Leu | Pro | Leu | Leu | Phe | Thr |
| -21 | -20 | | | | | -15 | | | | | -10 | | | | |
| Pro | Val | Thr | Lys | Ala | Ala | Val | Leu | Pro | Gln | Glu | Glu | Glu | Gly | Ser | Gly |
| -5 | | | | | 1 | | | | 5 | | | | | 10 | |
| Met | Ala | Ala | Cys | Asn | Leu | Pro | Ile | Val | Ala | Gly | Pro | Cys | Arg | Ala | Phe |
| | | | 15 | | | | | 20 | | | | 25 | | | |
| Ile | Lys | Leu | Trp | Ala | Phe | Asp | Ala | Val | Lys | Gly | Lys | Cys | Val | Leu | Phe |
| | | 30 | | | | | 35 | | | | | 40 | | | |
| Pro | Tyr | Gly | Gly | Cys | Gln | Gly | Asn | Gly | Asn | Lys | Phe | Asp | Ser | Glu | Lys |
| | | 45 | | | | 50 | | | | | 55 | | | | |
| Glu | Cys | Arg | Glu | Tyr | Cys | Gly | Val | Pro | Gly | Asp | Gly | Asp | Glu | Glu | Leu |
| 60 | | | | | 65 | | | | | 70 | | | | | 75 |
| Leu | Arg | Phe | Ser | Asn | | | | | | | | | | | |
| | | | | 80 | | | | | | | | | | | |

( 2 ) INFORMATION FOR SEQ ID NO:35:

( i ) SEQUENCE CHARACTERISTICS:

5,589,360

93

94

-continued (A) LENGTH: 68 amino acids
        (B) TYPE: amino acid
        (D) TOPOLOGY: linear (ii) MOLECULE TYPE: protein (iii) HYPOTHETICAL: NO (v) FRAGMENT TYPE: C-terminal (vi) ORIGINAL SOURCE:
        (A) ORGANISM: Eschericia coli (xi) SEQUENCE DESCRIPTION: SEQ ID NO:35:

| Ala | Ala | Cys | Asn | Leu | Pro | Ile | Val | Arg | Gly | Pro | Cys | Arg | Ala | Phe | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Lys | Leu | Trp | Ala | Phe | Asp | Ala | Val | Lys | Gly | Lys | Cys | Val | Leu | Phe | Pro |
|     |     |     | 20  |     |     |     |     | 25  |     |     |     |     | 30  |     |     |
| Tyr | Gly | Gly | Cys | Gln | Gly | Asn | Gly | Asn | Lys | Phe | Asp | Ser | Glu | Lys | Glu |
|     |     | 35  |     |     |     | 40  |     |     |     |     | 45  |     |     |     |     |
| Cys | Arg | Glu | Tyr | Cys | Gly | Val | Pro | Gly | Asp | Gly | Asp | Glu | Glu | Leu | Leu |
|     | 50  |     |     |     | 55  |     |     |     |     | 60  |     |     |     |     |     |
| Arg | Phe | Ser | Asn |
| 65  |     |     |     |

(2) INFORMATION FOR SEQ ID NO:36:

(i) SEQUENCE CHARACTERISTICS:
        (A) LENGTH: 68 amino acids
        (B) TYPE: amino acid
        (D) TOPOLOGY: linear (ii) MOLECULE TYPE: protein (iii) HYPOTHETICAL: NO (v) FRAGMENT TYPE: C-terminal (vi) ORIGINAL SOURCE:
        (A) ORGANISM: Eschericia coli (xi) SEQUENCE DESCRIPTION: SEQ ID NO:36:

| Ala | Ala | Cys | Asn | Leu | Pro | Ile | Val | Arg | Gly | Pro | Cys | Arg | Ala | Phe | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Arg | Leu | Trp | Ala | Phe | Asp | Ala | Val | Lys | Gly | Lys | Cys | Val | Leu | Phe | Pro |
|     |     |     | 20  |     |     |     |     | 25  |     |     |     |     | 30  |     |     |
| Tyr | Gly | Gly | Cys | Gln | Gly | Asn | Gly | Asn | Lys | Phe | Asp | Ser | Glu | Lys | Glu |
|     |     | 35  |     |     |     | 40  |     |     |     |     | 45  |     |     |     |     |
| Cys | Arg | Glu | Tyr | Cys | Gly | Val | Pro | Gly | Asp | Gly | Asp | Glu | Glu | Leu | Leu |
|     | 50  |     |     |     | 55  |     |     |     |     | 60  |     |     |     |     |     |
| Arg | Phe | Ser | Asn |
| 65  |     |     |     |

(2) INFORMATION FOR SEQ ID NO:37:

(i) SEQUENCE CHARACTERISTICS:
        (A) LENGTH: 68 amino acids
        (B) TYPE: amino acid
        (D) TOPOLOGY: linear (ii) MOLECULE TYPE: protein (iii) HYPOTHETICAL: NO (v) FRAGMENT TYPE: C-terminal (vi) ORIGINAL SOURCE:
        (A) ORGANISM: Eschericia coli ( x i ) SEQUENCE DESCRIPTION: SEQ ID NO:37:

| Ala | Ala | Cys | Asn | Leu | Pro | Ile | Val | Gln | Gly | Pro | Cys | Arg | Ala | Phe | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Lys | Leu | Trp | Ala | Phe | Asp | Ala | Val | Lys | Gly | Lys | Cys | Val | Leu | Phe | Pro |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Tyr | Gly | Gly | Cys | Gln | Gly | Asn | Gly | Asn | Lys | Phe | Asp | Ser | Glu | Lys | Glu |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Cys | Arg | Glu | Tyr | Cys | Gly | Val | Pro | Gly | Asp | Gly | Asp | Glu | Glu | Leu | Leu |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Arg | Phe | Ser | Asn |
|-----|-----|-----|-----|
| 65  |     |     |     |

( 2 ) INFORMATION FOR SEQ ID NO:38:

( i ) SEQUENCE CHARACTERISTICS:
        ( A ) LENGTH: 68 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: C-terminal ( v i ) ORIGINAL SOURCE:
        ( A ) ORGANISM: Eschericia coli ( x i ) SEQUENCE DESCRIPTION: SEQ ID NO:38:

| Ala | Ala | Cys | Asn | Leu | Pro | Ile | Val | Asp | Gly | Pro | Cys | Arg | Ala | Phe | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Lys | Leu | Trp | Ala | Phe | Asp | Ala | Val | Lys | Gly | Lys | Cys | Val | Leu | Phe | Pro |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Tyr | Gly | Gly | Cys | Gln | Gly | Asn | Gly | Asn | Lys | Phe | Asp | Ser | Glu | Lys | Glu |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Cys | Arg | Glu | Tyr | Cys | Gly | Val | Pro | Gly | Asp | Gly | Asp | Glu | Glu | Leu | Leu |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Arg | Phe | Ser | Asn |
|-----|-----|-----|-----|
| 65  |     |     |     |

( 2 ) INFORMATION FOR SEQ ID NO:39:

( i ) SEQUENCE CHARACTERISTICS:
        ( A ) LENGTH: 68 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: C-terminal ( v i ) ORIGINAL SOURCE:
        ( A ) ORGANISM: Eschericia coli ( x i ) SEQUENCE DESCRIPTION: SEQ ID NO:39:

| Ala | Ala | Cys | Asn | Leu | Pro | Ile | Val | Leu | Gly | Pro | Cys | Arg | Ala | Phe | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Lys | Leu | Trp | Ala | Phe | Asp | Ala | Val | Lys | Gly | Lys | Cys | Val | Leu | Phe | Pro |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Tyr | Gly | Gly | Cys | Gln | Gly | Asn | Gly | Asn | Lys | Phe | Asp | Ser | Glu | Lys | Glu |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

Cys Arg Glu Tyr Cys Gly Val Pro Gly Asp Gly Asp Glu Glu Leu Leu
50                  55                  60

Arg Phe Ser Asn
65

( 2 ) INFORMATION FOR SEQ ID NO:40:

( i ) SEQUENCE CHARACTERISTICS:
        ( A ) LENGTH: 68 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: C-terminal ( v i ) ORIGINAL SOURCE:
        ( A ) ORGANISM: Eschericia coli ( x i ) SEQUENCE DESCRIPTION: SEQ ID NO:40:

Ala Ala Cys Asn Leu Pro Ile Val Glu Gly Pro Cys Arg Ala Phe Ile
1               5                   10                  15

Lys Leu Trp Ala Phe Asp Ala Val Lys Gly Lys Cys Val Leu Phe Pro
            20                  25                  30

Tyr Gly Gly Cys Gln Gly Asn Gly Asn Lys Phe Glu Ser Glu Lys Glu
        35                  40                  45

Cys Arg Glu Tyr Cys Gly Val Pro Gly Asp Gly Asp Glu Glu Leu Leu
50                  55                  60

Arg Phe Ser Asn
65

( 2 ) INFORMATION FOR SEQ ID NO:41:

( i ) SEQUENCE CHARACTERISTICS:
        ( A ) LENGTH: 68 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: C-terminal ( v i ) ORIGINAL SOURCE:
        ( A ) ORGANISM: Eschericia coli ( x i ) SEQUENCE DESCRIPTION: SEQ ID NO:41:

Ala Ala Cys Asn Leu Pro Ile Val Asn Gly Pro Cys Arg Ala Phe Ile
1               5                   10                  15

Lys Leu Trp Ala Phe Asp Ala Val Lys Gly Lys Cys Val Leu Phe Pro
            20                  25                  30

Tyr Gly Gly Cys Gln Gly Asn Gly Asn Lys Phe Asp Ser Glu Lys Glu
        35                  40                  45

Cys Arg Glu Tyr Cys Gly Val Pro Gly Asp Gly Asp Glu Glu Leu Leu
50                  55                  60

Arg Phe Ser Asn
65

( 2 ) INFORMATION FOR SEQ ID NO:42:

( i ) SEQUENCE CHARACTERISTICS:
        ( A ) LENGTH: 68 amino acids
        ( B ) TYPE: amino acid ( D ) TOPOLOGY: linear ( i i ) MOLECULE TYPE: protein ( i i i ) HYPOTHETICAL: NO ( v ) FRAGMENT TYPE: C-terminal ( v i ) ORIGINAL SOURCE:
    ( A ) ORGANISM: Eschericia coli ( x i ) SEQUENCE DESCRIPTION: SEQ ID NO:42:

```
Ala Ala Cys Asn Leu Pro Ile Val Ser Gly Pro Cys Arg Ala Phe Ile
 1               5                  10                  15
Lys Leu Trp Ala Phe Asp Ala Val Lys Gly Lys Cys Val Leu Phe Pro
            20                  25                  30
Tyr Gly Gly Cys Gln Gly Asn Gly Asn Lys Phe Asp Ser Glu Lys Glu
        35                  40                  45
Cys Arg Glu Tyr Cys Gly Val Pro Gly Asp Gly Asp Glu Glu Leu Leu
    50                  55                  60
Arg Phe Ser Asn
65
```

( 2 ) INFORMATION FOR SEQ ID NO:43:

( i ) SEQUENCE CHARACTERISTICS:
        ( A ) LENGTH: 68 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: C-terminal ( v i ) ORIGINAL SOURCE:
        ( A ) ORGANISM: Eschericia coli ( x i ) SEQUENCE DESCRIPTION: SEQ ID NO:43:

```
Ala Ala Cys Asn Leu Pro Ile Val Ala Gly Pro Cys Arg Ala Phe Ile
 1               5                  10                  15
Lys Leu Trp Ala Phe Asp Ala Val Lys Gly Lys Cys Val Leu Phe Pro
            20                  25                  30
Tyr Gly Gly Cys Gln Gly Asn Gly Asn Lys Phe Asp Ser Glu Lys Glu
        35                  40                  45
Cys Arg Glu Tyr Cys Gly Val Pro Gly Asp Gly Asp Glu Glu Leu Leu
    50                  55                  60
Arg Phe Ser Asn
65
```

( 2 ) INFORMATION FOR SEQ ID NO:44:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: -
        ( B ) LOCATION: 1..32

(D) OTHER INFORMATION: /label=oligonucleotide
/ note= "Figure 1, S33"

(xi) SEQUENCE DESCRIPTION: SEQ ID NO:44:

AGCTTAAAAA AGGGTATAAA ATAAAATGAA AC 32

(2) INFORMATION FOR SEQ ID NO:45:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (ix) FEATURE:
(A) NAME/KEY: -
(B) LOCATION: 1..36
(D) OTHER INFORMATION: /label=oligonucleotide
/ note= "Figure 1, S34"

(xi) SEQUENCE DESCRIPTION: SEQ ID NO:45:

AGTACTTTGT TTCATTTTAT TTTATACCCT TTTTTA 36

(2) INFORMATION FOR SEQ ID NO:46:

(i) SEQUENCE CHARACTERISTICS:
(A) LENGTH: 38 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (ix) FEATURE:
(A) NAME/KEY: -
(B) LOCATION: 1..38
(D) OTHER INFORMATION: /label=oligonucleotide
/ note= "Figure 1, S35"

(xi) SEQUENCE DESCRIPTION: SEQ ID NO:46:

AAAGTACTAT TGCACTGGCA CTCTTACCGT TACTGTTT 38

(2) INFORMATION FOR SEQ ID NO:47:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (ix) FEATURE:
(A) NAME/KEY: -
(B) LOCATION: 1..36
(D) OTHER INFORMATION: /label=oligonucleotide
/ note= "Figure 1, S18"

(xi) SEQUENCE DESCRIPTION: SEQ ID NO:47:

AGGGGTAAAC AGTAACGGTA AGAGTGCCAG TGCAAT    36

( 2 ) INFORMATION FOR SEQ ID NO:48:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: -
        ( B ) LOCATION: 1..32
        ( D ) OTHER INFORMATION: /label=oligonucleotide
            / note= "Figure 1, S19"

( x i ) SEQUENCE DESCRIPTION: SEQ ID NO:48:

ACCCCTGTGA CAAAAGCCGA CTCCCTAGGT CG    32

( 2 ) INFORMATION FOR SEQ ID NO:49:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: -
        ( B ) LOCATION: 1..26
        ( D ) OTHER INFORMATION: /label=oligonucleotide
            / note= "Figure 1, S20"

( x i ) SEQUENCE DESCRIPTION: SEQ ID NO:49:

GCACCTAGGG AGTCGGCTTT TGTCAC    26

( 2 ) INFORMATION FOR SEQ ID NO:50:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: -
        ( B ) LOCATION: 1..25
        ( D ) OTHER INFORMATION: /label=primer
            / note= "Y46E primer"

( x i ) SEQUENCE DESCRIPTION: SEQ ID NO:50:

GGAACAAGTT CGAATCAGAG AAGGA    25

( 2 ) INFORMATION FOR SEQ ID NO:51:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
   ( A ) NAME/KEY: -
   ( B ) LOCATION: 1..21
   ( D ) OTHER INFORMATION: /label=primer
     / note= "ScaI sense primer"

( x i ) SEQUENCE DESCRIPTION: SEQ ID NO:51:

ACTATTGCAC TGGCACTCTT A                21

( 2 ) INFORMATION FOR SEQ ID NO:52:

( i ) SEQUENCE CHARACTERISTICS:
   ( A ) LENGTH: 26 base pairs
   ( B ) TYPE: nucleic acid
   ( C ) STRANDEDNESS: single
   ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
   ( A ) NAME/KEY: -
   ( B ) LOCATION: 1..26
   ( D ) OTHER INFORMATION: /label=primer
     / note= "Bam HI primer"

( x i ) SEQUENCE DESCRIPTION: SEQ ID NO:52:

TGGATCCAGT TGTCAGTTGG AGAAGC             26

( 2 ) INFORMATION FOR SEQ ID NO:53:

( i ) SEQUENCE CHARACTERISTICS:
   ( A ) LENGTH: 28 base pairs
   ( B ) TYPE: nucleic acid
   ( C ) STRANDEDNESS: single
   ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
   ( A ) NAME/KEY: -
   ( B ) LOCATION: 1..28
   ( D ) OTHER INFORMATION: /label=oligonucleotide
     / note= "oligomer TV12DD"

( x i ) SEQUENCE DESCRIPTION: SEQ ID NO:53:

TGACAAAGGC CGACGACGCC GCCTGCAA           28

( 2 ) INFORMATION FOR SEQ ID NO:54:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
    ( A ) NAME/KEY: -
    ( B ) LOCATION: 1..21
    ( D ) OTHER INFORMATION: /label=primer
        / note= "HindIII primer"

( x i ) SEQUENCE DESCRIPTION: SEQ ID NO:54:

ACGCAAGTTC ACGTAAAAAG C                                  21

( 2 ) INFORMATION FOR SEQ ID NO:55:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
    ( A ) NAME/KEY: -
    ( B ) LOCATION: 1..31
    ( D ) OTHER INFORMATION: /label=primer
        / note= "Q19K primer"

( x i ) SEQUENCE DESCRIPTION: SEQ ID NO:55:

CAAATGCCCA GAGCTTGATG AAGGCTCGGC A                  31

( 2 ) INFORMATION FOR SEQ ID NO:56:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
    ( A ) NAME/KEY: -
    ( B ) LOCATION: 1..21
    ( D ) OTHER INFORMATION: /label=primer
        / note= "pBR BamHI primer"

( x i ) SEQUENCE DESCRIPTION: SEQ ID NO:56:

ACGATGCGTT CCGGCGTAGA G                                  21

( 2 ) INFORMATION FOR SEQ ID NO:57:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
    ( A ) NAME/KEY: -
    ( B ) LOCATION: 1..40
    ( D ) OTHER INFORMATION: /label=primer
        / note= "AN68 primer"

( x i ) SEQUENCE DESCRIPTION: SEQ ID NO:57:

CTATTGGTAG ATTACAGGCC GCGGCCTTTG TCACAGGGGT    40

( 2 ) INFORMATION FOR SEQ ID NO:58:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: -
        ( B ) LOCATION: 1..30
        ( D ) OTHER INFORMATION: /label=primer
            / note= "SacII primer"

( x i ) SEQUENCE DESCRIPTION: SEQ ID NO:58:

AAGGCCGCGG CCTGTAATCT ACCAATAGTC    30

( 2 ) INFORMATION FOR SEQ ID NO:59:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: -
        ( B ) LOCATION: 1..32
        ( D ) OTHER INFORMATION: /label=primer
            / note= "Q19R primer"

( x i ) SEQUENCE DESCRIPTION: SEQ ID NO:59:

ATCAAATGCC CAGAGACGGA TGAAGGCTCG GC    32

( 2 ) INFORMATION FOR SEQ ID NO:60:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: -
        ( B ) LOCATION: 1..27

(D) OTHER INFORMATION: /label=primer
/ note= "R11E primer"

(x i) SEQUENCE DESCRIPTION: SEQ ID NO:60:

TCGGCAGGGG CCTTCGACTA TTGGTAG    27

(2) INFORMATION FOR SEQ ID NO:61:

(i) SEQUENCE CHARACTERISTICS:
(A) LENGTH: 155 base pairs
(B) TYPE: nucleic acid
(C) STRANDEDNESS: double
(D) TOPOLOGY: linear (i i) MOLECULE TYPE: DNA (genomic)

(i i i) HYPOTHETICAL: NO (i v) ANTI-SENSE: NO (i x) FEATURE:
(A) NAME/KEY: -
(B) LOCATION: 5..151
(D) OTHER INFORMATION: /label=linker
/ note= "double stranded portion of Linker 710
(Figure 34)."

(i x) FEATURE:
(A) NAME/KEY: misc_feature
(B) LOCATION: 1..4
(D) OTHER INFORMATION: /label=5'_extension
/ note= "HindII compatible 5'overhang"

(i x) FEATURE:
(A) NAME/KEY: misc_feature
(B) LOCATION: 151..155
(D) OTHER INFORMATION: /label=3'_extension
/ note= "ApaI compatible 3'overhang"

(x i) SEQUENCE DESCRIPTION: SEQ ID NO:61:

AGCTTAAAAA AGGGTATAAA ATAAAATGAA ACAAAGTACT ATTGCACTGG CACTCTTACC    60

GTTACTGTTT ACCCCTGTGA CAAAGGCCGC TGTGCTACCG CAAGAAGAAG AAGGCTCGGG    120

TATGGCCGCC TGTAATCTAC CAATAGTCCG GGGCC    155

(2) INFORMATION FOR SEQ ID NO:62:

(i) SEQUENCE CHARACTERISTICS:
(A) LENGTH: 25 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (i v) ANTI-SENSE: NO (i x) FEATURE:
(A) NAME/KEY: -
(B) LOCATION: 1..25
(D) OTHER INFORMATION: /label=primer
/ note= "Y46D primer"

(x i) SEQUENCE DESCRIPTION: SEQ ID NO:62:

GGGAACAAGT TCGACTCAGA GAAGG    25

(2) INFORMATION FOR SEQ ID NO:63:

(i) SEQUENCE CHARACTERISTICS:
(A) LENGTH: 25 base pairs
(B) TYPE: nucleic acid (C) STRANDEDNESS: single
(D) TOPOLOGY: linear (i i) MOLECULE TYPE: DNA (genomic)

(i i i) HYPOTHETICAL: NO (i v) ANTI-SENSE: NO (i x) FEATURE:
    (A) NAME/KEY: -
    (B) LOCATION: 1..25
    (D) OTHER INFORMATION: /label=primer
        / note= "R11Q primer"

(x i) SEQUENCE DESCRIPTION: SEQ ID NO:63:

CGGCAGGGGC CCTGGACTAT TGGTA                        25

(2) INFORMATION FOR SEQ ID NO:64:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (i x) FEATURE:
        (A) NAME/KEY: -
        (B) LOCATION: 1..25
        (D) OTHER INFORMATION: /label=primer
            / note= "R11D primer"

(x i) SEQUENCE DESCRIPTION: SEQ ID NO:64:

CGGCAGGGGC CATCGACTAT TGGTA                        25

(2) INFORMATION FOR SEQ ID NO:65:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (i x) FEATURE:
        (A) NAME/KEY: -
        (B) LOCATION: 1..25
        (D) OTHER INFORMATION: /label=primer
            / note= "R11L primer"

(x i) SEQUENCE DESCRIPTION: SEQ ID NO:65:

CGGCAGGGGC CCAGGACTAT TGGTA                        25

(2) INFORMATION FOR SEQ ID NO:66:

(i) SEQUENCE CHARACTERISTICS:
        (A) LENGTH: 153 base pairs
        (B) TYPE: nucleic acid
        (C) STRANDEDNESS: double
        (D) TOPOLOGY: linear (i i) MOLECULE TYPE: DNA (genomic)

(iii) HYPOTHETICAL: NO (iv) ANTI-SENSE: NO (ix) FEATURE:
(A) NAME/KEY: -
(B) LOCATION: 1..153
(D) OTHER INFORMATION: /label=sequence
/ note= "Formula 2, encodes the amino acid sequence of Formula 1"

(ix) FEATURE:
(A) NAME/KEY: CDS
(B) LOCATION: 1..153
(D) OTHER INFORMATION: /product="FXa inhibitor"

(xi) SEQUENCE DESCRIPTION: SEQ ID NO:66:

| TGC | AAT | CTC | CCC | ATA | GTC | CGG | GGC | CCC | TGC | CGA | GCC | TTC | ATC | CAG | CTC | 48 |
|---|---|---|---|---|---|---|---|---|---|---|---|---|---|---|---|---|
| Cys | Asn | Leu | Pro | Ile | Val | Arg | Gly | Pro | Cys | Arg | Ala | Phe | Ile | Gln | Leu | |
| 1 | | | | 5 | | | | | 10 | | | | | 15 | | |

| TGG | GCA | TTT | GAT | GCT | GTC | AAG | GGG | AAG | TGC | GTC | CTC | TTC | CCC | TAC | GGG | 96 |
|---|---|---|---|---|---|---|---|---|---|---|---|---|---|---|---|---|
| Trp | Ala | Phe | Asp | Ala | Val | Lys | Gly | Lys | Cys | Val | Leu | Phe | Pro | Tyr | Gly | |
| | | | 20 | | | | | 25 | | | | | 30 | | | |

| GGC | TGC | CAG | GGC | AAC | GGG | AAC | AAG | TTC | TAC | TCA | GAG | AAG | GAG | TGC | AGA | 144 |
|---|---|---|---|---|---|---|---|---|---|---|---|---|---|---|---|---|
| Gly | Cys | Gln | Gly | Asn | Gly | Asn | Lys | Phe | Tyr | Ser | Glu | Lys | Glu | Cys | Arg | |
| | | 35 | | | | | 40 | | | | | 45 | | | | |

| GAG | TAC | TGC | 153 |
|---|---|---|---|
| Glu | Tyr | Cys | |
| 50 | | | |

(2) INFORMATION FOR SEQ ID NO:67:

(i) SEQUENCE CHARACTERISTICS:
(A) LENGTH: 51 amino acids
(B) TYPE: amino acid
(D) TOPOLOGY: linear (ii) MOLECULE TYPE: protein (xi) SEQUENCE DESCRIPTION: SEQ ID NO:67:

| Cys | Asn | Leu | Pro | Ile | Val | Arg | Gly | Pro | Cys | Arg | Ala | Phe | Ile | Gln | Leu |
|---|---|---|---|---|---|---|---|---|---|---|---|---|---|---|---|
| 1 | | | | 5 | | | | | 10 | | | | | 15 | |

| Trp | Ala | Phe | Asp | Ala | Val | Lys | Gly | Lys | Cys | Val | Leu | Phe | Pro | Tyr | Gly |
|---|---|---|---|---|---|---|---|---|---|---|---|---|---|---|---|
| | | | 20 | | | | | 25 | | | | | 30 | | |

| Gly | Cys | Gln | Gly | Asn | Gly | Asn | Lys | Phe | Tyr | Ser | Glu | Lys | Glu | Cys | Arg |
|---|---|---|---|---|---|---|---|---|---|---|---|---|---|---|---|
| | | 35 | | | | | 40 | | | | | 45 | | | |

| Glu | Tyr | Cys |
|---|---|---|
| 50 | | |

(2) INFORMATION FOR SEQ ID NO:68:

(i) SEQUENCE CHARACTERISTICS:
(A) LENGTH: 12 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (ix) FEATURE:
(A) NAME/KEY: -
(B) LOCATION: 1..12
(D) OTHER INFORMATION: /label=5'_extension
/ note= "preferable additional amino terminal codons for peptide protease inhibitors"

( i x ) FEATURE:
                ( A ) NAME/KEY: CDS
                ( B ) LOCATION: 1..12
                ( D ) OTHER INFORMATION: /product="amino terminal addition"
                        / note= "preferable amino acids to be added to
                        amino terminus of peptide protease inhibitors"

( x i ) SEQUENCE DESCRIPTION: SEQ ID NO:68:

```
GAC   GAC   GCC   GCC                                                           1 2
Asp   Asp   Ala   Ala
  1
```

( 2 ) INFORMATION FOR SEQ ID NO:69:

( i ) SEQUENCE CHARACTERISTICS:
                ( A ) LENGTH: 4 amino acids
                ( B ) TYPE: amino acid
                ( D ) TOPOLOGY: linear ( i i ) MOLECULE TYPE: protein ( x i ) SEQUENCE DESCRIPTION: SEQ ID NO:69:

```
Asp   Asp   Ala   Ala
  1
```

( 2 ) INFORMATION FOR SEQ ID NO:70:

( i ) SEQUENCE CHARACTERISTICS:
                ( A ) LENGTH: 12 base pairs
                ( B ) TYPE: nucleic acid
                ( C ) STRANDEDNESS: double
                ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
                ( A ) NAME/KEY: -
                ( B ) LOCATION: 1..12
                ( D ) OTHER INFORMATION: /label=sequence
                        / note= "preferable codons as 5'extensions of DNA
                        encoding peptide protease inhibitors"

( i x ) FEATURE:
                ( A ) NAME/KEY: CDS
                ( B ) LOCATION: 1..12
                ( D ) OTHER INFORMATION: /product="amino terminal
                        extension"
                        / note= "preferable amino acids for amino terminal
                        extension of peptide protease inhibitors"

( x i ) SEQUENCE DESCRIPTION: SEQ ID NO:70:

```
ACC   GTC   GCC   GCC                                                           1 2
Thr   Val   Ala   Ala
  1
```

( 2 ) INFORMATION FOR SEQ ID NO:71:

( i ) SEQUENCE CHARACTERISTICS:
                ( A ) LENGTH: 4 amino acids
                ( B ) TYPE: amino acid
                ( D ) TOPOLOGY: linear ( i i ) MOLECULE TYPE: protein ( x i ) SEQUENCE DESCRIPTION: SEQ ID NO:71:

```
Thr   Val   Ala   Ala
  1
```

(2) INFORMATION FOR SEQ ID NO:72:

(i) SEQUENCE CHARACTERISTICS:
(A) LENGTH: 45 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (ix) FEATURE:
(A) NAME/KEY: -
(B) LOCATION: 1..45
(D) OTHER INFORMATION: /label=sequence
/ note= "preferable codons encoding carboxy
terminal extension of peptide protease inhibitors"

(ix) FEATURE:
(A) NAME/KEY: CDS
(B) LOCATION: 1..45
(D) OTHER INFORMATION: /product="carboxy terminal amino
acids"
/ note= "preferable amino acids for carboxy
terminal extension of peptide protease inhibitors"

(xi) SEQUENCE DESCRIPTION: SEQ ID NO:72:

| GGT | GTC | CCT | GGT | GAT | GGT | GAT | GAG | GAG | CTG | CTG | CGC | TTC | TCC | AAC | 45 |
|-----|-----|-----|-----|-----|-----|-----|-----|-----|-----|-----|-----|-----|-----|-----|----|
| Gly | Val | Pro | Gly | Asp | Gly | Asp | Glu | Glu | Leu | Leu | Arg | Phe | Ser | Asn | |
| 1 | | | | 5 | | | | | 10 | | | | | 15 | |

(2) INFORMATION FOR SEQ ID NO:73:

(i) SEQUENCE CHARACTERISTICS:
(A) LENGTH: 15 amino acids
(B) TYPE: amino acid
(D) TOPOLOGY: linear (ii) MOLECULE TYPE: protein (xi) SEQUENCE DESCRIPTION: SEQ ID NO:73:

Gly Val Pro Gly Asp Gly Asp Glu Glu Leu Leu Arg Phe Ser Asn
1               5                   10                  15

(2) INFORMATION FOR SEQ ID NO:74:

(i) SEQUENCE CHARACTERISTICS:
(A) LENGTH: 210 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (ix) FEATURE:
(A) NAME/KEY: -
(B) LOCATION: 1..210
(D) OTHER INFORMATION: /label=sequence
/ note= "encodes TN70 polypeptide"

(ix) FEATURE:
(A) NAME/KEY: CDS
(B) LOCATION: 1..210

(xi) SEQUENCE DESCRIPTION: SEQ ID NO:74:

| ACC | GTC | GCC | GCC | TGC | AAT | CTC | CCC | ATA | GTC | CGG | GGC | CCC | TGC | CGA | GCC | 48 |
|-----|-----|-----|-----|-----|-----|-----|-----|-----|-----|-----|-----|-----|-----|-----|-----|----|
| Thr | Val | Ala | Ala | Cys | Asn | Leu | Pro | Ile | Val | Arg | Gly | Pro | Cys | Arg | Ala | |
| 1 | | | | 5 | | | | | 10 | | | | | 15 | | |

```
TTC ATC CAG CTC TGG GCA TTT GAT GCT GTC AAG GGG AAG TGC GTC CTC    96
Phe Ile Gln Leu Trp Ala Phe Asp Ala Val Lys Gly Lys Cys Val Leu
            20                  25                  30

TTC CCC TAC GGG GGC TGC CAG GGC AAC GGG AAC AAG TTC TAC TCA GAG   144
Phe Pro Tyr Gly Gly Cys Gln Gly Asn Gly Asn Lys Phe Tyr Ser Glu
        35                  40                  45

AAG GAG TGC AGA GAG TAC TGC GGT GTC CCT GGT GAT GGT GAT GAG GAG   192
Lys Glu Cys Arg Glu Tyr Cys Gly Val Pro Gly Asp Gly Asp Glu Glu
    50                  55                  60

CTG CTG CGC TTC TCC AAC                                           210
Leu Leu Arg Phe Ser Asn
65                  70
```

( 2 ) INFORMATION FOR SEQ ID NO:75:

( i ) SEQUENCE CHARACTERISTICS:
        ( A ) LENGTH: 70 amino acids
        ( B ) TYPE: amino acid
        ( D ) TOPOLOGY: linear ( i i ) MOLECULE TYPE: protein ( x i ) SEQUENCE DESCRIPTION: SEQ ID NO:75:

```
Thr Val Ala Ala Cys Asn Leu Pro Ile Val Arg Gly Pro Cys Arg Ala
1               5                   10                  15

Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Tyr Ser Glu
        35                  40                  45

Lys Glu Cys Arg Glu Tyr Cys Gly Val Pro Gly Asp Gly Asp Glu Glu
    50                  55                  60

Leu Leu Arg Phe Ser Asn
65                  70
```

( 2 ) INFORMATION FOR SEQ ID NO:76:

( i ) SEQUENCE CHARACTERISTICS:
        ( A ) LENGTH: 68 amino acids
        ( B ) TYPE: amino acid
        ( D ) TOPOLOGY: linear ( i i ) MOLECULE TYPE: protein ( v ) FRAGMENT TYPE: internal ( i x ) FEATURE:
        ( A ) NAME/KEY: Protein
        ( B ) LOCATION: 1..68
        ( D ) OTHER INFORMATION: /label=sequence
                / note= "AN68 polypeptide"

( x i ) SEQUENCE DESCRIPTION: SEQ ID NO:76:

```
Ala Ala Cys Asn Leu Pro Ile Val Arg Gly Pro Cys Arg Ala Phe Ile
1               5                   10                  15

Gln Leu Trp Ala Phe Asp Ala Val Lys Gly Lys Cys Val Leu Phe Pro
            20                  25                  30

Tyr Gly Gly Cys Gln Gly Asn Gly Asn Lys Phe Tyr Ser Glu Lys Glu
        35                  40                  45

Cys Arg Glu Tyr Cys Gly Val Pro Gly Asp Gly Asp Glu Glu Leu Leu
    50                  55                  60

Arg Phe Ser Asn
65
```